(12) United States Patent
Harding et al.

(10) Patent No.: US 8,939,576 B2
(45) Date of Patent: Jan. 27, 2015

(54) OPTICAL ELEMENT FOR CORRECTING COLOR BLINDNESS

(75) Inventors: Brett T. Harding, Carlsbad, CA (US); Sheng Li, Vista, CA (US); Amane Mochizuki, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 13/565,677

(22) Filed: Aug. 2, 2012

(65) Prior Publication Data

US 2013/0057824 A1 Mar. 7, 2013

Related U.S. Application Data

(60) Provisional application No. 61/515,764, filed on Aug. 5, 2011, provisional application No. 61/544,212, filed on Oct. 6, 2011, provisional application No. 61/589,136, filed on Jan. 20, 2012, provisional application No. 61/677,928, filed on Jul. 31, 2012.

(51) Int. Cl.
| | |
|---|---|
| *G02C 7/10* | (2006.01) |
| *G09G 3/30* | (2006.01) |
| *F21V 9/16* | (2006.01) |
| *G06F 3/041* | (2006.01) |
| *C09B 57/00* | (2006.01) |
| *C09B 69/10* | (2006.01) |
| *C09B 3/20* | (2006.01) |
| *G02B 1/04* | (2006.01) |

(52) U.S. Cl.
CPC .. *G09G 3/30* (2013.01); *F21V 9/16* (2013.01); *G02C 7/104* (2013.01); *G06F 3/041* (2013.01); *C09B 57/00* (2013.01); *C09B 57/008* (2013.01); *C09B 69/102* (2013.01); *C09B 69/109* (2013.01); *C09B 3/20* (2013.01); *C09B 69/103* (2013.01); *G02B 1/04* (2013.01)
USPC ............ 351/159.02; 351/159.24; 351/159.3; 351/159.32; 351/159.49

(58) Field of Classification Search
USPC ............... 351/159.24, 159.3, 159.32, 159.49, 351/159.65, 159.78, 159.81
See application file for complete search history.

(56) References Cited

U.S. PATENT DOCUMENTS

| | | | |
|---|---|---|---|
| 2,498,593 | A | 2/1950 | Switzer |
| 3,189,914 | A | 6/1965 | Gusewitch et al. |
| 3,214,832 | A | 11/1965 | Schwinghamer |
| 3,426,212 | A | 2/1969 | Klass |
| 3,586,423 | A | 6/1971 | Zeltzer |
| 3,701,590 | A | 10/1972 | Zeltzer |
| 3,877,797 | A | 4/1975 | Thornton |

(Continued)

FOREIGN PATENT DOCUMENTS

| | | |
|---|---|---|
| DE | 10259261 | 7/2004 |
| GB | 1419985 | 5/1976 |

(Continued)

OTHER PUBLICATIONS

International Search Report for PCT/US2012/049493 filed on Aug. 3, 2012.

*Primary Examiner* — Suchin Parihar
*Assistant Examiner* — William R Alexander
(74) *Attorney, Agent, or Firm* — K&L Gates LLP; Louis C. Cullman; Brent A. Johnson

(57) ABSTRACT

Described herein are devices, compositions, and methods for improving color discernment.

21 Claims, 11 Drawing Sheets

(56) References Cited

U.S. PATENT DOCUMENTS

| | | | |
|---|---|---|---|
| 3,986,997 | A | 10/1976 | Clark |
| 4,027,073 | A | 5/1977 | Clark |
| 4,102,567 | A | 7/1978 | Cuffe |
| 4,299,746 | A | 11/1981 | Frye |
| 4,300,819 | A | 11/1981 | Taylor |
| 4,309,319 | A | 1/1982 | Vaughn |
| 4,320,939 | A | 3/1982 | Mueller |
| 4,324,712 | A | 4/1982 | Vaughn |
| 4,324,839 | A | 4/1982 | Frye |
| 4,413,088 | A | 11/1983 | Frye |
| 4,414,349 | A | 11/1983 | Vaughn |
| 4,548,975 | A | 10/1985 | Lewis |
| 4,553,975 | A | 11/1985 | Su |
| 4,559,059 | A | 12/1985 | Su |
| 4,687,679 | A | 8/1987 | Beale |
| 4,702,574 | A | 10/1987 | Bawa |
| 4,733,959 | A | 3/1988 | Claussen |
| 4,762,730 | A | 8/1988 | Enke |
| 4,824,234 | A | 4/1989 | Sparks |
| 4,998,817 | A | 3/1991 | Zeltzer |
| 5,013,608 | A | 5/1991 | Guest |
| 5,021,196 | A | 6/1991 | Crano |
| 5,102,695 | A | 4/1992 | Guest |
| 5,104,929 | A | 4/1992 | Bilkadi |
| 5,219,497 | A | 6/1993 | Blum |
| 5,221,560 | A | 6/1993 | Perkins |
| 5,225,244 | A | 7/1993 | Aharoni |
| 5,296,295 | A | 3/1994 | Perkins |
| 5,363,151 | A | 11/1994 | Biays |
| 5,363,152 | A | 11/1994 | Reed |
| 5,369,453 | A | 11/1994 | Chen |
| 5,408,278 | A | 4/1995 | Christman |
| 5,470,502 | A | 11/1995 | Hahn |
| 5,583,742 | A | 12/1996 | Noda |
| 5,586,002 | A | 12/1996 | Notarianni |
| 5,617,154 | A | 4/1997 | Hoffman |
| 5,665,814 | A | 9/1997 | Lewis |
| 5,774,202 | A | 6/1998 | Abraham et al. |
| 5,801,808 | A | 9/1998 | Abraham |
| 5,846,457 | A | 12/1998 | Hoffman |
| 5,917,573 | A | 6/1999 | Davis |
| 5,928,718 | A | 7/1999 | Dillon |
| 5,931,297 | A | 8/1999 | Weill |
| 5,940,153 | A | 8/1999 | Castaneda |
| 5,944,432 | A | 8/1999 | Richardson |
| 6,023,371 | A | 2/2000 | Onitsuka et al. |
| 6,034,866 | A | 3/2000 | Nobuchi |
| 6,068,119 | A | 5/2000 | Derr |
| 6,087,062 | A | 7/2000 | Cunningham et al. |
| 6,089,712 | A | 7/2000 | Harris |
| 6,094,785 | A | 8/2000 | Montgomery |
| 6,132,044 | A | 10/2000 | Sternbergh |
| 6,135,595 | A | 10/2000 | Takeshita et al. |
| 6,142,626 | A | 11/2000 | Lu |
| 6,149,270 | A | 11/2000 | Hayashi |
| 6,265,029 | B1 | 7/2001 | Lewis |
| 6,273,252 | B1 | 8/2001 | Mitchell |
| 6,296,707 | B1 | 10/2001 | Adamczyk et al. |
| 6,399,211 | B2 | 6/2002 | Lewis |
| 6,415,138 | B2 | 7/2002 | Sirola |
| 6,471,056 | B1 | 10/2002 | Tzeng |
| 6,536,589 | B2 | 3/2003 | Chang |
| 6,610,081 | B2 | 8/2003 | Saathoff |
| 6,659,274 | B2 | 12/2003 | Enners |
| 6,698,608 | B2 | 3/2004 | Parker |
| 6,701,159 | B1 | 3/2004 | Powell |
| 6,731,913 | B2 | 5/2004 | Humphreys |
| 6,772,881 | B2 | 8/2004 | Le et al. |
| 6,780,232 | B2 | 8/2004 | Treadway |
| 6,811,258 | B1 | 11/2004 | Grant |
| 6,842,171 | B2 | 1/2005 | Richter |
| 6,887,002 | B1 | 5/2005 | Chen |
| 6,914,774 | B1 | 7/2005 | Albertini |
| 6,995,976 | B2 | 2/2006 | Richardson |
| 7,031,148 | B1 | 4/2006 | Lin |
| 7,037,585 | B2 | 5/2006 | Treadway |
| 7,044,598 | B2 | 5/2006 | Nakada et al. |
| 7,054,441 | B2 | 5/2006 | Pletikosa |
| 7,059,719 | B2 | 6/2006 | Asher |
| 7,145,571 | B2 | 12/2006 | Jones |
| 7,189,489 | B2 | 3/2007 | Kunimoto et al. |
| 7,230,823 | B2 | 6/2007 | Richardson et al. |
| 7,248,904 | B2 | 7/2007 | Gartrell |
| 7,284,856 | B2 | 10/2007 | Duha et al. |
| 7,312,984 | B2 | 12/2007 | Richardson |
| 7,338,704 | B2 | 3/2008 | Decker et al. |
| 7,378,146 | B1 | 5/2008 | Hedrick et al. |
| 7,384,694 | B2 | 6/2008 | Decker et al. |
| 7,495,895 | B2 | 2/2009 | Carnevali |
| 7,514,482 | B2 | 4/2009 | Treadway |
| 7,695,776 | B2 | 4/2010 | Hedrick et al. |
| D619,159 | S | 7/2010 | Finochiaro |
| 7,757,629 | B2 | 7/2010 | Lydon et al. |
| 7,775,659 | B2 | 8/2010 | Nesty |
| 7,916,152 | B2 | 3/2011 | Jones |
| 7,931,369 | B2 | 4/2011 | Harris |
| 7,981,514 | B2 | 7/2011 | Treadway |
| 8,007,901 | B2 | 8/2011 | Beinat et al. |
| 2001/0008278 | A1 | 7/2001 | Yoshimura |
| 2002/0027768 | A1 | 3/2002 | Tseng |
| 2002/0086702 | A1 | 7/2002 | Lai |
| 2002/0101411 | A1 | 8/2002 | Chang |
| 2003/0076474 | A1 | 4/2003 | Wang |
| 2003/0083439 | A1 | 5/2003 | Suzuki |
| 2003/0160754 | A1 | 8/2003 | Hanson |
| 2004/0114242 | A1 | 6/2004 | Sharp |
| 2004/0170924 | A1 | 9/2004 | Kunimoto |
| 2004/0232394 | A1 | 11/2004 | Khan |
| 2005/0017648 | A1 | 1/2005 | Naaman et al. |
| 2005/0094095 | A1 | 5/2005 | Marason |
| 2005/0103424 | A1* | 5/2005 | Nguyen et al. .................. 156/67 |
| 2005/0139498 | A1 | 6/2005 | Goros |
| 2006/0014099 | A1 | 1/2006 | Faler |
| 2006/0083945 | A1* | 4/2006 | Morishita et al. ............. 428/690 |
| 2006/0226040 | A1 | 10/2006 | Medina |
| 2006/0275596 | A1* | 12/2006 | Payne et al. .................... 428/323 |
| 2007/0236656 | A1 | 10/2007 | Jeong |
| 2008/0137030 | A1 | 6/2008 | Hoffman |
| 2008/0213508 | A1 | 9/2008 | Nagasawa et al. |
| 2009/0015786 | A1 | 1/2009 | Harris |
| 2009/0201462 | A1* | 8/2009 | Gruber .......................... 351/163 |
| 2011/0090453 | A1 | 4/2011 | Chen |
| 2011/0176105 | A1 | 7/2011 | Harris |
| 2013/0032758 | A1 | 2/2013 | Harding et al. |
| 2013/0033776 | A1 | 2/2013 | Harding et al. |
| 2013/0056682 | A1 | 3/2013 | Harding et al. |
| 2013/0062564 | A1 | 3/2013 | Harding et al. |
| 2013/0088684 | A1 | 4/2013 | Harding et al. |
| 2013/0100048 | A1 | 4/2013 | Harding et al. |

FOREIGN PATENT DOCUMENTS

| | | |
|---|---|---|
| JP | 9-503402 | 4/1997 |
| JP | 11-225960 | 8/1999 |
| JP | 11-311756 | 11/1999 |
| JP | 2010-157471 A | 7/2010 |
| JP | 2011-222712 A | 11/2011 |
| WO | 95/05621 | 2/1995 |
| WO | 98/02871 | 1/1998 |
| WO | 02/33447 | 4/2002 |
| WO | 2009/011703 | 1/2009 |
| WO | 2012/119158 A1 | 9/2012 |

* cited by examiner

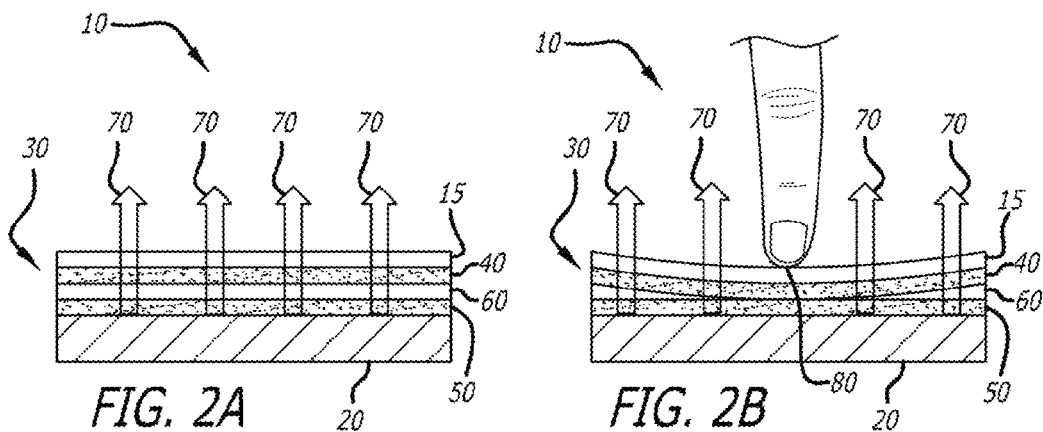
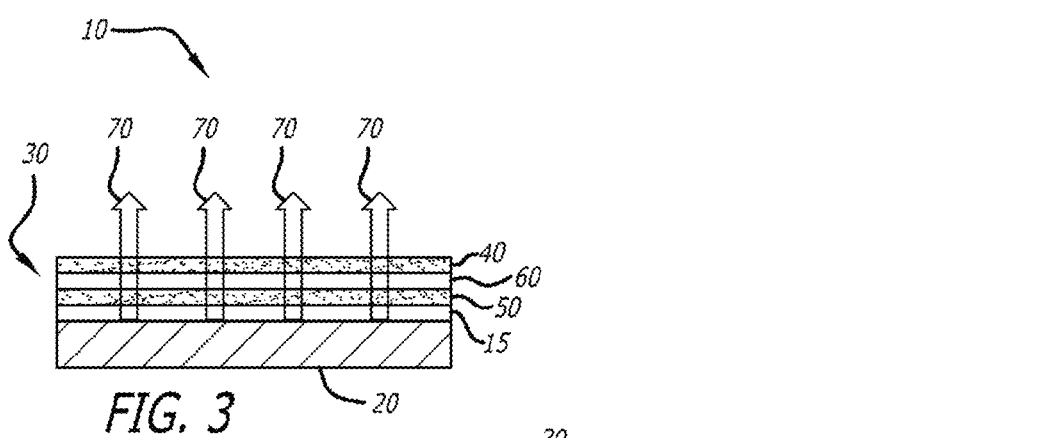
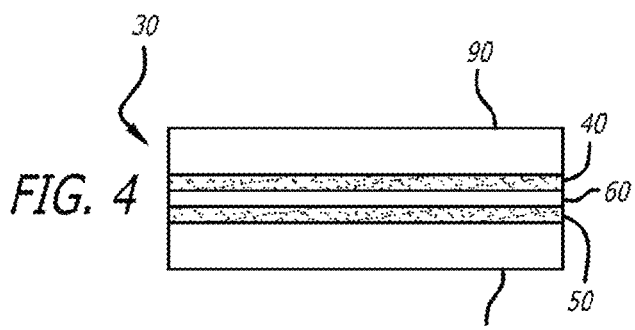
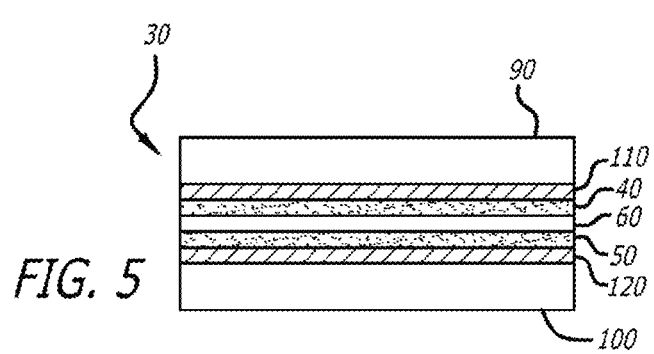

OPTICAL ELEMENT FOR CORRECTING COLOR BLINDNESS

CROSS-REFERENCE TO RELATED APPLICATIONS

This application claims the benefit of Provisional Application No. 61/515,764, filed Aug. 5, 2011, Provisional Application No. 61/544,212, filed Oct. 6, 2011, Provisional Application No. 61/589,136, filed Jan. 20, 2012, and Provisional Application No. 61/677,928, filed Jul. 31, 2012, all of which are incorporated by reference in their entirety herein.

BACKGROUND

1. Field

Some embodiments are related to optical elements for enhancing color discrimination by persons having visual insensitivity between colors, e.g., the correction of colorblindness, which can assist a person or other mammal in distinguishing a first visible color wavelength from a second visible color wavelength.

2. Description of the Related Art

Color blindness is generally recognized as a decreased ability to perceive differences between some of the colors that others can distinguish. Several types of colorblindness exist. A protanomalous individual is less sensitive to red light than normal individuals and thus, suffers from a darkening effect of the red end of the spectrum. A deuteranomalous individual possesses a mutated form of the green pigment, which is shifted towards the red end of the spectrum resulting in a reduction in sensitivity to the green area of the spectrum. Similar to the protanomates, deuteranomates are poor at discriminating small differences in hues in the red, orange, yellow, green region of the spectrum. This red-green colorblindness, which is the most common form of the condition, causes many of these hues to appear shifted towards the red end of the color spectrum. Other colorblind individuals are tritanomalous and possess a mutated form of the blue pigment, which causes a shift towards the green area of the spectrum.

Several methods have been proposed for the correction of colorblindness in human beings. The contents of each of the references discussed below are hereby incorporated herein by reference in their entirety. Generally, options to correct for lack of visual color discrimination include using differential coloration, filtration, and spectral transmission between concurrently used lenses. Other patents disclose associating color with other visual indicators, e.g., cross hatching, as a manner for correcting visual color deficiencies.

SUMMARY

Devices described herein may be used to improve a person's ability to distinguish colors. These devices may be of benefit to both individuals having normal color vision and individuals having an impaired ability to distinguish colors. The present embodiments relate to an optical element useful for enhancing color discrimination by persons having visual insensitivity between colors, e.g., correcting colorblindness, that enhances transmission of one or more desired emissive bandwidths corresponding to a color that a person perceives as difficult to identify or distinguish. The bandwidth can be in the red, yellow, green, or blue region of visible wavelength light. In an embodiment, the optical element can both enhance the transmission of a desired first emissive bandwidth and decrease the transmission of a second emissive bandwidth. For example, a person having colorblindness may be able to perceive a first color, but confuse a second color with the first color. In an embodiment, the optical element can enhance the contrast or intensity between the two colors, increasing their distinction from one another.

An embodiment provides an optical element for improving color discernment, such as correcting visual insensitivity between a first visible color wavelength and a second visible color wavelength. In an embodiment, the optical element comprises a substantially transparent matrix material and a luminescent compound dispersed within the substantially transparent matrix material. In an embodiment, the luminescent compound has an emissive wavelength that substantially overlaps with the first visible color wavelength. In an embodiment, the luminescent compound is present in an amount selected to provide a transmittance that is greater than 100% at the first visible wavelength in the optical element.

Some embodiments include a device for improving color discernment, such as correcting an impaired ability to distinguish colors comprising: an optical element including a luminescent compound dispersed in a matrix material; wherein the optical element is sufficiently transparent to allow a person to see through the optical element; wherein the luminescent compound absorbs light at an absorption wavelength and emits light at an emission wavelength, wherein a human cone photopigment is substantially more sensitive to the emission wavelength than to the absorption wavelength; and wherein the device is configured so that a person, such as a person with an impaired ability to distinguish colors, can better distinguish the colors by viewing an image or an object comprising the colors through the optical element.

Some embodiments include a device for improving ability to distinguish colors comprising: an optical element comprising a luminescent compound dispersed in a matrix material; wherein the optical element is sufficiently transparent to allow a person to see through the optical element; wherein the luminescent compound absorbs light at an absorption wavelength and emits light at an emission wavelength, wherein a human cone photopigment is substantially more sensitive to the emission wavelength than to the absorption wavelength; and wherein the device is configured so that a person, such as a person with normal color vision, can better distinguish the colors by viewing an image or an object comprising the colors through the optical element.

Some embodiments include a device for improving color discernment or correcting an impaired ability to distinguish colors, such as a red-green color deficiency, comprising: an optical element including a luminescent compound in a substantially transparent matrix; and wherein the optical element absorbs light in a wavelength range near peak sensitivity for an M human cone photopigment and emits light of a longer wavelength in a wavelength range near peak sensitivity for an L human cone photopigment.

Some embodiments include a device for improving color discernment or correcting an impaired ability to distinguish colors, such as a red-green color deficiency, comprising: an optical element comprising a luminescent compound dispersed in a matrix material; the optical element is configured to absorb and emit visible light so that when an object or an image is viewed through the optical element, a first color having a first set of color coordinates is converted to a second color having a second set of color coordinates to aid in distinguishing colors; and the distance between the first set of color coordinates and the second set of color coordinates in the direction normal to a color confusion line nearest to the first set of color coordinates is at least about 0.02 color coordinate units.

Some embodiments include a device for improving color discernment or correcting an impaired ability to distinguish colors comprising: an optical element comprising a luminescent compound dispersed in a matrix material; wherein the optical element is sufficiently transparent to allow a person to see through the optical element; wherein the optical element is configured to absorb light of a shorter wavelength and emit light of a longer wavelength, so that a color having a first set of color coordinates is converted to a color having a second set of color coordinates; wherein the distance between the first set of color coordinates and the second set of color coordinates in the direction normal to a color confusion line nearest to the first set of color coordinates is at least about 0.02 color coordinate units; and wherein the device is configured so that a person with an impaired ability to distinguish colors can better distinguish the colors by viewing an image or an object comprising the colors through the optical element.

Some embodiments include a device for improving ability to distinguish colors comprising: an optical element comprising a luminescent compound dispersed in a matrix material; the optical element is configured to absorb and emit visible light so that when an object or an image is viewed through the optical element, a first color having a first set of color coordinates is converted to a second color having a second set of color coordinates to aid in distinguishing colors; and the distance between the first set of color coordinates and the second set of color coordinates is at least about 0.02 color coordinate units.

Some embodiments include a method for preparing a device for improving ability to distinguish colors comprising: selecting a luminescent compound for use in an optical element configured to convert a color having a first set of color coordinates to a color having a second set of color coordinates by absorption and emission of visible light; wherein the luminescent compound is selected so that the distance between the first set of color coordinates and the second set of color coordinates is at least about 0.02 color coordinate units.

Some embodiments include a device for improving the ability to distinguish colors prepared by such a method.

Some embodiments include a device for correcting a vision deficiency related to color discernment including an optical element comprising a composition including a polymer, such as a polymer comprising a polyvinyl alcohol or a derivative thereof, and a rhodamine or a rhodamine derivative.

Some embodiments include methods for preparing a device for correcting an impaired ability to distinguish colors comprising: selecting a luminescent compound for use in an optical element configured to convert a color having a first set of color coordinates to a color having a second set of color coordinates by absorption and emission of visible light; wherein the luminescent compound is selected so that the distance between the first set of color coordinates and the second set of color coordinates in the direction normal to a color confusion line nearest to the first set of color coordinates is at least about 0.02 color coordinate units.

Some embodiments include a device for improving the ability to distinguish colors prepared by such a method.

Some embodiments include an ocular lens comprising: an optical element comprising a luminescent compound in a substantially transparent matrix; wherein the device is configured so that optical element modifies a color of an object or image viewed through the optical element by a user to thereby allow the user to better distinguish colors.

Some embodiments include an electronic device comprising: an electronic display; an optical element comprising a luminescent compound in a substantially transparent matrix; and a touch screen component coupled to the optical element and the electronic display; wherein the touch screen component comprises: a first conductive layer, a second conductive layer, and a spacer between the first conductive layer and the second conductive layer, wherein the first conductive layer and the second conductive layer are substantially transparent; wherein the device is configured so that contact by a user to the touch screen can cause the first conductive layer to contact the second conductive layer to thereby allow current to flow between the first conductive layer and the second conductive layer; wherein the device is configured so that at least a portion of the light emitted from the display passes through the touch screen component and passes through the optical element; wherein the optical element modifies a color of the light emitted from the display that passes through the optical element.

Some embodiments include a device comprising: an optical element comprising a coating, wherein the coating comprises a luminescent compound in a substantially transparent matrix; wherein the device is configured so that the optical element modifies a color of an object or image viewed through the optical element by a user to thereby allow the user to better distinguish colors.

Some embodiments include a device for improving color discernment comprising: an optical element comprising a luminescent compound in a substantially transparent matrix; and wherein the optical element has a peak wavelength of visible absorption of about 540 nm to about 550 nm.

Some embodiments include a composition comprising a polymer and a rhodamine or a rhodamine derivative, wherein the polymer comprises polyvinyl alcohol or a derivative thereof comprising $C_{1-6}$ ester or $C_{1-6}$ acetal pendant groups.

Some embodiments include a method of correcting an impaired ability to distinguish colors comprising positioning a device or an optical element described herein so that an image or an object may be viewed by an individual having the impaired ability to distinguish colors through the optical element.

Some embodiments include a method of improving ability to distinguish colors comprising positioning a device or an optical element describe herein so that an image or an object may be viewed by an individual having normal color vision through the optical element.

Generally, the methods and devices described herein may be used to improve ability to distinguish colors by an individual having an impaired ability to distinguish colors and/or by an individual with normal color vision.

These and other embodiments are described in greater detail below.

BRIEF DESCRIPTION OF THE DRAWINGS

FIGS. 2A and 2B are schematics of some embodiments of a device comprising a touch screen component.

FIG. 3 is a schematic of some embodiments of a device comprising a touch screen component.

FIG. 4 is a schematic of some embodiments of a device comprising a touch screen component.

FIG. 5 is a schematic of some embodiments of a device comprising a touch screen component.

DETAILED DESCRIPTION

Figure 1:
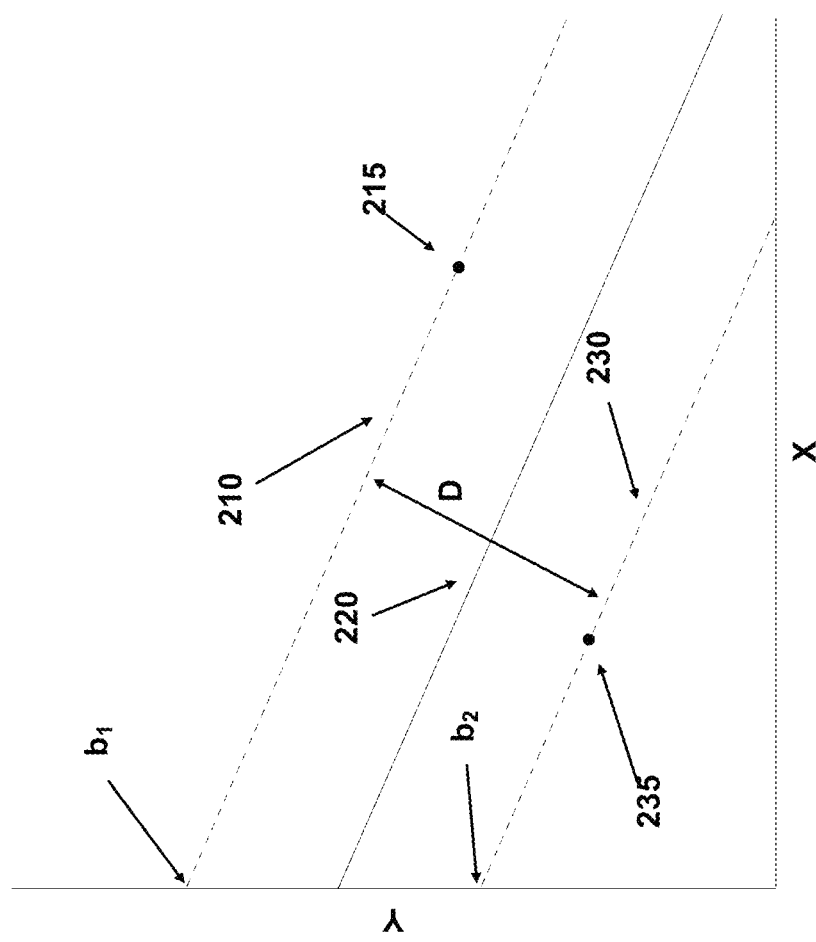
FIG. 1 is a schematic associated with a method for determining the distance between two color coordinates in a direct normal to a color confusion line.

Embodiments of an optical element can correct visual insensitivity between a first visible color wavelength and a second visible color wavelength. In an embodiment, the optical element corrects visual insensitivity by enhancing the transmission in an emissive bandwidth that corresponds to the first visible color wavelength. The first visible color wavelength can be in the red, orange, yellow, green, or blue region of visible wavelength light. In an embodiment, the first visible color wavelength comprises a wavelength that is in the green bandwidth. In an embodiment, the first visible color wavelength is in the range of about 450 nm to about 600 nm, about 500 nm to about 580 nm, or about 520 nm to about 550 nm. In some embodiments, the luminescent compound may provide the enhanced emission in the first visible color wavelength.

The second visible color wavelength can be in the red, yellow, orange, green, or blue region of visible wavelength light. In general, the first visible color wavelength is less than the second visible color wavelength, which means that the first visible color wavelength is shorter, or more blue shifted, than the second visible color wavelength. In an embodiment, the second visible color wavelength comprises a wavelength that is in the red bandwidth. For example, for individuals suffering from a red-green color deficiency, it would be beneficial to increase the perception to green wavelength light, while optionally decreasing the perception to red wavelength light. In an embodiment, the second visible color wavelength is in the range of about 530 nm to about 800 nm, about 560 nm to about 720 nm, about 580 nm to about 710 nm, about 600 nm to about 700 nm, about 530 nm to about 720 nm, about 540 nm to about 710 nm, or about 550 nm to about 700 nm.

The amount of luminescent compound present in the substantially transparent matrix material to form the optical element can vary. Any amount of luminescent compound that increases the emission of the first visible color wavelength, increases the emission of the second visible color wavelength, further separates the peak emissive wavelength of the first color wavelength from the second color wavelength or both increases and separates the peak emissive wavelengths in the optical element, such that the first visible color wavelength is more easily discerned to a colorblind individual, is suitable. In one embodiment, the luminescent compound is present in an amount selected to provide a transmittance that is greater than 90% at the first visible wavelength in the optical element. This is surprising, particularly if the optical element also comprises a light absorbing dye.

The absorbance band of a light absorbing dye may overlap with the emission band of the luminescent compound in this case, resulting in less than 100% transmittance in the green wavelength. In an embodiment, the luminescent compound is present in an amount that provides a transmittance that is greater than 95%, greater than 100%, greater than 101%, greater than 102%, greater than 103%, greater than 104%, or greater than 105%, at the first visible wavelength in the optical element.

In one embodiment, the luminescent compound is present in an amount that shifts and further separates the first peak emissive wavelength at least about 1 nm, 2 nm, 5 nm, or 8 nm relative the second peak emissive wavelength. In one embodiment, the luminescent compound is present in an amount that both increases intensity and shifts and further separates the first peak emissive wavelength by at least 1 nm, 2 nm, 5 nm, or 8 nm relative the second peak emissive wavelength.

The luminescent compound can be present in the substantially transparent matrix material in an amount in the range of about 0.01% to about 30%, about 0.01% to about 20%, about 0.01% to about 15%, about 1% to about 20%, about 1% to about 15%, about 2% to about 12%, about 5% to about 10%, or about 10% by weight, based upon the weight of the composition, or in any amount in a range bounded by, or between, any of these values.

The luminescent dye used in the optical element can vary. In an embodiment, the luminescent compound comprises a perylene derivative dye, such as an optionally substituted perylene; an optionally substituted rhodamine, including optionally optionally substituted rhodamine 110, optionally substituted rhodamine 123, optionally substituted rhodamine 6G, optionally substituted rhodamine 116, optionally substituted rhodamine B, optionally substituted rhodamine 3B, optionally substituted rhodamine 19, etc.; optionally substituted Nile red; optionally substituted fluorescein, including optionally substituted fluorescein isothiocyanate, etc.; optionally substituted 6-FAM phosphoramidite; optionally substituted 4,4-difluoro-4-bora-3a,4a-diaza-s-indacene (BODIPY), including optionally substituted BODIPY FL, optionally substituted BODIPY R6G, optionally substituted BODIPY TMR, optionally substituted BODIPY 630/650, optionally substituted BODIPY TR, optionally substituted BODIPY 630/650, optionally substituted BODIPY 650/665, etc.; optionally substituted coumarin; etc.; optionally substituted pyrromethene 605; or a combination thereof.

Unless otherwise indicated, any reference to a compound herein by structure, name, or any other means, includes salts, including zwitterionic forms; alternate solid forms, such as polymorphs, solvates, hydrates, etc.; tautomers; or any other chemical species that may rapidly convert to a compound described herein under conditions in which the compounds are used as described herein.

Any structure or name for a compound used herein may refer to any stereoisomer or any mixture of stereoisomers.

Unless otherwise indicated, when a compound or chemical structural feature such as alkyl, cycloalkyl, alkoxy, alkoxyalkyl, aryl, arylalkyl, perylene, etc., is referred to as being "optionally substituted," it includes a feature that has no substituents (i.e. "unsubstituted"), or a feature that is "substituted," meaning that the feature has one or more substituents. The term "substituent" has the ordinary meaning known to one of ordinary skill in the art, and includes a moiety that replaces one or more hydrogen atoms attached to a parent compound or structural feature. In some embodiments, the substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mo-1.15 g/mol to 200 g/mol, 15 g/mol to 300 g/mol, or 15 g/mol to 500 g/mol. In some embodiments, the substituent comprises: 0-30, 0-20, 0-10, or 0-5 carbon atoms; and 0-30, 0-20, 0-10, or 0-5 heteroatoms independently selected from: N, O, S, Si, F, Cl, Br, or I; provided that the substituent comprises at least one atom selected from: C, N, O, S, Si, F, Cl, Br, or I. In some embodiments, a substituent may consist of 1, 2, 3, 4, 5, 6, 7, 8, 9, 10, 11, or 12 non-hydrogen atoms and any necessary hydrogen atoms. Some non-hydrogen atoms may include C, N, O, S, Si, F, Cl, Br, I, P, etc.

Examples of substituents include, but are not limited to, alkyl (including linear, branched, and cycloalkyl), alkenyl (including linear, branched, and cycloalkenyl), alkynyl (including linear, branched, and cyclo alkynyl), heteroalkyl, heteroalkenyl, heteroalkynyl, aryl, heterocyclic substituents (including heteroaryl and heteroalicyclic substituents), hydroxy, protected hydroxy, alkoxy, aryloxy, acyl, acyloxy, alkylcarboxylate, carboxylate, thiol, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, and amino, including mono- and di-substituted amino groups, and the protected derivatives thereof, etc., or a combination thereof. The term "combination thereof" in the previous list indicates that substituents may also include a combination of any of the above substituents, wherein a hydrogen atom of one substituent is replaced by another substituent. For example, substituents may be a combination of alkyl and aryl (e.g. arylalkyl such as $CH_2$-phenyl, or heteroarylalkyl such as $C_2H_4$-heteroaryl, etc.), alkyl and a heterocyclic substituent (e.g. heterocyclylalkyl), alkyl and alkoxy (e.g. $CH_2OCH_3$), alkyl and halo (e.g. $C_2H_4Cl$, $C_3H_6F$, etc.), acyl and hydroxyl (e.g. —$COCH_2OH$), etc.

For convenience, the term "molecular weight" is used with respect to a moiety or part of a molecule to indicate the sum of the atomic masses of the atoms in the moiety or part of a molecule, even though it may not be a complete molecule. "Molecular weight" may also refer to complete molecules.

Structures associated with some of the chemical names referred to herein are depicted below. These structures may be unsubstituted, as shown below, or a substituent may independently be in any position normally occupied by a hydrogen atom when the structure is unsubstituted.

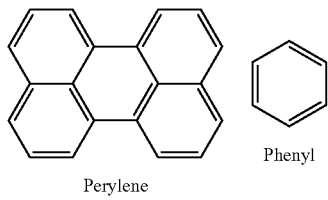

Perylene     Phenyl

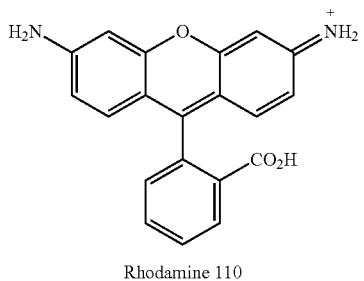

Rhodamine 110

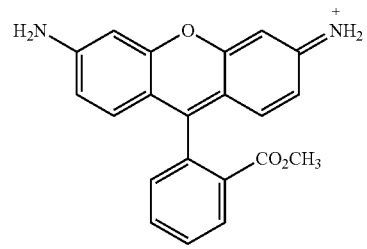

Rhodamine 123

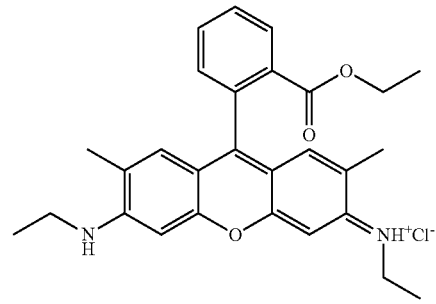

Rhodamine 6G

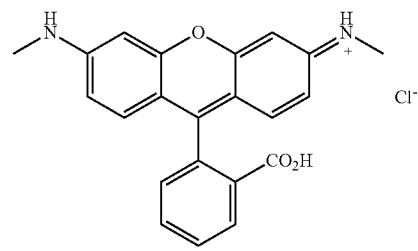

Rhodamine 116

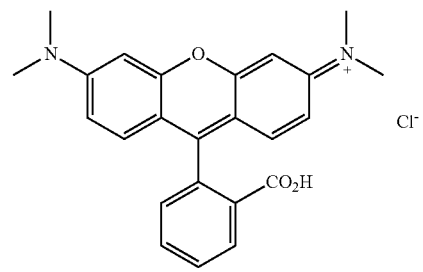

Rhodamine B

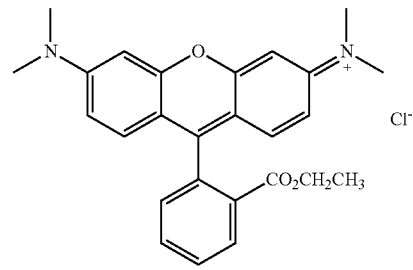

Rhodamine 3B

-continued
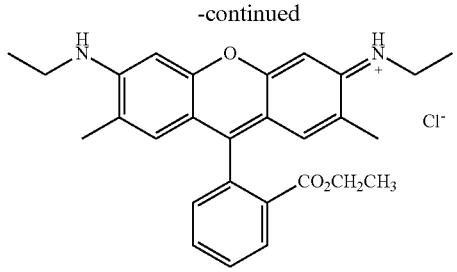
Rhodamine 19
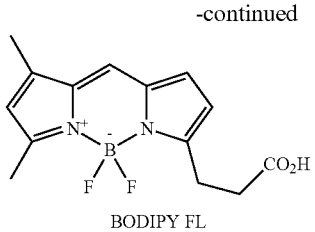
BODIPY FL
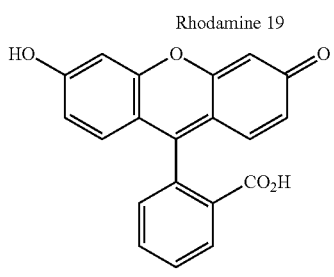
Fluorescein
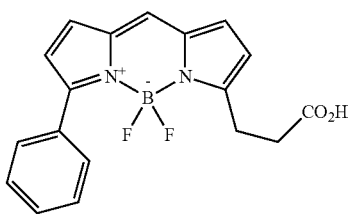
BODIPY R6G
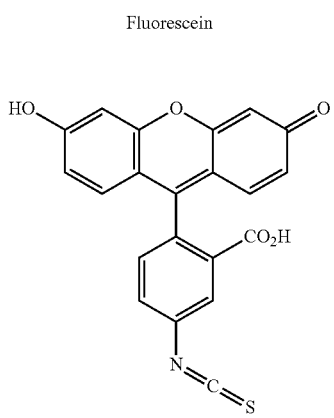
Fluorescein isothiocyanate
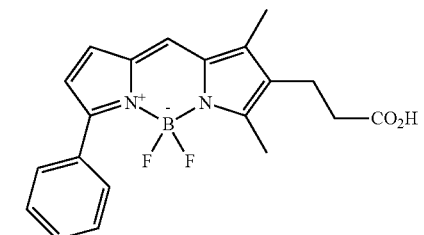
BODIPY TMR
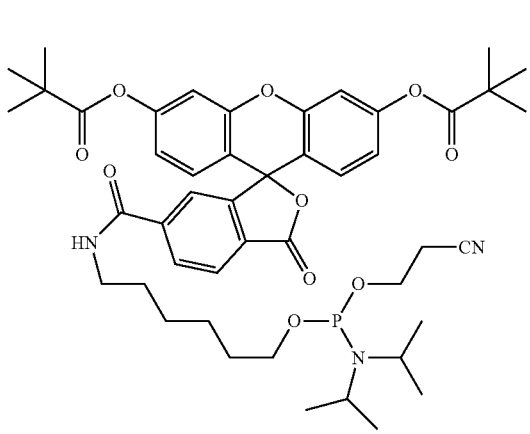
6-FAM phosphoramidite
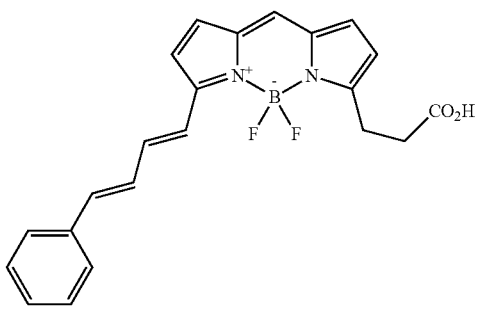
BODIPY 581/591
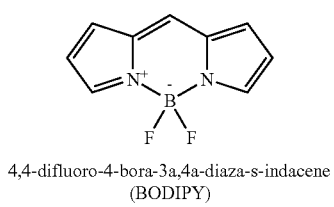
4,4-difluoro-4-bora-3a,4a-diaza-s-indacene
(BODIPY)
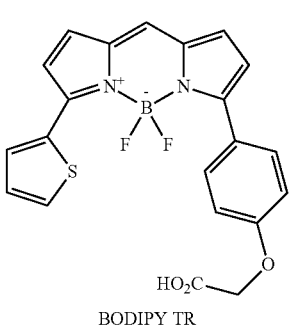
BODIPY TR

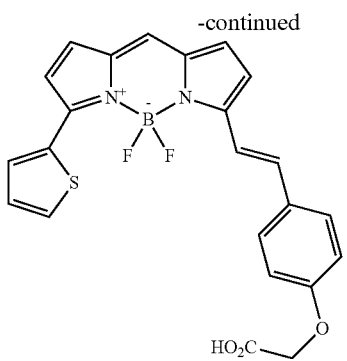

BODIPY 630/650

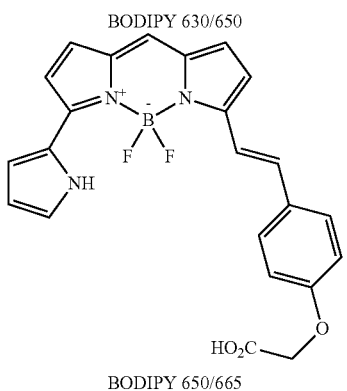

BODIPY 650/665

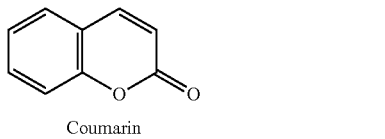

Coumarin

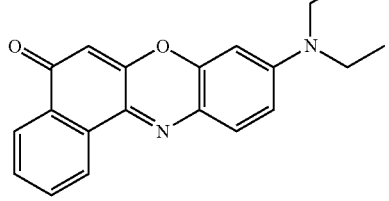

Nile Red

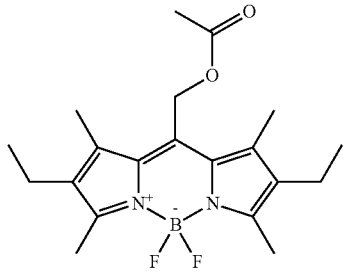

Pyrromethene 605

Unless a point of attachment is indicated by —|, attachment may occur at any position normally occupied by a hydrogen atom.

As used herein the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. iso-propyl), $C_4H_5$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_5$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like. In some embodiments, and alkyl group may include methyl, ethyl, n-propyl, isopropyl, n-butyl, isobutyl, sec-butyl, tert-butyl, isohexyl, isooctyl, 2-ethyl-hexyl, etc.

An alkoxy group may also be linear, branched, or cyclic. Some examples of useful alkoxy groups include methoxy, ethoxy, propoxy, and butoxy. An alkoxyalkyl group may also be linear or branched. Some examples of useful alkoxyalkyl groups include methoxymethyl, methoxyethyl, methoxypropyl, ethoxymethyl, ethoxyethyl, ethoxypropyl, propoxymethyl, propoxyethyl, and propoxypropyl.

Some examples of useful cycloalkyl groups include cyclopentyl, cyclohexyl, or cycloheptyl. Some examples of useful aryl groups include phenyl, diphenyl, tolyl, naphthyl, phenanthryl, and anthracenyl. Some examples of useful arylalkyl groups include benzyl, phenethyl, diphenylmethyl, trityl, naphthylmethyl, phenanthylmethyl, and anthranylmethyl.

Some optionally substituted perylenes may be represented by Formula 1:

$$Ph^1\text{-}Per\text{-}Ph^2 \quad \text{Formula 1}$$

With respect to Formula 1, $Ph^1$ may be optionally substituted phenyl. If the phenyl is substituted, it may have 1, 2, 3, 4, or 5 substituents. Any substituent may be included on the phenyl. In some embodiments, some or all of the substituents on the phenyl may have: from 0 to 12 carbon atoms and from 0 to 5 heteroatoms independently selected from: O, N, S, F, Cl, Br, and I (provided that there is at least non-hydrogen atom); and/or a molecular weight of 15 g/mol to 250 g/mol or about 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{10}$ alkoxy such as —$OCH_3$, —$OC_2H_5$, —$OC_3H_7$, cyclic —$OC_3H_5$, —$OC_4H_9$, cyclic —$OC_4H_7$, —$OC_5H_{11}$, cyclic —$OC_5H_9$, —$OC_6H_{13}$, cyclic —$OC_6H_{11}$, etc.; halo, such as F, Cl, Br, I; OH; CN; $NO_2$; fluoroalkyl, such as $CF_3$, $CF_2H$, $O_2F_5$, etc.; a $C_{1-10}$ ester such as —$O_2CCH_3$, -$CO_2CH_3$, —$O_2CC_2H_5$, —$CO_2C_2H_5$, —$O_2C$-phenyl, —$CO_2$-phenyl, etc.; a $C_{1-10}$ amide such as —$CONH_2$, —$CONHCH_3$, —NHCO-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, the phenyl is optionally substituted with 1 or 2 substituents independently selected from $C_{1-6}$ alkyl, $CF_3$, and F. In some embodiments, the phenyl has a $CF_3$ substituent and is otherwise unsubstituted.

With respect to Formula 1, $Ph^2$ may be optionally substituted phenyl. If the phenyl is substituted, it may have 1, 2, 3, 4, or 5 substituents. Any substituent may be included on the phenyl. In some embodiments, some or all of the substituents on the phenyl may have: from 0 to 12 carbon atoms and from 0 to 5 heteroatoms independently selected from: O, N, S, F, Cl, Br, and I (provided that there is at least 1 non-hydrogen atom); and/or a molecular weight of 15 g/mol to 250 g/mol or about 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{10}$ alkoxy such as $-OCH_3$, $-OC_2H_5$, $-OC_3H_7$, cyclic $-OC_3H_5$, $-OC_4H_9$, cyclic $-OC_4H_7$, $-OC_5H_{11}$, cyclic $-OC_5H_9$, $-OC_6H_{13}$, cyclic $-OC_6H_{11}$, etc.; halo, such as F, Cl, Br, I; OH; CN; $NO_2$; fluoroalkyl, such as $CF_3$, $CF_2H$, $O_2F_5$, etc.; a $C_{1-10}$ ester such as $-O_2CCH_3$, $-CO_2CH_3$, $-O_2CC_2H_5$, $-CO_2C_2H_5$, $-O_2C$-phenyl, $-CO_2$-phenyl, etc.; a $C_{1-10}$ amide such as $-CONH_2$, $-CONHCH_3$, $-NHCO$-phenyl, etc.; a $C_{1-10}$ ketone such as $-COCH_3$, $-COC_2H_5$, $-COC_3H_7$, $-CO$-phenyl, etc.; or a $C_{1-10}$ amine such as $NH_2$, $NH(CH_3)$, $N(CH_3)_2$, $N(CH_3)C_2H_5$, etc. In some embodiments, the phenyl is optionally substituted with 1 or 2 substituents independently selected from $C_{1-6}$ alkyl, $CF_3$, and F. In some embodiments, the phenyl has a $CF_3$ substituent and is otherwise unsubstituted.

With respect to Formula 1, Per may be optionally substituted perylene. If the perylene is substituted, it may have 1, 2, 3, 4, 5, 6, 7, 8, 9, or 10 substituents. Any substituent may be included on the perylene. In some embodiments, some or all of the substituents on the perylene may have: from 0 to 12 carbon atoms and from 0 to 5 heteroatoms independently selected from: O, N, S, F, Cl, Br, and I (provided that there is at least non-hydrogen atom); and/or a molecular weight of 15 g/mol to 250 g/mol or about 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{10}$ alkoxy such as $-OCH_3$, $-OC_2H_5$, $-OC_3H_7$, cyclic $-OC_3H_5$, $-OC_4H_9$, cyclic $-OC_4H_7$, $-OC_5H_{11}$, cyclic $-OC_5H_9$, $-OC_6H_{13}$, cyclic $-OC_6H_{11}$, etc.; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as $-O_2CCH_3$, $-CO_2CH_3$, $-O_2CC_2H_5$, $-CO_2C_2H_5$, $-O_2C$-phenyl, $-CO_2$-phenyl, etc.; a $C_{1-10}$ amide such as $-CONH_2$, $-CONHCH_3$, $-NHCO$-phenyl, etc.; a $C_{1-10}$ ketone such as $-COCH_3$, $-COC_2H_5$, $-COC_3H_7$, $-CO$-phenyl, etc.; or a $C_{1-10}$ amine such as $NH_2$, $NH(CH_3)$, $N(CH_3)_2$, $N(CH_3)C_2H_5$, etc. In some embodiments, the perylene is optionally substituted with 1 or 2 substituents independently selected from $C_{1-6}$ alkyl, $CF_3$, and F. In some embodiments, Per is unsubstituted.

Some optionally substituted perylenes may be represented by any of Formulas 2-7:

Formula 2

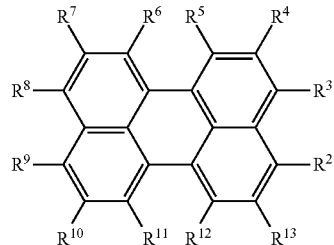

Formula 3

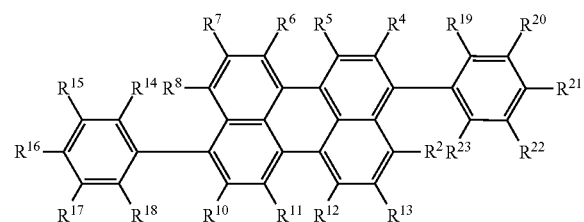

Formula 4

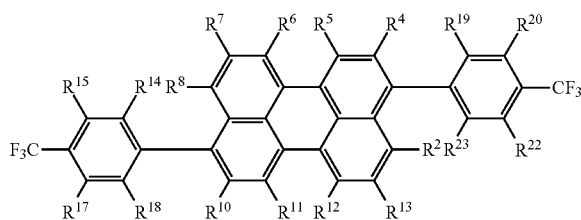

Formula 5

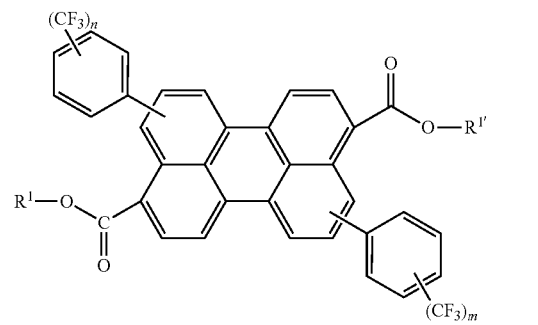

Formula 6

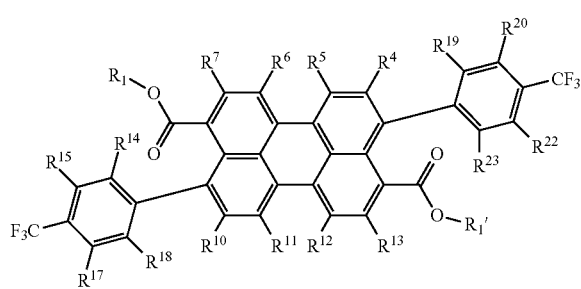

Formula 7

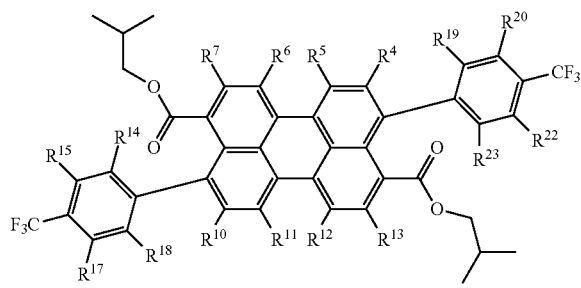

Generally $R^2$-$R^{23}$, may be H or any substituent, such as a substituent having from 0 to 12 carbon atoms and from 0 to 5 heteroatoms independently selected from: O, N, S, F, Cl, Br, and I, and/or having a molecular weight of 15 g/mol to 300 g/mol. In some embodiments, $R^2$-$R^{23}$ may have 1, 2, 3, 4, 5, 6, 7, 8, 9, or 10 carbon atoms, and 0, 1, or 2 oxygen atoms, 0 or 1 nitrogen atoms, and/or 0 or 1 sulfur atoms. Any of $R^2$-$R^{23}$ may comprise: a) 1 or more alkyl moieties, aryl moieties, and/or heteroaryl moieties, optionally substituted with, or optionally connected by or to, b) 1 or more functional groups, such as C=C, C≡C, CO, $CO_2$, CON, $NCO_2$, OH, SH, O, S, N, N=C, F, Cl, Br, I, CN, $NO_2$, $CO_2H$, $NH_2$, etc.; or may be a substituent having no alkyl portion, such as F, Cl, Br, I, $NO_2$, CN, $NH_2$, OH, COH, $CO_2H$, etc.

With respect to any relevant formula or structural depiction above, some non-limiting examples of $R^2$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^2$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^2$ may be H. In some embodiments, $R^2$ is $CO_2R^A$.

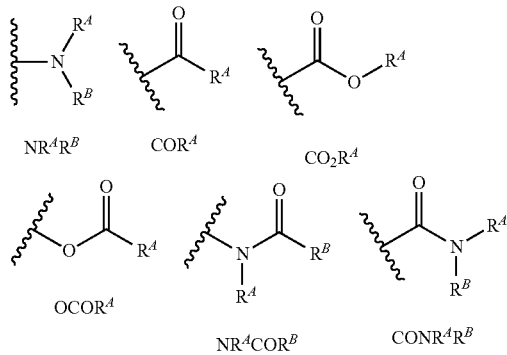

$NR^AR^B$  $COR^A$  $CO_2R^A$  $OCOR^A$  $NR^ACOR^B$  $CONR^AR^B$

Each $R^A$ in any formula or structural depiction herein may independently be H, or $C_{1-12}$ alkyl, including: linear or branched alkyl having a formula $C_aH_{a+1}$, or cycloalkyl having a formula $C_aH_{a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc.

Each $R^B$ in any formula or structural depiction herein may independently be H, or $C_{1-12}$ alkyl, including: linear or branched alkyl having a formula $C_aH_{a+1}$, or cycloalkyl having a formula $C_aH_a$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_8H_{17}$, $C_7H_{15}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc.

With respect to any relevant formula or structural depiction above, some non-limiting examples of $R^3$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^3$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^3$ may be H.

With respect to any relevant formula or structural depiction above, some non-limiting examples of $R^4$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^4$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^4$ may be H.

With respect to any relevant formula or structural depiction above, some non-limiting examples of $R^5$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^5$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^5$ may be H.

With respect to any relevant formula or structural depiction above, such as Formula 1, in some embodiments, one of $R^3$, $R^4$, and $R^5$ is optionally substituted phenyl, and the other two of $R^3$, $R^4$, and $R^5$ are not phenyl. If the phenyl is substituted, it may have 1, 2, 3, 4, or 5 substituents. Any substituent may be included on the phenyl. In some embodiments, some or all of the substituents on the phenyl may have: from 0 to 12 carbon atoms and from 0 to 5 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-10}$ fluoroalkyl, such as $CF_3$, $CF_2H$, $O_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ amide such as —$CONH_2$, —$CONHCH_3$, —NHCO-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, the phenyl is optionally substituted with 1 or 2 substituents independently selected from $C_{1-6}$ alkyl, $CF_3$, and F. In some embodiments, the phenyl has a $CF_3$ substituent and is otherwise unsubstituted.

With respect to any relevant formula or structural depiction above, some non-limiting examples of $R^6$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^6$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^6$ may be H.

With respect to any relevant formula or structural depiction above, some non-limiting examples of $R^7$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^7$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^7$ may be H.

With respect to any relevant formula or structural depiction above, some non-limiting examples of $R^8$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^5$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.;

or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^8$ may be H. In some embodiments, $R^8$ is $CO_2R^A$.

With respect to any relevant formula or structural depiction above, some non-limiting examples of $R^9$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^9$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of O-butyl, isomers of —O-cyclobutyl, isomers of —O-pentyl, isomers of —O-cyclopentyl, isomers of —O-hexyl, isomers of —O-cyclohexyl, etc. In some embodiments, $R^9$ may be H.

With respect to any relevant formula or structural depiction above, some non-limiting examples of $R^{10}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{10}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{10}$ may be H.

With respect to any relevant formula or structural depiction above, some non-limiting examples of $R^{11}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{11}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{11}$ may be H.

With respect to any relevant formula or structural depiction above, such as Formula 1, in some embodiments, one of $R^9$, $R^{10}$, and $R^{11}$ is optionally substituted phenyl, and the other two of $R^9$, $R^{10}$, and $R^{11}$ are not phenyl. If the phenyl is substituted, it may have 1, 2, 3, 4, or 5 substituents. Any substituent may be included on the phenyl. In some embodiments, some or all of the substituents on the phenyl may have: from 0 to 12 carbon atoms and from 0 to 5 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$; $O_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ amide such as —$CONH_2$, —$CONHCH_3$, —NHCO-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, the phenyl is optionally substituted with 1 or 2 substituents independently selected from $C_{1-6}$ alkyl, $CF_3$, and F. In some embodiments, the phenyl has a $CF_3$ substituent and is otherwise unsubstituted.

With respect to any relevant formula or structural depiction above, some non-limiting examples of $R^{12}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{12}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{12}$ may be H.

With respect to any relevant formula or structural depiction above, some non-limiting examples of $R^{13}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{13}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{13}$ may be H.

With respect to any relevant formula or structural depiction above, some non-limiting examples of $R^{14}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{14}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{14}$ may be H.

With respect to any relevant formula or structural depiction above, some non-limiting examples of $R^{15}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{15}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{15}$ may be H.

With respect to any relevant formula or structural depiction above, some non-limiting examples of $R^{16}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{16}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{16}$ may be H.

With respect to any relevant formula or structural depiction above, some non-limiting examples of $R^{17}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{17}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.;

or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{17}$ may be H.

With respect to any relevant formula or structural depiction above, some non-limiting examples of $R^{18}$ may include $R^A$, F, Cl, CN, $OR^A$, $CF_3$, $NO_2$, $NR^A R^B$, $COR^A$, $CO_2 R^A$, $OCOR^A$, $NR^A COR^B$, $CONR^A R^B$, etc. In some embodiments, $R^{18}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{18}$ may be H.

With respect to any relevant formula or structural depiction above, some non-limiting examples of $R^{19}$ may include $R^A$, F, Cl, CN, $OR^A$, $CF_3$, $NO_2$, $NR^A R^B$, $COR^A$, $CO_2 R^A$, $OCOR^A$, $NR^A COR^B$, $CONR^A R^B$, etc. In some embodiments, $R^{19}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{19}$ may be H.

With respect to any relevant formula or structural depiction above, some non-limiting examples of $R^{20}$ may include $R^A$, F, Cl, CN, $OR^A$, $CF_3$, $NO_2$, $NR^A R^B$, $COR^A$, $CO_2 R^A$, $OCOR^A$, $NR^A COR^B$, $CONR^A R^B$, etc. In some embodiments, $R^{20}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of O-butyl, isomers of —O-cyclobutyl, isomers of —O-pentyl, isomers of —O-cyclopentyl, isomers of —O-hexyl, isomers of —O-cyclohexyl, etc. In some embodiments, $R^{20}$ may be H.

With respect to any relevant formula or structural depiction above, some non-limiting examples of $R^{21}$ may include $R^A$, F, Cl, CN, $OR^A$, $CF_3$, $NO_2$, $NR^A R^B$, $COR^A$, $CO_2 R^A$, $OCOR^A$, $NR^A COR^B$, $CONR^A R^B$, etc. In some embodiments, $R^{21}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{21}$ may be H.

With respect to any relevant formula or structural depiction above, some non-limiting examples of $R^{22}$ may include $R^A$, F, Cl, CN, $OR^A$, $CF_3$, $NO_2$, $NR^A R^B$, $COR^A$, $CO_2 R^A$, $OCOR^A$, $NR^A COR^B$, $CONR^A R^B$, etc. In some embodiments, $R^{22}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{22}$ may be H.

With respect to any relevant formula or structural depiction above, some non-limiting examples of $R^{23}$ may include $R^A$, F, Cl, CN, $OR^A$, $CF_3$, $NO_2$, $NR^A R^B$, $COR^A$, $CO_2 R^A$, $OCOR^A$, $NR^A COR^B$, $CONR^A R^B$, etc. In some embodiments, $R^{23}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{23}$ may be H.

With respect to any relevant formula or structural depiction above, such as Formula 5 or Formula 6, $R^1$ may be hydrogen; $C_1$-$C_{10}$ alkyl, including linear and branched alkyl such as $CH_3$, $C_2H_5$, $C_3H_7$, $C_4H_9$, $C_5H_{11}$, $C_6H_{13}$, etc, and $C_3$-$C_{10}$ cycloalkyl such as $C_3H_5$, $C_4H_7$, $C_5H_9$, $C_6H_{11}$, etc.; $C_2$-$C_{10}$ alkoxyalkyl; $C_6$-$C_{18}$ aryl, such as optionally substituted phenyl, optionally substituted naphthyl, etc.; and $C_6$-$C_{20}$ arylalkyl, such as optionally substituted benzyl, optionally substituted diphenylmethyl, trityl, etc. In some embodiments, $R^1$ may be isopropyl, isobutyl, isohexyl, isooctyl, 2-ethyl-hexyl, diphenylmethyl, trityl, or diphenyl.

With respect to any relevant formula or structural depiction above, such as Formula 5 or Formula 6, $R^{1'}$ may be hydrogen; $C_1$-$C_{10}$ alkyl, including linear and branched alkyl such as $CH_3$, $C_2H_5$, $C_3H_7$, $C_4H_9$, $C_5H_{11}$, $C_6H_{13}$, etc, and $C_3$-$C_{10}$ cycloalkyl such as $C_3H_5$, $C_4H_7$, $C_5H_9$, $C_6H_{11}$, etc.; $C_2$-$C_{10}$ alkoxyalkyl; $C_6$-$C_{18}$ aryl, such as optionally substituted phenyl, optionally substituted naphthyl, etc.; and $C_6$-$C_{20}$ arylalkyl, such as optionally substituted benzyl, optionally substituted diphenylmethyl, trityl, etc. In some embodiments, $R^{1'}$ may be isopropyl, isobutyl, isohexyl, isooctyl, 2-ethyl-hexyl, diphenylmethyl, trityl, or diphenyl.

With respect to any relevant formula or structural depiction above, such as Formula 5, m may be 1, 2, 3, 4, or 5. In some embodiments, m is 1, 2, 3, or 4.

With respect to any relevant formula or structural depiction above, such as Formula 5, n may be 1, 2, 3, 4, or 5. In some embodiments, n is 1, 2, 3, or 4.

In some embodiments, $R^1$ and $R^{1'}$ are each independently hydrogen, $C_1$-$C_6$ alkyl, $C_2$-$C_6$ alkoxyalkyl and $C_6$-$C_{18}$ aryl, or $C_6$-$C_{20}$ arylalkyl. The alkyl and alkoxyalkyl groups may be branched, linear, or cyclic. Some non-limiting examples include isopropyl, isobutyl, isohexyl, isooctyl, 2-ethyl-hexyl. Some non-limiting examples of aryl and arylalkyl groups include diphenylmethyl, trityl, and diphenyl.

In an embodiment, the luminescent compound comprises diisobutyl 4,10-bis(4-(trifluoromethyl)phenyl)perylene-3,9-dicarboxylate (Green-1):

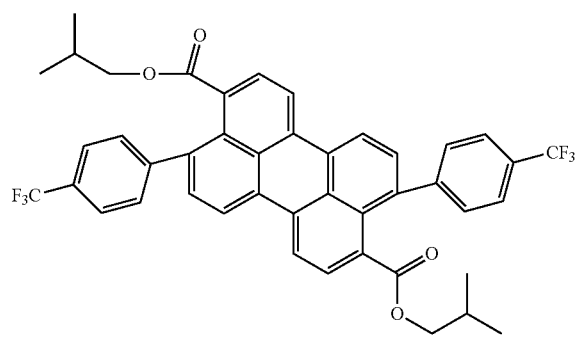 [SMILES: CC(C)COC(=O)c1ccc2c3ccc(-c4ccc(C(F)(F)F)cc4)c4c(C(=O)OCC(C)C)ccc(c5ccc(-c6ccc(C(F)(F)F)cc6)c1c25)c43]

In some embodiments, a luminescent compound may be an optionally substituted rhodamine or a rhodamine derivative, such as a compound of any of Formula 8, Formula 9, or Formula 10:

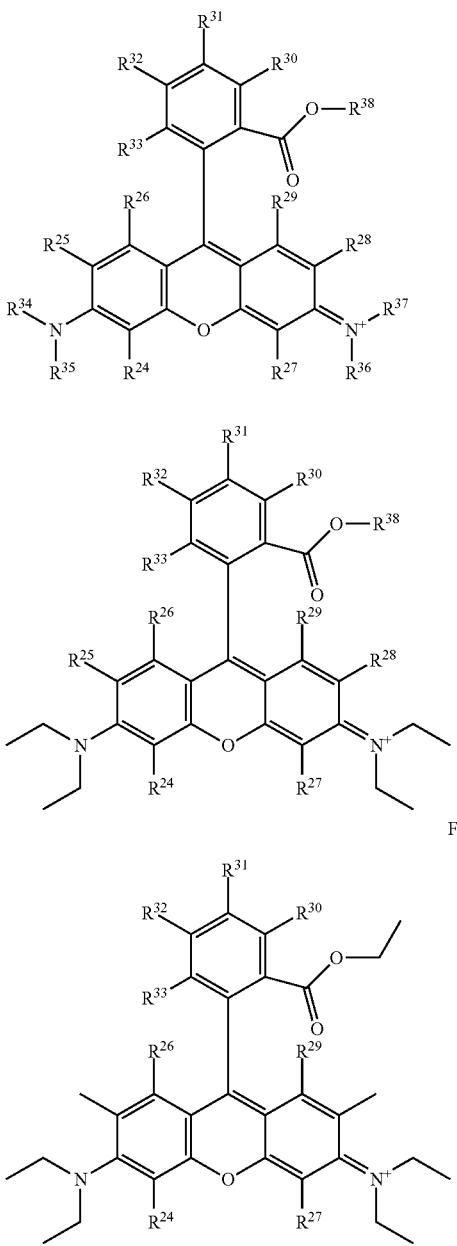

Formula 8

Formula 9

Formula 10

Generally $R^{24}$-$R^{38}$, may be H or any substituent, such as a substituent having from 0 to 6 carbon atoms and from 0 to 5 heteroatoms independently selected from: O, N, S, F, Cl, Br, and I, and/or having a molecular weight of 15 g/mol to 300 g/mol. In some embodiments, $R^{24}$-$R^{38}$ may have 1, 2, 3, 4, 5, 6, 7, 8, 9, or 10 carbon atoms, 0 or 1 nitrogen atoms, and/or 0 or 1 sulfur atoms. Any of $R^{24}$-$R^{38}$ may comprise: a) 1 or more alkyl moieties optionally substituted with, or optionally connected by or to, b) 1 or more functional groups, such as C=C, C≡C, CO, $CO_2$, CON, $NCO_2$, OH, SH, O, S, N, N=C, F, Cl, Br, I, CN, $NO_2$, $CO_2H$, $NH_2$, etc.; or may be substituent having no alkyl portion, such as F, Cl, Br, I, $NO_2$, CN, $NH_2$, OH, COH, $CO_2H$, etc.

With respect to any relevant formula or structural depiction above, some non-limiting examples of $R^{24}$ may include $R^A$, F, Cl, CN, $OR^A$, $CF_3$, $NO_2$, $NR^A R^B$, $COR^A$, $CO_2 R^A$, $OCOR^A$, $NR^A COR^B$, $CONR^A R^B$, etc. In some embodiments, $R^{24}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of O-butyl, isomers of —O-cyclobutyl, isomers of —O-pentyl, isomers of —O-cyclopentyl, isomers of —O-hexyl, isomers of —O-cyclohexyl, etc. In some embodiments, $R^{24}$ may be H.

With respect to any relevant formula or structural depiction above, some non-limiting examples of $R^{25}$ may include $R^A$, F, Cl, CN, $OR^A$, $CF_3$, $NO_2$, $NR^A R^B$, $COR^A$, $CO_2 R^A$, $OCOR^A$, $NR^A COR^B$, $CONR^A R^B$, etc. In some embodiments, $R^{25}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{25}$ may be H or $CH_3$.

With respect to any relevant formula or structural depiction above, some non-limiting examples of $R^{26}$ may include $R^A$, F, Cl, CN, $OR^A$, $CF_3$, $NO_2$, $NR^A R^B$, $COR^A$, $CO_2 R^A$, $OCOR^A$, $NR^A COR^B$, $CONR^A R^B$, etc. In some embodiments, $R^{26}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{26}$ may be H.

With respect to any relevant formula or structural depiction above, some non-limiting examples of $R^{27}$ may include $R^A$, F, Cl, CN, $OR^A$, $CF_3$, $NO_2$, $NR^A R^B$, $COR^A$, $CO_2 R^A$, $OCOR^A$, $NR^A COR^B$, $CONR^A R^B$, etc. In some embodiments, $R^{27}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{27}$ may be H.

With respect to any relevant formula or structural depiction above, some non-limiting examples of $R^{28}$ may include $R^A$, F, Cl, CN, $OR^A$, $CF_3$, $NO_2$, $NR^A R^B$, $COR^A$, $CO_2 R^A$, $OCOR^A$, $NR^A COR^B$, $CONR^A R^B$, etc. In some embodiments, $R^{28}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{28}$ may be H or $CH_3$.

In some embodiments both $R^{25}$ and $R^{28}$ may be H or both $R^{25}$ and $R^{28}$ may be $CH_3$.

With respect to any relevant formula or structural depiction above, some non-limiting examples of $R^{29}$ may include $R^A$, F, Cl, CN, $OR^A$, $CF_3$, $NO_2$, $NR^A R^B$, $COR^A$, $CO_2 R^A$, $OCOR^A$, $NR^A COR^B$, $CONR^A R^B$, etc. In some embodiments, $R^{29}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{29}$ may be H.

With respect to any relevant formula or structural depiction above, some non-limiting examples of $R^{30}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{30}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{30}$ may be H.

With respect to any relevant formula or structural depiction above, some non-limiting examples of $R^{31}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{31}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{31}$ may be H.

With respect to any relevant formula or structural depiction above, some non-limiting examples of $R^{32}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{32}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{32}$ may be H.

With respect to any relevant formula or structural depiction above, some non-limiting examples of $R^{33}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{33}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{33}$ may be H.

With respect to any relevant formula or structural depiction above, some non-limiting examples of $R^{34}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{34}$ may be H or $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{34}$ may be H; $CH_3$, or $CH_2CH_3$.

With respect to any relevant formula or structural depiction above, some non-limiting examples of $R^{35}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{35}$ may be H or $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{35}$ may be H, $CH_3$, or $CH_2CH_3$.

In some embodiments, $R^{34}$ and $R^{35}$ are both H or $CH_3$, or $R^{34}$ is H and $R^{35}$ is $CH_3$ or $CH_2CH_3$.

With respect to any relevant formula or structural depiction above, some non-limiting examples of $R^{36}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{36}$ may be H or $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{36}$ may be H, $CH_3$, or $CH_2CH_3$.

With respect to any relevant formula or structural depiction above, some non-limiting examples of $R^{37}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{37}$ may be H or $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{37}$ may be H, $CH_3$, or $CH_2CH_3$.

In some embodiments, $R^{36}$ and $R^{37}$ are both H or $CH_3$, or $R^{36}$ is H and $R^{37}$ is $CH_3$ or $CH_2CH_3$.

With respect to any relevant formula or structural depiction above, some non-limiting examples of $R^{38}$ may include $R^A$. In some embodiments, $R^{38}$ may be H or $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc. In some embodiments, $R^{38}$ may be H, $CH_3$, or $CH_2CH_3$.

Some luminescent compounds may be an optionally substituted BODIPY or BODIPY derivative, such as a compound of any of Formula 11, Formula 12, Formula 13, Formula 14, or Formula 15:

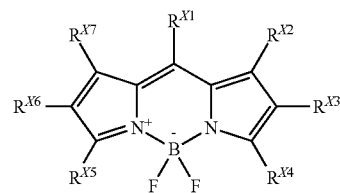

Formula 11

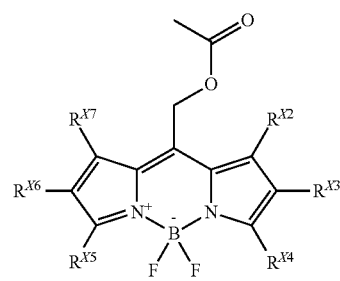

Formula 12

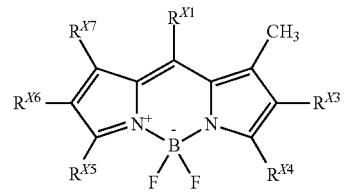

Formula 13

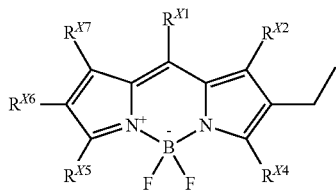

Formula 14

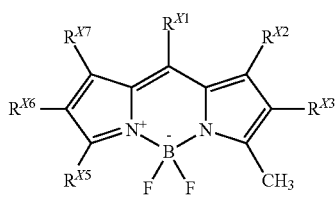

Formula 15

Generally $R^{X1}$-$R^{X7}$, may be H or any substituent, such as a substituent having from 0 to 6 carbon atoms and from 0 to 5 heteroatoms independently selected from: O, N, S, F, Cl, Br, and I, and/or having a molecular weight of 15 g/mol to 300 g/mol. In some embodiments $R^{X1}$-$R^{X7}$ may have 1, 2, 3, 4, 5, 6, 7, 8, 9, or 10 carbon atoms, 0 or 1 nitrogen atoms, and/or 0 or 1 sulfur atoms. Any of $R^{X1}$-$R^{X7}$ may comprise: a) 1 or more alkyl moieties optionally substituted with, or optionally connected by or to, b) 1 or more functional groups, such as C=C, C≡C, CO, $CO_2$, CON, $NCO_2$, OH, SH, O, S, N, N=C, F, Cl, Br, I, CN, $NO_2$, $CO_2H$, $NH_2$, etc.; or may be substituent having no alkyl portion, such as F, Cl, Br, I, $NO_2$, CN, $NH_2$, OH, COH, $CO_2H$, etc.

With respect to any relevant formula or structural depiction above, some non-limiting examples of $R^{X1}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, $-CH_2OCO_2R^A$, etc. In some embodiments, $R^{X1}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{X1}$ may be —$CH_2OCOCH_3$.

With respect to any relevant formula or structural depiction above, some non-limiting examples of $R^{X2}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{X2}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{X2}$ may be $CH_3$.

With respect to any relevant formula or structural depiction above, some non-limiting examples of $R^{X3}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{X3}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{X3}$ may be —$CH_2CH_3$.

With respect to any relevant formula or structural depiction above, some non-limiting examples of $R^{X4}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{X4}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{X4}$ may be $CH_3$.

With respect to any relevant formula or structural depiction above, some non-limiting examples of $R^{X5}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{X5}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{X5}$ may be $CH_3$.

With respect to any relevant formula or structural depiction above, some non-limiting examples of $R^{X6}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{X6}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{X6}$ may be —$CH_2CH_3$.

With respect to any relevant formula or structural depiction above, some non-limiting examples of $R^{X7}$ may include $R^A$, F, Cl, CN, $OR^A$, $CF_3$, $NO_2$, $NR^AR^B$, $COR^A$, $CO_2R^A$, $OCOR^A$, $NR^ACOR^B$, $CONR^AR^B$, etc. In some embodiments, $R^{X7}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{X7}$ may be $CH_3$.

In some embodiments, a luminescent compound may be polymerized into the matrix material. For example, the matrix material may comprise repeat units that contain a luminescent group as a pendant group. While there are many ways that a luminescent compound may be polymerized into a matrix material, in some embodiments, a luminescent compound has a polymerizable substituent, or is a polymerized derivative of the polymerizable substituent. In some embodiments, any of $R^{1-38}$, $R^{X1}$-$R^{X7}$, and $R^{1'}$ may be a substituted vinyl, a substituted acrylate, a substituted alkacrylate, an epoxide, a polyol, a polyisocyanate, or a corresponding polymerized derivative thereof. In some embodiments, any of $R^{1-38}$, $R^{X1}$-$R^{X7}$, and $R^{1'}$ may be polymerizable substituent M1, M2, or M3, or polymerized derivative thereof P1, P2, P3, shown in Table 1 below:

TABLE 1

| Any of R$^{1-38}$ and R$^{1'}$ | Any of R$^{1-38}$ and R$^{1'}$ | Any of R$^{1-38}$ and R$^{1'}$ |
|---|---|---|
| Polymerizable substituent 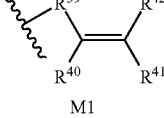 M1 | 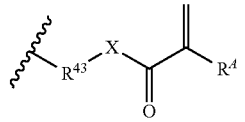 M2 | 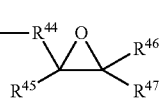 M3 |
| Polymerized derivative 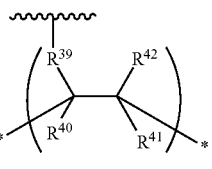 P1 | 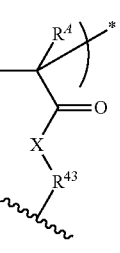 P2 | 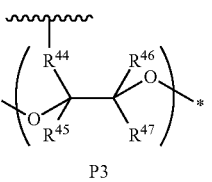 P3 |

With respect to any relevant formula or structural depiction herein, such as M2 or P2, X may be —, O, S, or NH.

With respect to any relevant formula or structural depiction herein, such as M1 or P1, $R^{39}$ may be —; O; $C_{1-12}$ alkyl, including: linear or branched alkyl having a formula $C_aH_{2a}$, or cycloalkyl having a formula $C_aH_{2a-2}$, wherein a is 1, 2, 3, 4, 5, 6, 7, 8, 9, 10, 11, or 12, such as linear or branched alkyl of a formula: $CH_2$, $C_2H_4$, $C_3H_6$, $C_4H_8$, $C_5H_{10}$, $C_6H_{12}$, $C_7H_{14}$, $C_8H_{16}$, $C_9H_{18}$, $C_{10}H_{20}$, etc., or cycloalkyl of a formula: $C_3H_4$, $C_4H_6$, $C_5H_8$, $C_6H_{10}$, $C_7H_{12}$, $C_8H_{14}$, $C_9H_{16}$, $C_{10}H_{18}$, etc.; or $C_{1-12}$-O-alkyl-, including: linear or branched —O-alkyl- having a formula —O—$C_aH_a$—, or —O-cycloalkyl- having a formula —O—$C_aH_{2a-2}$-, wherein a is 1, 2, 3, 4, 5, 6, 7, 8, 9, 10, 11, or 12, such as linear or branched alkyl of a formula: —O—$CH_2$—, —O—$C_2H_4$—, —O—$C_3H_6$—, —O—$C_4H_8$—, —O—$C_5H_{10}$—, —O—$C_6H_{12}$—, —O—$C_7H_{14}$—, —O—$C_8H_{16}$—, —O—$C_9H_{18}$—, —O—$C_{10}H_{20}$—, etc., or —O-cycloalkyl- of a formula: —O—$C_3H_4$—, —O—$C_4H_6$—, —O—$C_5H_8$—, —O—$C_6H_{10}$—, —O—$C_7H_{12}$—, —O—$C_8H_{14}$—, —O—$C_9H_{16}$—, —O—$C_{10}H_{18}$—, etc., where the —O— may be on either side of the alkyl (e.g. —O-alkyl- or -alkyl-O—).

With respect to any relevant formula or structural depiction herein, such as M1 or P1, $R^{40}$ may be $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$. In some embodiments, $R^{40}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; F; Cl; CN; $CF_3$; or $OCOCH_3$.

With respect to any relevant formula or structural depiction herein, such as M1 or P1, $R^{41}$ may be $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$. In some embodiments, $R^{41}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; F; Cl; CN; $CF_3$; or $OCOCH_3$.

With respect to any relevant formula or structural depiction herein, such as M1 or P1, $R^{42}$ may be $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$. In some embodiments, $R^{42}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; F; Cl; CN; $CF_3$; or $OCOCH_3$.

With respect to any relevant formula or structural depiction herein, such as M2 or P2, $R^{43}$ may be —; $C_{1-12}$ alkyl, including: linear or branched alkyl having a formula $C_aH_a$, or cycloalkyl having a formula $C_aH_{2a-2}$, wherein a is 1, 2, 3, 4, 5, 6, 7, 8, 9, 10, 11, or 12, such as linear or branched alkyl of a formula: $CH_2$, $C_2H_4$, $C_3H_6$, $C_4H_8$, $C_5H_{10}$, $C_6H_{12}$, $C_7H_{14}$, $C_8H_{16}$, $C_9H_{18}$, $C_{10}H_{20}$, etc., or cycloalkyl of a formula: $C_3H_4$, $C_4H_6$, $C_5H_8$, $C_6H_{10}$, $C_7H_{12}$, $C_8H_{14}$, $C_9H_{16}$, $C_{10}H_{18}$, etc.; or $C_{1-12}$-O-alkyl-, including: linear or branched —O-alkyl- having a formula —O—$C_aH_a$—, or —O-cycloalkyl- having a formula —O—$C_aH_{2a-2}$—, wherein a is 1, 2, 3, 4, 5, 6, 7, 8, 9, 10, 11, or 12, such as linear or branched alkyl of a formula: —O—$CH_2$—, —O—$C_2H_4$—, —O—$C_3H_6$—, —O—$C_4H_8$—, —O—$C_5H_{10}$—, —O—$C_6H_{12}$—, —O—$C_7H_{14}$—, —O—$C_8H_{16}$—, —O—$C_9H_{18}$—, —O—$C_{10}H_{20}$—, etc., or —O-cycloalkyl- of a formula: —O—$C_3H_4$—, —O—$C_4H_6$—, —O—$C_6H_{10}$—, —O—$C_7H_{12}$—, —O—$C_8H_{14}$—, —O—$C_9H_{16}$—, —O—$C_{10}H_{18}$—, etc., where the —O— does not attach to X.

With respect to any relevant formula or structural depiction herein, such as M3 or P3, $R^{44}$ may be —; O; $C_{1-12}$ alkyl, including: linear or branched alkyl having a formula $C_aH_a$, or cycloalkyl having a formula $C_aH_{2a-2}$, wherein a is 1, 2, 3, 4, 5, 6, 7, 8, 9, 10, 11, or 12, such as linear or branched alkyl of a formula: $CH_2$, $C_2H_4$, $C_3H_6$, $C_4H_8$, $C_5H_{10}$, $C_6H_{12}$, $O_7H_{14}$, $C_8H_{16}$, $C_9H_{18}$, $C_{10}H_{20}$, etc., or —O-cycloalkyl- of a formula: $C_3H_4$, $C_4H_6$, $C_5H_8$, $C_6H_{10}$, $C_7H_{12}$, $C_8H_{14}$, $C_9H_{16}$, $C_{10}H_{18}$, etc.; or $C_{1-12}$-O-alkyl-, including: linear or branched —O-alkyl- having a formula —O—$C_aH_a$—, or —O-cycloalkylhaving a formula —O—$C_aH_{2a-2}$—, wherein a is 1, 2, 3, 4, 5, 6, 7, 8, 9, 10, 11, or 12, such as linear or branched alkyl of a formula: —O—$CH_2$—, —O—$C_2H_4$—, —O—$C_3H_6$—, —O—$C_4H_8$—, —O—$C_5H_{10}$—, —O—$C_6H_{12}$—, —O—$C_7H_{14}$—, —O—$C_8H_{16}$—, —O—$C_9H_{18}$—, —O—$C_{10}H_{20}$—, etc., or —O-cycloalkyl- of a formula: —O—$C_3H_4$—, —O—$C_4H_6$—, —O—$C_5H_8$—, —O—$C_6H_{10}$—, —O—$C_7H_{12}$—, —O—$C_8H_{14}$—, —O—$C_9H_{16}$—, —O—$C_{10}H_{18}$—, etc., where the —O— may be on either side of the alkyl (e.g. —O-alkyl- or -alkyl-O—).

With respect to any relevant formula or structural depiction herein, such as M3 or P3, $R^{45}$ may be $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$. In some embodiments, $R^{45}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; F; Cl; CN; $CF_3$; or $OCOCH_3$.

With respect to any relevant formula or structural depiction herein, such as M3 or P3, $R^{46}$ may be $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$. In some embodiments, $R^{46}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; F; Cl; CN; $CF_3$; or $OCOCH_3$.

With respect to any relevant formula or structural depiction herein, such as M3 or P3, $R^{47}$ may be $R^A$, F, Cl, CN, $OR^A$, $CF_3$, $NO_2$, $NR^AR^B$, $COR^A$, $CO_2R^A$, $OCOR^A$, $NR^ACOR^B$, or $CONR^AR^B$. In some embodiments, $R^{47}$ may be H; $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc.; or $C_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; F; Cl; CN; $CF_3$; or $OCOCH_3$.

In some embodiments, $R^1$ is M1, M2, M3, P1, P2, or P3. In some embodiments, $R^1$ is M1. In some embodiments, $R^1$ is M2. In some embodiments, $R^1$ is M3. In some embodiments, $R^1$ is P1. In some embodiments, $R^1$ is P2. In some embodiments, $R^1$ is P3.

In some embodiments, $R^{1'}$ is M1, M2, M3, P1, P2, or P3. In some embodiments, $R^{1'}$ is M1. In some embodiments, $R^{1'}$ is M2. In some embodiments, $R^{1'}$ is M3. In some embodiments, $R^{1'}$ is P1. In some embodiments, $R^{1'}$ is P2. In some embodiments, $R^{1'}$ is P3.

In some embodiments, $R^2$ is M1, M2, M3, P1, P2, or P3. In some embodiments, $R^2$ is M1. In some embodiments, $R^2$ is M2. In some embodiments, $R^2$ is M3. In some embodiments, $R^2$ is P1. In some embodiments, $R^2$ is P2. In some embodiments, $R^2$ is P3.

In some embodiments, $R^3$ is M1, M2, M3, P1, P2, or P3. In some embodiments, $R^3$ is M1. In some embodiments, $R^3$ is M2. In some embodiments, $R^3$ is M3. In some embodiments, $R^3$ is P1. In some embodiments, $R^3$ is P2. In some embodiments, $R^3$ is P3.

In some embodiments, $R^4$ is M1, M2, M3, P1, P2, or P3. In some embodiments, $R^4$ is M1. In some embodiments, $R^4$ is M2. In some embodiments, $R^4$ is M3. In some embodiments, $R^4$ is P1. In some embodiments, $R^4$ is P2. In some embodiments, $R^4$ is P3.

In some embodiments, $R^5$ is M1, M2, M3, P1, P2, or P3. In some embodiments, $R^5$ is M1. In some embodiments, $R^5$ is M2. In some embodiments, $R^5$ is M3. In some embodiments, $R^5$ is P1. In some embodiments, $R^5$ is P2. In some embodiments, $R^5$ is P3.

In some embodiments, $R^6$ is M1, M2, M3, P1, P2, or P3. In some embodiments, $R^6$ is M1. In some embodiments, $R^6$ is M2. In some embodiments, $R^6$ is M3. In some embodiments, $R^6$ is P1. In some embodiments, $R^6$ is P2. In some embodiments, $R^6$ is P3.

In some embodiments, $R^7$ is M1, M2, M3, P1, P2, or P3. In some embodiments, $R^7$ is M1. In some embodiments, $R^7$ is M2. In some embodiments, $R^7$ is M3. In some embodiments, $R^7$ is P1. In some embodiments, $R^7$ is P2. In some embodiments, $R^7$ is P3.

In some embodiments, $R^8$ is M1, M2, M3, P1, P2, or P3. In some embodiments, $R^8$ is M1. In some embodiments, $R^8$ is M2. In some embodiments, $R^8$ is M3. In some embodiments, $R^8$ is P1. In some embodiments, $R^8$ is P2. In some embodiments, $R^8$ is P3.

In some embodiments, $R^9$ is M1, M2, M3, P1, P2, or P3. In some embodiments, $R^9$ is M1. In some embodiments, $R^9$ is M2. In some embodiments, $R^9$ is M3. In some embodiments, $R^9$ is P1. In some embodiments, $R^9$ is P2. In some embodiments, $R^9$ is P3.

In some embodiments, $R^{10}$ is M1, M2, M3, P1, P2, or P3. In some embodiments, $R^{10}$ is M1. In some embodiments, $R^{10}$ is M2. In some embodiments, $R^{10}$ is M3. In some embodiments, $R^{10}$ is P1. In some embodiments, $R^{10}$ is P2. In some embodiments, $R^{10}$ is P3.

In some embodiments, $R^{11}$ is M1, M2, M3, P1, P2, or P3. In some embodiments, $R^{11}$ is M1. In some embodiments, $R^{11}$ is M2. In some embodiments, $R^{11}$ is M3. In some embodiments, $R^{11}$ is P1. In some embodiments, $R^{11}$ is P2. In some embodiments, $R^{11}$ is P3.

In some embodiments, $R^{12}$ is M1, M2, M3, P1, P2, or P3. In some embodiments, $R^{12}$ is M1. In some embodiments, $R^{12}$ is M2. In some embodiments, $R^{12}$ is M3. In some embodiments, $R^{12}$ is P1. In some embodiments, $R^{12}$ is P2. In some embodiments, $R^{12}$ is P3.

In some embodiments, $R^{13}$ is M1, M2, M3, P1, P2, or P3. In some embodiments, $R^{13}$ is M1. In some embodiments, $R^{13}$ is M2. In some embodiments, $R^{13}$ is M3. In some embodiments, $R^{13}$ is P1. In some embodiments, $R^{13}$ is P2. In some embodiments, $R^{13}$ is P3.

In some embodiments, $R^{14}$ is M1, M2, M3, P1, P2, or P3. In some embodiments, $R^{14}$ is M1. In some embodiments, $R^{14}$ is M2. In some embodiments, $R^{14}$ is M3. In some embodiments, $R^{14}$ is P1. In some embodiments, $R^{14}$ is P2. In some embodiments, $R^{14}$ is P3.

In some embodiments, $R^{15}$ is M1, M2, M3, P1, P2, or P3. In some embodiments, $R^{15}$ is M1. In some embodiments, $R^{15}$ is M2. In some embodiments, $R^{15}$ is M3. In some embodiments, $R^{15}$ is P1. In some embodiments, $R^{15}$ is P2. In some embodiments, $R^{15}$ is P3.

In some embodiments, $R^{16}$ is M1, M2, M3, P1, P2, or P3. In some embodiments, $R^{16}$ is M1. In some embodiments, $R^{16}$ is M2. In some embodiments, $R^{16}$ is M3. In some embodiments, $R^{16}$ is P1. In some embodiments, $R^{16}$ is P2. In some embodiments, $R^{16}$ is P3.

In some embodiments, $R^{17}$ is M1, M2, M3, P1, P2, or P3. In some embodiments, $R^{17}$ is M1. In some embodiments, $R^{17}$ is M2. In some embodiments, $R^{17}$ is M3. In some embodiments, $R^{17}$ is P1. In some embodiments, $R^{17}$ is P2. In some embodiments, $R^{17}$ is P3.

In some embodiments, $R^{18}$ is M1, M2, M3, P1, P2, or P3. In some embodiments, $R^{18}$ is M1. In some embodiments, $R^{18}$ is M2. In some embodiments, $R^{18}$ is M3. In some embodiments, $R^{18}$ is P1. In some embodiments, $R^{18}$ is P2. In some embodiments, $R^{18}$ is P3.

In some embodiments, $R^{19}$ is M1, M2, M3, P1, P2, or P3. In some embodiments, $R^{19}$ is M1. In some embodiments, $R^{19}$ is M2. In some embodiments, $R^{19}$ is M3. In some embodiments, $R^{19}$ is P1. In some embodiments, $R^{19}$ is P2. In some embodiments, $R^{19}$ is P3.

In some embodiments, $R^{20}$ is M1, M2, M3, P1, P2, or P3. In some embodiments, $R^{20}$ is M1. In some embodiments, $R^{20}$ is M2. In some embodiments, $R^{20}$ is M3. In some embodiments, $R^{20}$ is P1. In some embodiments, $R^{20}$ is P2. In some embodiments, $R^{20}$ is P3.

In some embodiments, $R^{21}$ is M1, M2, M3, P1, P2, or P3. In some embodiments, $R^{21}$ is M1. In some embodiments, $R^{21}$ is M2. In some embodiments, $R^{21}$ is M3. In some embodiments, $R^{21}$ is P1. In some embodiments, $R^{21}$ is P2. In some embodiments, $R^{21}$ is P3.

In some embodiments, $R^{22}$ is M1, M2, M3, P1, P2, or P3. In some embodiments, $R^{22}$ is M1. In some embodiments, $R^{22}$ is M2. In some embodiments, $R^{22}$ is M3. In some embodiments, $R^{22}$ is P1. In some embodiments, $R^{22}$ is P2. In some embodiments, $R^{22}$ is P3.

In some embodiments, $R^{23}$ is M1, M2, M3, P1, P2, or P3. In some embodiments, $R^{23}$ is M1. In some embodiments, $R^{23}$ is M2. In some embodiments, $R^{23}$ is M3. In some embodiments, $R^{23}$ is P1. In some embodiments, $R^{23}$ is P2. In some embodiments, $R^{23}$ is P3.

In some embodiments, $R^{24}$ is M1, M2, M3, P1, P2, or P3. In some embodiments, $R^{24}$ is M1. In some embodiments, $R^{24}$ is M2. In some embodiments, $R^{24}$ is M3. In some embodiments, $R^{24}$ is P1. In some embodiments, $R^{24}$ is P2. In some embodiments, $R^{24}$ is P3.

In some embodiments, $R^{25}$ is M1, M2, M3, P1, P2, or P3. In some embodiments, $R^{25}$ is M1. In some embodiments, $R^{25}$ is M2. In some embodiments, $R^{25}$ is M3. In some embodiments, $R^{25}$ is P1. In some embodiments, $R^{25}$ is P2. In some embodiments, $R^{25}$ is P3.

In some embodiments, $R^{26}$ is M1, M2, M3, P1, P2, or P3. In some embodiments, $R^{26}$ is M1. In some embodiments, $R^{26}$ is M2. In some embodiments, $R^{26}$ is M3. In some embodiments, $R^{26}$ is P1. In some embodiments, $R^{26}$ is P2. In some embodiments, $R^{26}$ is P3.

In some embodiments, $R^{27}$ is M1, M2, M3, P1, P2, or P3. In some embodiments, $R^{27}$ is M1. In some embodiments, $R^{27}$ is M2. In some embodiments, $R^{27}$ is M3. In some embodiments, $R^{27}$ is P1. In some embodiments, $R^{27}$ is P2. In some embodiments, $R^{27}$ is P3.

In some embodiments, $R^{28}$ is M1, M2, M3, P1, P2, or P3. In some embodiments, $R^{28}$ is M1. In some embodiments, $R^{28}$ is M2. In some embodiments, $R^{28}$ is M3. In some embodiments, $R^{28}$ is P1. In some embodiments, $R^{28}$ is P2. In some embodiments, $R^{28}$ is P3.

In some embodiments, $R^{29}$ is M1, M2, M3, P1, P2, or P3. In some embodiments, $R^{29}$ is M1. In some embodiments, $R^{29}$ is M2. In some embodiments, $R^{29}$ is M3. In some embodiments, $R^{29}$ is P1. In some embodiments, $R^{29}$ is P2. In some embodiments, $R^{29}$ is P3.

In some embodiments, $R^{30}$ is M1, M2, M3, P1, P2, or P3. In some embodiments, $R^{30}$ is M1. In some embodiments, $R^{30}$ is M2. In some embodiments, $R^{30}$ is M3. In some embodiments, $R^{30}$ is P1. In some embodiments, $R^{30}$ is P2. In some embodiments, $R^{30}$ is P3.

In some embodiments, $R^{31}$ is M1, M2, M3, P1, P2, or P3. In some embodiments, $R^{31}$ is M1. In some embodiments, $R^{31}$ is M2. In some embodiments, $R^{31}$ is M3. In some embodiments, $R^{31}$ is P1. In some embodiments, $R^{31}$ is P2. In some embodiments, $R^{31}$ is P3.

In some embodiments, $R^{32}$ is M1, M2, M3, P1, P2, or P3. In some embodiments, $R^{32}$ is M1. In some embodiments, $R^{32}$ is M2. In some embodiments, $R^{32}$ is M3. In some embodiments, $R^{32}$ is P1. In some embodiments, $R^{32}$ is P2. In some embodiments, $R^{32}$ is P3.

In some embodiments, $R^{33}$ is M1, M2, M3, P1, P2, or P3. In some embodiments, $R^{33}$ is M1. In some embodiments, $R^{33}$ is M2. In some embodiments, $R^{33}$ is M3. In some embodiments, $R^{33}$ is P1. In some embodiments, $R^{33}$ is P2. In some embodiments, $R^{33}$ is P3.

In some embodiments, $R^{34}$ is M1, M2, M3, P1, P2, or P3. In some embodiments, $R^{34}$ is M1. In some embodiments, $R^{34}$ is M2. In some embodiments, $R^{34}$ is M3. In some embodiments, $R^{34}$ is P1. In some embodiments, $R^{34}$ is P2. In some embodiments, $R^{34}$ is P3.

In some embodiments, $R^{35}$ is M1, M2, M3, P1, P2, or P3. In some embodiments, $R^{35}$ is M1. In some embodiments, $R^{35}$ is M2. In some embodiments, $R^{35}$ is M3. In some embodiments, $R^{35}$ is P1. In some embodiments, $R^{35}$ is P2. In some embodiments, $R^{35}$ is P3.

In some embodiments, $R^{36}$ is M1, M2, M3, P1, P2, or P3. In some embodiments, $R^{36}$ is M1. In some embodiments, $R^{36}$ is M2. In some embodiments, $R^{36}$ is M3. In some embodiments, $R^{36}$ is P1. In some embodiments, $R^{36}$ is P2. In some embodiments, $R^{36}$ is P3.

In some embodiments, $R^{37}$ is M1, M2, M3, P1, P2, or P3. In some embodiments, $R^{37}$ is M1. In some embodiments, $R^{37}$ is M2. In some embodiments, $R^{37}$ is M3. In some embodiments, $R^{37}$ is P1. In some embodiments, $R^{37}$ is P2. In some embodiments, $R^{37}$ is P3.

In some embodiments, $R^{38}$ is M1, M2, M3, P1, P2, or P3. In some embodiments, $R^{38}$ is M1. In some embodiments, $R^{38}$ is M2. In some embodiments, $R^{38}$ is M3. In some embodiments, $R^{38}$ is P1. In some embodiments, $R^{38}$ is P2. In some embodiments, $R^{38}$ is P3.

In some embodiments, $R^{X1}$ is M1, M2, M3, P1, P2, or P3. In some embodiments, $R^{X1}$ is M1. In some embodiments, $R^{X1}$ is M2. In some embodiments, $R^{X1}$ is M3. In some embodiments, $R^{X1}$ is P1. In some embodiments, $R^{X1}$ is P2. In some embodiments, $R^{X1}$ is P3. In some embodiments, $R^{X1}$ is M2 or P2, and $R^{43}$ is —$CH_2$—, X is O, and $R^A$ is $CH_3$.

In some embodiments, $R^{X2}$ is M1, M2, M3, P1, P2, or P3. In some embodiments, $R^{X2}$ is M1. In some embodiments, $R^{X2}$ is M2. In some embodiments, $R^{X2}$ is M3. In some embodiments, $R^{X2}$ is P1. In some embodiments, $R^{X2}$ is P2. In some embodiments, $R^{X2}$ is P3.

In some embodiments, $R^{X3}$ is M1, M2, M3, P1, P2, or P3. In some embodiments, $R^{X3}$ is M1. In some embodiments, $R^{X3}$ is M2. In some embodiments, $R^{X3}$ is M3. In some embodiments, $R^{X3}$ is P1. In some embodiments, $R^{X3}$ is P2. In some embodiments, $R^{X3}$ is P3.

In some embodiments, $R^{X4}$ is M1, M2, M3, P1, P2, or P3. In some embodiments, $R^{X4}$ is M1. In some embodiments, $R^{X4}$ is M2. In some embodiments, $R^{X4}$ is M3. In some embodiments, $R^{X4}$ is P1. In some embodiments, $R^{X4}$ is P2. In some embodiments, $R^{X4}$ is P3.

In some embodiments, $R^{X5}$ is M1, M2, M3, P1, P2, or P3. In some embodiments, $R^{X5}$ is M1. In some embodiments, $R^{X5}$ is M2. In some embodiments, $R^{X5}$ is M3. In some embodiments, $R^{X5}$ is P1. In some embodiments, $R^{X5}$ is P2. In some embodiments, $R^{X5}$ is P3.

In some embodiments, $R^{X6}$ is M1, M2, M3, P1, P2, or P3. In some embodiments, $R^{X6}$ is M1. In some embodiments, $R^{X6}$ is M2. In some embodiments, $R^{X6}$ is M3. In some embodiments, $R^{X6}$ is P1. In some embodiments, $R^{X6}$ is P2. In some embodiments, $R^{X6}$ is P3.

In some embodiments, $R^{X7}$ is M1, M2, M3, P1, P2, or P3. In some embodiments, $R^{X7}$ is M1. In some embodiments, $R^{X7}$ is M2. In some embodiments, $R^{X7}$ is M3. In some embodiments, $R^{X7}$ is P1. In some embodiments, $R^{X7}$ is P2. In some embodiments, $R^{X7}$ is P3.

In some embodiments, any of $R^{30}$, $R^{31}$, $R^{32}$, or $R^{33}$ may be a polymerizable group, such as methacrylate or propyl-3-methacrylate:

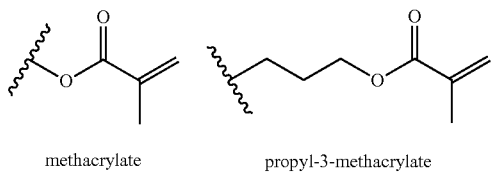

methacrylate          propyl-3-methacrylate or the corresponding polymerized derivative:

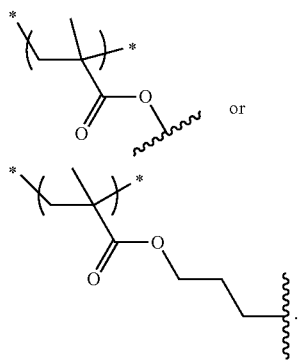

With respect to Formula 8, in some embodiments, $R^{24}$, $R^{26}$, $R^{27}$, $R^{29}$, $R^{30}$, $R^{31}$, $R^{32}$, and $R^{33}$ are H, and the remaining groups are as shown in Table 2.

TABLE 2

| Compound | $R^{25}$ | $R^{28}$ | $R^{34}$ | $R^{35}$ | $R^{36}$ | $R^{37}$ | $R^{38}$ |
|---|---|---|---|---|---|---|---|
| A | H | H | H | H | H | H | H |
| B | H | H | H | H | H | H | CH$_3$ |
| C | H | H | CH$_2$CH$_3$ | H | CH$_2$CH$_3$ | H | CH$_2$CH$_3$ |
| D | CH$_3$ | CH$_3$ | CH$_2$CH$_3$ | H | CH$_2$CH$_3$ | H | CH$_2$CH$_3$ |
| E | H | H | CH$_3$ | H | CH$_3$ | H | H |
| F | H | H | CH$_2$CH$_3$ | CH$_2$CH$_3$ | CH$_2$CH$_3$ | CH$_2$CH$_3$ | H |
| G | H | H | CH$_2$CH$_3$ | CH$_2$CH$_3$ | CH$_2$CH$_3$ | CH$_2$CH$_3$ | CH$_2$CH$_3$ |
| H | CH$_3$ | CH$_3$ | CH$_2$CH$_3$ | H | CH$_2$CH$_3$ | H | H |
| I | H | H | CH$_3$ | CH$_3$ | CH$_3$ | CH$_3$ | H |
| J | H | H | CH$_3$ | CH$_3$ | CH$_2$CH$_3$ | CH$_2$CH$_3$ | H |

With respect to Formula 8, in some embodiments $R^{24}$, $R^{26}$, $R^{27}$, and $R^{29}$; one of $R^{30}$, $R^{31}$, $R^{32}$, and $R^{33}$ is $R^Z$ or a polymerized group of $R^Z$ and the remaining three groups of $R^{30}$, $R^{31}$, $R^{32}$, and $R^{33}$ are H; and the remaining groups of Formula 8 are as shown in Table 3.

TABLE 3

| Compound | $R^Z$ | $R^{25}$ | $R^{28}$ | $R^{34}$ | $R^{35}$ | $R^{36}$ | $R^{37}$ | $R^{38}$ |
|---|---|---|---|---|---|---|---|---|
| K | methacrylate | H | H | CH$_2$CH$_3$ | CH$_2$CH$_3$ | CH$_2$CH$_3$ | CH$_2$CH$_3$ | H |
| L | propyl-3-methacrylate: | H | H | CH$_2$CH$_3$ | CH$_2$CH$_3$ | CH$_2$CH$_3$ | CH$_2$CH$_3$ | H |
| M | propyl-3-methacrylate: | H | H | CH$_3$ | CH$_3$ | CH$_2$CH$_3$ | CH$_2$CH$_3$ | H |
| N | methacrylate | H | H | H | H | H | H | CH$_3$ |
| O | propyl-3-methacrylate: | H | H | CH$_2$CH$_3$ | H | CH$_2$CH$_3$ | H | CH$_2$CH$_3$ |

In some embodiments, a luminescent compound may be rhodamine 6G.

An optical element may comprise more than one luminescent compound so that the absorption and emission spectrum of the optical element may be different from that of one of the luminescent compounds. For example, a spectrum of an optical element may be a combination, such as a concentration related sum, of the spectrum of the individual dyes.

The optical element can comprise a second luminescent compound (or second luminescent material) to enhance the intensity of the first color or second color, increase the spectral separation between the first color and the second color; or both enhance the intensity and increase the spectral separation between the first and second color wavelengths. In an embodiment, the second luminescent compound is N-phenyl-N-(4'-(1-phenyl-1H-benzo[d]imidazol-2-yl)-[1,1'-biphenyl]-4-yl)naphthalen-1-amine [KR material] or 4,4'-bis[N-(naphthyl)-N-phenyl-amino]biphenyl. In one embodiment, the second luminescent compound increases the intensity of the first visible color or the second visible color to increase the distinctiveness between the first and second colors, e.g., green or red. In an embodiment, the second luminescent compound down shifts (red shifts) the peak wavelength of the first visible color relative to the second visible color to increase the distinctiveness between the first and second colors. In an embodiment, the second luminescent compound both increases the intensity and increases the spectral separation between the first and second visible colors' peak wavelengths to enhance the distinction between the first and second visible colors.

In some embodiments, the second luminescent compound absorbs at a first wavelength and emits at a second emissive wavelength. In an embodiment, the second emissive wavelength is substantially near the desired wavelength to be enhanced, or intensified, for example substantially the same peak wavelength of the desired color to be enhanced, or substantially along the desired less overlapped slope of the desired color to be enhanced.

In an embodiment, if the first color is green, then the desired emissive peak wavelength of the luminescent material can be substantially the same as the green emissive peak. For example, in an embodiment, if the peak is green, e.g., about 530 nm, then the second emissive peak wavelength can be between about 515 nm and about 545 nm, between about 520 nm and about 540 nm, or between about 525 nm and about 535 nm. In an embodiment, if the first color is red, then the desired wavelength can be along the red shoulder of the emissive peak, that shoulder which overlaps less with the second color (green) emissive spectra. For example, in one embodiment, if the peak is red, then the second emissive peak wavelength can be between about 550 nm and about 600 nm, between about 550 nm and about 590 nm, or between about 550 nm and about 570 nm.

In another embodiment, the second luminescent compound down shifts (red shifts) a selected peak wavelength to increase the distinctiveness between the first and second colors. For example, the second luminescent compound can have an absorption peak wavelength substantially the same as the green sensitivity wavelength and an emissive peak wavelength at about the peak of the red sensitivity wavelength or along the slope of the sensitivity. In an embodiment, with a small stokes shift luminescent material, substantially green light is absorbed and re-emitted at a longer or more red wavelength.

In another embodiment, the luminescent material both increases the intensity and increases the spectral separation between the first and second colors as described above.

In some embodiments, the luminescent compound or the optical element may absorb light at an absorption wavelength and emit light at an emission wavelength, wherein a human cone photopigment is substantially more sensitive to the emission wavelength than to the absorption wavelength. For example, the human cone photopigment may be at least about 1.5, about 2, about 3, or about 4 times; and/or up to about 10 times, about 20 times, about 50 times, or about 100 times as sensitive to the emission wavelength as it is to the absorption wavelength. In some embodiments, a human cone photopigment is less sensitive to at least about 50%, at least about 70%, at least about 80%, or at least about 90%; and/or up to about 100%; of the visible light absorbed by the luminescent compound as compared to the visible light emitted by the luminescent compound.

Enhanced sensitivity may be with respect to any photopigment, such as a normal human cone middle-wavelength sensitive (M) photopigment, a variant human cone middle-wavelength sensitive (MV) photopigment, a normal human cone long-wavelength sensitive (L) photopigment, variant human cone long-wavelength sensitive (LV) photopigment, or a normal human cone short-wavelength sensitive (S) photopigment, provided that the absorption and emission sensitivities are compared with respect to the same photopigment.

In some embodiments, a luminescent feature such as an optical element, a luminescent compound, or a combination of luminescent compounds has a median wavelength of visible absorption, an average wavelength of visible absorption, a peak wavelength of visible absorption, a maximum wavelength of visible absorption, or at least about 20%, about 50%, about 70%, or about 90% of its visible absorption, in a range of about 380 nm to about 450 nm, about 420 nm to about 480 nm, about 510 nm to about 550 nm, about 520 nm to about 540 nm, or about 530 nm to about 550 nm. In some embodiments, a luminescent feature has a median wavelength of visible emission, an average wavelength of visible emission, a peak wavelength of visible emission, a maximum wavelength of visible emission, or at least about 20%, at least about 50%, at least about 70%, or at least about 90% of its visible absorption in a range of about 500 nm to about 600 nm, about 540 nm to about 580 nm, about 550 nm to about 570 nm, or about 560 nm to about 580 nm.

A median wavelength of visible absorption is the wavelength at which the number of visible photons absorbed having a longer wavelength than the median wavelength is substantially the same as the number of visible photons absorbed having a shorter wavelength than the median wavelength. A median wavelength of visible emission of is the wavelength at which the number of visible photons emitted having a longer wavelength than the median wavelength is substantially the same as the number of visible photons emitted having a shorter wavelength than the median wavelength. A median wavelength may be visually estimated on a spectrum by choosing a wavelength that divides the area of the visible spectrum into two substantially equal halves. An average wavelength of visible absorption (or visible emission) is the average wavelength of all photons in the visible range. A peak wavelength of visible absorption or visible emission is a peak in the spectrum in the visible range. A maximum wavelength of visible absorption or visible emission is the highest peak wavelength in the visible spectrum. As used herein, the terms "absorption," "absorb," or a form of these terms, are used as shorthand for "a median wavelength of visible absorption, an average wavelength of visible absorption, a peak wavelength of visible absorption, a maximum wavelength of visible absorption, or a wavelength range in which at least about 50%, about 80%, or about 90% of visible light absorption occurs." As used herein, the terms "emission," "emit," or a form of these terms are used as shorthand for "a median wavelength of visible emission, an average wavelength of visible emission, a peak wavelength of visible emission, a maximum wavelength of visible emission, or a wavelength range in which at least about 50%, about 80%, or about 90% of visible light emission occurs."

In some embodiments, an optical element may absorb light in a wavelength range near peak sensitivity for an M human cone photopigment, such as a wavelength range where relative sensitivity (Table 4) is at least about 0.9 (e.g. about 510 nm to about 550 nm), about 0.93, about 0.95, about 0.96, about 0.97, about 0.98, about 0.99, or about 1.0; and emit light of a longer wavelength in a wavelength range near peak sensitivity for an L human cone photopigment, such as a wavelength range where relative sensitivity (Table 4) is at least about 0.9 (e.g. about 540 nm to about 580 nm for M human cone photopigments), about 0.93, about 0.95, about 0.96, about 0.97, about 0.98, about 0.99, or about 1.0. An optical element may generally emit at a higher wavelength than it absorbs, such as at a wavelength that is at least about 5 nm, about 10 nm, about 20 nm, or about 30 nm higher. In some embodiments, an optical element may have an absorption that is slightly red-shifted with respect to peak sensitivity for an M human cone photopigment and may have an emission that is slightly blue-shifted with respect to peak sensitivity for an L human cone photopigment.

Relative sensitivities of an M, an L, an S, an MV, and an LV human photopigment are listed in Table 4. The relative sensitivities are scaled to a maximum sensitivity of 1.00 for each photopigment. Suitable absorption and emission ranges for an optical element, a luminescent compound, or a combination of luminescent compounds may be derived from any set of values in Table 4. For example, a luminescent compound may absorb in a low sensitivity range for the M photopigment, such as about 384 nm to about 440 nm, about 380 nm to about 410 nm, or any other range defined by any values in Table 4 in these ranges; and may emit in a high sensitivity range for the M photopigment such as about 465 nm to about 585 nm, about 510 nm to about 550 nm, or any other range defined by any values in Table 4 in these ranges. In some embodiments, a luminescent compound may absorb in a low sensitivity range for the L photopigment, such as about 384 nm to about 460 nm, about 380 nm to about 430 nm, or any other range defined by any values in Table 4 in these ranges; and may emit in a high sensitivity range for the L photopigment such as about 495 nm to about 620 nm, about 540 nm to about 580 nm, or any other range defined by any values in Table 4 in these ranges.

Suitable ranges for absorption and emission of an optical element, a luminescent compound, or a combination of luminescent compounds may also be derived from the sensitivity values from Table 4. For example, for a given photopigment, an absorption range may correspond to wavelengths with sensitivity values below about 0.15, about 0.2, about 0.25, or about 0.3, and an emission range may correspond to wavelengths with sensitivity values about above about 0.4, about 0.5, about 0.6, about 0.7, about 0.8, about 0.9, or about 1 from Table 4. Ranges derived from Table 4 may include median visible wavelength ranges, average visible wavelength ranges, peak visible wavelength ranges, maximum visible wavelength ranges, etc., or may include ranges within which at least about 50%, about 70%, about 80%, or about 90% of the photons in the visible spectrum are emitted or absorbed. In some embodiments, absorption may correspond to a sensitivity value of at least about 0.5, about 0.6, about 0.7, about 0.8, about 0.9, up to about 1 for an M photopigment.

TABLE 4

Relative Sensitivity of Various Photopigments in the Visible Range

| Wavelength (nm) | M | L | S | MV | LV |
|---|---|---|---|---|---|
| 384 | 0.125 | 0.123 | 0.709 | 0.125 | 0.123 |
| 385 | 0.125 | 0.123 | 0.724 | 0.125 | 0.123 |
| 386 | 0.125 | 0.123 | 0.739 | 0.125 | 0.123 |
| 387 | 0.125 | 0.123 | 0.768 | 0.125 | 0.123 |
| 388 | 0.125 | 0.123 | 0.788 | 0.125 | 0.123 |
| 389 | 0.125 | 0.123 | 0.798 | 0.125 | 0.123 |
| 390 | 0.125 | 0.123 | 0.808 | 0.125 | 0.123 |
| 391 | 0.125 | 0.123 | 0.818 | 0.125 | 0.123 |
| 392 | 0.125 | 0.123 | 0.828 | 0.125 | 0.123 |
| 393 | 0.126 | 0.123 | 0.847 | 0.125 | 0.123 |
| 394 | 0.126 | 0.123 | 0.867 | 0.125 | 0.123 |
| 395 | 0.126 | 0.123 | 0.887 | 0.125 | 0.123 |
| 396 | 0.126 | 0.123 | 0.897 | 0.125 | 0.123 |
| 397 | 0.126 | 0.123 | 0.906 | 0.125 | 0.123 |
| 398 | 0.126 | 0.123 | 0.926 | 0.125 | 0.123 |
| 399 | 0.127 | 0.123 | 0.936 | 0.125 | 0.123 |
| 400 | 0.127 | 0.123 | 0.946 | 0.125 | 0.123 |
| 401 | 0.127 | 0.123 | 0.956 | 0.126 | 0.123 |
| 402 | 0.127 | 0.123 | 0.966 | 0.126 | 0.123 |
| 403 | 0.127 | 0.123 | 0.978 | 0.126 | 0.123 |
| 404 | 0.127 | 0.123 | 0.983 | 0.126 | 0.123 |
| 405 | 0.127 | 0.123 | 0.987 | 0.126 | 0.123 |
| 406 | 0.127 | 0.123 | 0.990 | 0.126 | 0.123 |
| 407 | 0.127 | 0.123 | 0.993 | 0.127 | 0.123 |
| 408 | 0.127 | 0.123 | 0.995 | 0.127 | 0.123 |
| 409 | 0.127 | 0.123 | 0.997 | 0.127 | 0.123 |
| 410 | 0.127 | 0.123 | 0.999 | 0.127 | 0.123 |
| 411 | 0.127 | 0.123 | 1.000 | 0.127 | 0.123 |
| 412 | 0.127 | 0.123 | 1.000 | 0.127 | 0.123 |
| 413 | 0.128 | 0.123 | 1.000 | 0.127 | 0.123 |
| 414 | 0.127 | 0.123 | 0.999 | 0.127 | 0.123 |
| 415 | 0.129 | 0.123 | 0.998 | 0.127 | 0.123 |
| 416 | 0.131 | 0.123 | 0.997 | 0.127 | 0.123 |
| 417 | 0.133 | 0.123 | 0.990 | 0.127 | 0.123 |
| 418 | 0.135 | 0.123 | 0.988 | 0.127 | 0.123 |
| 419 | 0.137 | 0.123 | 0.985 | 0.127 | 0.123 |
| 420 | 0.139 | 0.123 | 0.977 | 0.127 | 0.123 |
| 421 | 0.141 | 0.123 | 0.966 | 0.128 | 0.123 |
| 422 | 0.143 | 0.123 | 0.961 | 0.127 | 0.123 |
| 423 | 0.145 | 0.123 | 0.956 | 0.129 | 0.126 |
| 424 | 0.147 | 0.123 | 0.946 | 0.131 | 0.126 |
| 425 | 0.149 | 0.123 | 0.936 | 0.133 | 0.132 |
| 426 | 0.151 | 0.123 | 0.926 | 0.135 | 0.133 |
| 427 | 0.153 | 0.123 | 0.916 | 0.137 | 0.134 |
| 428 | 0.155 | 0.123 | 0.906 | 0.139 | 0.135 |

TABLE 4-continued

Relative Sensitivity of Various Photopigments in the Visible Range

| Wavelength (nm) | M | L | S | MV | LV |
|---|---|---|---|---|---|
| 429 | 0.157 | 0.123 | 0.897 | 0.141 | 0.136 |
| 430 | 0.164 | 0.126 | 0.887 | 0.143 | 0.137 |
| 431 | 0.166 | 0.126 | 0.868 | 0.145 | 0.138 |
| 432 | 0.166 | 0.132 | 0.857 | 0.147 | 0.139 |
| 433 | 0.171 | 0.133 | 0.845 | 0.149 | 0.140 |
| 434 | 0.176 | 0.134 | 0.833 | 0.151 | 0.141 |
| 435 | 0.181 | 0.135 | 0.821 | 0.153 | 0.142 |
| 436 | 0.186 | 0.136 | 0.808 | 0.155 | 0.144 |
| 437 | 0.191 | 0.137 | 0.795 | 0.157 | 0.146 |
| 438 | 0.196 | 0.138 | 0.778 | 0.164 | 0.148 |
| 439 | 0.201 | 0.139 | 0.768 | 0.166 | 0.150 |
| 440 | 0.206 | 0.140 | 0.759 | 0.166 | 0.152 |
| 441 | 0.212 | 0.141 | 0.749 | 0.171 | 0.154 |
| 442 | 0.218 | 0.142 | 0.729 | 0.176 | 0.156 |
| 443 | 0.224 | 0.144 | 0.709 | 0.181 | 0.158 |
| 444 | 0.230 | 0.146 | 0.690 | 0.186 | 0.160 |
| 445 | 0.236 | 0.148 | 0.675 | 0.191 | 0.162 |
| 446 | 0.242 | 0.150 | 0.660 | 0.196 | 0.164 |
| 447 | 0.250 | 0.152 | 0.645 | 0.201 | 0.166 |
| 448 | 0.258 | 0.154 | 0.631 | 0.206 | 0.167 |
| 449 | 0.266 | 0.156 | 0.616 | 0.212 | 0.169 |
| 450 | 0.274 | 0.158 | 0.606 | 0.218 | 0.171 |
| 451 | 0.282 | 0.160 | 0.591 | 0.224 | 0.174 |
| 452 | 0.290 | 0.162 | 0.576 | 0.230 | 0.178 |
| 453 | 0.298 | 0.164 | 0.562 | 0.236 | 0.182 |
| 454 | 0.306 | 0.166 | 0.547 | 0.242 | 0.186 |
| 455 | 0.314 | 0.167 | 0.532 | 0.250 | 0.190 |
| 456 | 0.322 | 0.169 | 0.517 | 0.258 | 0.194 |
| 457 | 0.332 | 0.171 | 0.502 | 0.266 | 0.198 |
| 458 | 0.340 | 0.174 | 0.488 | 0.274 | 0.202 |
| 459 | 0.350 | 0.178 | 0.473 | 0.282 | 0.206 |
| 460 | 0.358 | 0.182 | 0.458 | 0.290 | 0.210 |
| 461 | 0.368 | 0.186 | 0.433 | 0.298 | 0.214 |
| 462 | 0.376 | 0.190 | 0.404 | 0.306 | 0.218 |
| 463 | 0.384 | 0.194 | 0.384 | 0.314 | 0.222 |
| 464 | 0.392 | 0.198 | 0.369 | 0.322 | 0.228 |
| 465 | 0.400 | 0.202 | 0.358 | 0.332 | 0.233 |
| 466 | 0.408 | 0.206 | 0.346 | 0.340 | 0.239 |
| 467 | 0.416 | 0.210 | 0.334 | 0.350 | 0.245 |
| 468 | 0.424 | 0.214 | 0.322 | 0.358 | 0.251 |
| 469 | 0.432 | 0.218 | 0.305 | 0.368 | 0.257 |
| 470 | 0.440 | 0.222 | 0.276 | 0.376 | 0.266 |
| 471 | 0.448 | 0.228 | 0.251 | 0.384 | 0.275 |
| 472 | 0.456 | 0.233 | 0.239 | 0.392 | 0.284 |
| 473 | 0.464 | 0.239 | 0.228 | 0.400 | 0.293 |
| 474 | 0.472 | 0.245 | 0.216 | 0.408 | 0.300 |
| 475 | 0.481 | 0.251 | 0.204 | 0.416 | 0.307 |
| 476 | 0.490 | 0.257 | 0.192 | 0.424 | 0.315 |
| 477 | 0.500 | 0.266 | 0.184 | 0.432 | 0.320 |
| 478 | 0.513 | 0.275 | 0.176 | 0.440 | 0.327 |
| 479 | 0.525 | 0.284 | 0.168 | 0.448 | 0.335 |
| 480 | 0.535 | 0.293 | 0.161 | 0.456 | 0.342 |
| 481 | 0.538 | 0.300 | 0.153 | 0.464 | 0.348 |
| 482 | 0.551 | 0.307 | 0.145 | 0.472 | 0.354 |
| 483 | 0.564 | 0.315 | 0.137 | 0.481 | 0.363 |
| 484 | 0.577 | 0.320 | 0.129 | 0.490 | 0.369 |
| 485 | 0.590 | 0.327 | 0.121 | 0.500 | 0.377 |
| 486 | 0.603 | 0.335 | 0.113 | 0.513 | 0.385 |
| 487 | 0.616 | 0.342 | 0.105 | 0.525 | 0.393 |
| 488 | 0.629 | 0.348 | 0.098 | 0.535 | 0.401 |
| 489 | 0.642 | 0.354 | 0.090 | 0.538 | 0.409 |
| 490 | 0.655 | 0.363 | 0.082 | 0.551 | 0.417 |
| 491 | 0.668 | 0.369 | 0.080 | 0.564 | 0.425 |
| 492 | 0.681 | 0.377 | 0.074 | 0.577 | 0.433 |
| 493 | 0.694 | 0.385 | 0.070 | 0.590 | 0.440 |
| 494 | 0.707 | 0.393 | 0.066 | 0.603 | 0.448 |
| 495 | 0.720 | 0.401 | 0.062 | 0.616 | 0.456 |
| 496 | 0.733 | 0.409 | 0.058 | 0.629 | 0.464 |
| 497 | 0.746 | 0.417 | 0.054 | 0.642 | 0.472 |
| 498 | 0.759 | 0.425 | 0.050 | 0.655 | 0.480 |
| 499 | 0.772 | 0.433 | 0.046 | 0.668 | 0.488 |
| 500 | 0.785 | 0.440 | 0.042 | 0.681 | 0.500 |
| 501 | 0.798 | 0.448 | 0.038 | 0.694 | 0.515 |

TABLE 4-continued

Relative Sensitivity of Various Photopigments in the Visible Range

| Wavelength (nm) | M | L | S | MV | LV |
|---|---|---|---|---|---|
| 502 | 0.820 | 0.456 | 0.034 | 0.707 | 0.527 |
| 503 | 0.840 | 0.464 | 0.033 | 0.720 | 0.537 |
| 504 | 0.850 | 0.472 | 0.031 | 0.733 | 0.550 |
| 505 | 0.856 | 0.480 | 0.029 | 0.746 | 0.565 |
| 506 | 0.867 | 0.488 | 0.027 | 0.759 | 0.577 |
| 507 | 0.878 | 0.500 | 0.025 | 0.772 | 0.590 |
| 508 | 0.889 | 0.515 | 0.023 | 0.785 | 0.603 |
| 509 | 0.899 | 0.527 | 0.021 | 0.798 | 0.616 |
| 510 | 0.908 | 0.537 | 0.021 | 0.820 | 0.629 |
| 511 | 0.917 | 0.550 | 0.021 | 0.840 | 0.641 |
| 512 | 0.926 | 0.565 | 0.020 | 0.850 | 0.654 |
| 513 | 0.934 | 0.577 | 0.020 | 0.856 | 0.667 |
| 514 | 0.942 | 0.590 | 0.020 | 0.867 | 0.680 |
| 515 | 0.949 | 0.603 |  | 0.878 | 0.693 |
| 516 | 0.956 | 0.616 |  | 0.889 | 0.705 |
| 517 | 0.962 | 0.629 |  | 0.899 | 0.718 |
| 518 | 0.968 | 0.641 |  | 0.908 | 0.731 |
| 519 | 0.973 | 0.654 |  | 0.917 | 0.744 |
| 520 | 0.978 | 0.667 |  | 0.926 | 0.757 |
| 521 | 0.983 | 0.680 |  | 0.934 | 0.769 |
| 522 | 0.986 | 0.693 |  | 0.942 | 0.782 |
| 523 | 0.990 | 0.705 |  | 0.949 | 0.795 |
| 524 | 0.993 | 0.718 |  | 0.956 | 0.801 |
| 525 | 0.995 | 0.731 |  | 0.962 | 0.814 |
| 526 | 0.997 | 0.744 |  | 0.968 | 0.825 |
| 527 | 0.999 | 0.757 |  | 0.973 | 0.835 |
| 528 | 0.999 | 0.769 |  | 0.978 | 0.847 |
| 529 | 1.000 | 0.782 |  | 0.983 | 0.858 |
| 530 | 1.000 | 0.795 |  | 0.986 | 0.869 |
| 531 | 0.999 | 0.801 |  | 0.990 | 0.880 |
| 532 | 0.998 | 0.814 |  | 0.993 | 0.890 |
| 533 | 0.997 | 0.825 |  | 0.995 | 0.900 |
| 534 | 0.995 | 0.835 |  | 0.997 | 0.910 |
| 535 | 0.992 | 0.847 |  | 0.999 | 0.919 |
| 536 | 0.989 | 0.858 |  | 0.999 | 0.927 |
| 537 | 0.986 | 0.869 |  | 1.000 | 0.935 |
| 538 | 0.982 | 0.880 |  | 1.000 | 0.943 |
| 539 | 0.977 | 0.890 |  | 0.999 | 0.950 |
| 540 | 0.973 | 0.900 |  | 0.998 | 0.956 |
| 541 | 0.967 | 0.910 |  | 0.997 | 0.963 |
| 542 | 0.961 | 0.919 |  | 0.995 | 0.968 |
| 543 | 0.955 | 0.927 |  | 0.992 | 0.974 |
| 544 | 0.948 | 0.935 |  | 0.989 | 0.978 |
| 545 | 0.941 | 0.943 |  | 0.986 | 0.983 |
| 546 | 0.933 | 0.950 |  | 0.982 | 0.987 |
| 547 | 0.923 | 0.956 |  | 0.977 | 0.990 |
| 548 | 0.912 | 0.963 |  | 0.973 | 0.993 |
| 549 | 0.897 | 0.968 |  | 0.967 | 0.995 |
| 550 | 0.887 | 0.974 |  | 0.961 | 0.997 |
| 551 | 0.877 | 0.978 |  | 0.955 | 0.999 |
| 552 | 0.866 | 0.983 |  | 0.948 | 1.000 |
| 553 | 0.855 | 0.987 |  | 0.941 | 1.000 |
| 554 | 0.843 | 0.990 |  | 0.933 | 1.000 |
| 555 | 0.831 | 0.993 |  | 0.923 | 0.999 |
| 556 | 0.818 | 0.995 |  | 0.912 | 0.998 |
| 557 | 0.805 | 0.997 |  | 0.897 | 0.997 |
| 558 | 0.792 | 0.999 |  | 0.887 | 0.995 |
| 559 | 0.778 | 1.000 |  | 0.877 | 0.990 |
| 560 | 0.771 | 1.000 |  | 0.866 | 0.986 |
| 561 | 0.764 | 1.000 |  | 0.855 | 0.982 |
| 562 | 0.749 | 0.999 |  | 0.843 | 0.978 |
| 563 | 0.734 | 0.998 |  | 0.831 | 0.973 |
| 564 | 0.719 | 0.997 |  | 0.818 | 0.968 |
| 565 | 0.704 | 0.995 |  | 0.805 | 0.962 |
| 566 | 0.688 | 0.992 |  | 0.792 | 0.956 |
| 567 | 0.671 | 0.990 |  | 0.778 | 0.949 |
| 568 | 0.655 | 0.986 |  | 0.771 | 0.942 |
| 569 | 0.640 | 0.982 |  | 0.764 | 0.934 |
| 570 | 0.625 | 0.978 |  | 0.749 | 0.926 |
| 571 | 0.610 | 0.973 |  | 0.734 | 0.917 |
| 572 | 0.595 | 0.968 |  | 0.719 | 0.908 |
| 573 | 0.580 | 0.962 |  | 0.704 | 0.899 |
| 574 | 0.565 | 0.956 |  | 0.688 | 0.889 |
| 575 | 0.550 | 0.949 |  | 0.671 | 0.879 |
| 576 | 0.535 | 0.942 |  | 0.655 | 0.868 |
| 577 | 0.520 | 0.934 |  | 0.640 | 0.857 |
| 578 | 0.505 | 0.926 |  | 0.625 | 0.845 |
| 579 | 0.490 | 0.917 |  | 0.610 | 0.833 |
| 580 | 0.475 | 0.908 |  | 0.595 | 0.821 |
| 581 | 0.460 | 0.899 |  | 0.580 | 0.808 |
| 582 | 0.445 | 0.889 |  | 0.565 | 0.795 |
| 583 | 0.430 | 0.879 |  | 0.550 | 0.778 |
| 584 | 0.415 | 0.868 |  | 0.535 | 0.768 |
| 585 | 0.400 | 0.857 |  | 0.520 | 0.759 |
| 586 | 0.385 | 0.845 |  | 0.505 | 0.749 |
| 587 | 0.370 | 0.833 |  | 0.490 | 0.729 |
| 588 | 0.355 | 0.821 |  | 0.475 | 0.709 |
| 589 | 0.340 | 0.808 |  | 0.460 | 0.690 |
| 590 | 0.328 | 0.795 |  | 0.445 | 0.675 |
| 591 | 0.316 | 0.778 |  | 0.430 | 0.660 |
| 592 | 0.304 | 0.768 |  | 0.415 | 0.645 |
| 593 | 0.292 | 0.759 |  | 0.400 | 0.631 |
| 594 | 0.280 | 0.749 |  | 0.385 | 0.616 |
| 595 | 0.268 | 0.739 |  | 0.370 | 0.606 |
| 596 | 0.256 | 0.729 |  | 0.355 | 0.591 |
| 597 | 0.244 | 0.709 |  | 0.340 | 0.576 |
| 598 | 0.232 | 0.690 |  | 0.328 | 0.562 |
| 599 | 0.220 | 0.675 |  | 0.316 | 0.547 |
| 600 | 0.208 | 0.660 |  | 0.304 | 0.532 |
| 601 | 0.200 | 0.645 |  | 0.292 | 0.517 |
| 602 | 0.192 | 0.631 |  | 0.280 | 0.502 |
| 603 | 0.184 | 0.616 |  | 0.268 | 0.488 |
| 604 | 0.176 | 0.606 |  | 0.256 | 0.473 |
| 605 | 0.170 | 0.591 |  | 0.244 | 0.458 |
| 606 | 0.164 | 0.576 |  | 0.232 | 0.443 |
| 607 | 0.158 | 0.562 |  | 0.220 | 0.429 |
| 608 | 0.152 | 0.547 |  | 0.208 | 0.414 |
| 609 | 0.146 | 0.532 |  | 0.200 | 0.399 |
| 610 | 0.140 | 0.517 |  | 0.192 | 0.384 |
| 611 | 0.134 | 0.502 |  | 0.184 | 0.369 |
| 612 | 0.128 | 0.488 |  | 0.176 | 0.358 |
| 613 | 0.122 | 0.473 |  | 0.170 | 0.346 |
| 614 | 0.116 | 0.458 |  | 0.164 | 0.334 |
| 615 | 0.110 | 0.443 |  | 0.158 | 0.322 |
| 616 | 0.104 | 0.429 |  | 0.152 | 0.310 |
| 617 | 0.098 | 0.414 |  | 0.146 | 0.299 |
| 618 | 0.092 | 0.399 |  | 0.140 | 0.287 |
| 619 | 0.086 | 0.384 |  | 0.134 | 0.275 |
| 620 | 0.080 | 0.369 |  | 0.128 | 0.263 |
| 621 | 0.076 | 0.358 |  | 0.122 | 0.251 |
| 622 | 0.072 | 0.346 |  | 0.116 | 0.239 |
| 623 | 0.068 | 0.334 |  | 0.110 | 0.228 |
| 624 | 0.064 | 0.322 |  | 0.104 | 0.216 |
| 625 | 0.060 | 0.310 |  | 0.098 | 0.204 |
| 626 | 0.056 | 0.299 |  | 0.092 | 0.192 |
| 627 | 0.052 | 0.287 |  | 0.086 | 0.184 |
| 628 | 0.048 | 0.275 |  | 0.080 | 0.176 |
| 629 | 0.044 | 0.263 |  | 0.076 | 0.168 |
| 630 | 0.040 | 0.251 |  | 0.072 | 0.161 |
| 631 | 0.038 | 0.239 |  | 0.068 | 0.153 |
| 632 | 0.036 | 0.228 |  | 0.064 | 0.145 |
| 633 | 0.034 | 0.216 |  | 0.060 | 0.137 |
| 634 | 0.032 | 0.204 |  | 0.056 | 0.133 |
| 635 | 0.030 | 0.192 |  | 0.052 | 0.129 |
| 636 | 0.028 | 0.184 |  | 0.048 | 0.125 |
| 637 | 0.026 | 0.176 |  | 0.044 | 0.121 |
| 638 | 0.024 | 0.168 |  | 0.040 | 0.117 |
| 639 | 0.022 | 0.161 |  | 0.038 | 0.113 |
| 640 | 0.020 | 0.153 |  | 0.036 | 0.109 |
| 641 | 0.018 | 0.145 |  | 0.034 | 0.105 |
| 642 | 0.016 | 0.137 |  | 0.032 | 0.101 |
| 643 | 0.014 | 0.129 |  | 0.030 | 0.098 |
| 644 | 0.014 | 0.121 |  | 0.028 | 0.093 |
| 645 | 0.013 | 0.113 |  | 0.026 | 0.088 |
| 646 | 0.012 | 0.105 |  | 0.024 | 0.083 |
| 647 | 0.012 | 0.098 |  | 0.022 | 0.078 |

TABLE 4-continued

Relative Sensitivity of Various Photopigments in the Visible Range

| Wavelength (nm) | M | L | S | MV | LV |
|---|---|---|---|---|---|
| 648 | 0.011 | 0.090 | | 0.020 | 0.073 |
| 649 | 0.011 | 0.082 | | 0.018 | 0.068 |
| 650 | 0.010 | 0.080 | | 0.016 | 0.063 |
| 651 | 0.010 | 0.074 | | 0.014 | 0.058 |
| 652 | 0.009 | 0.070 | | 0.014 | 0.053 |
| 653 | 0.009 | 0.066 | | 0.013 | 0.052 |
| 654 | 0.008 | 0.062 | | 0.012 | 0.050 |
| 655 | 0.008 | 0.058 | | 0.012 | 0.049 |
| 656 | 0.007 | 0.054 | | 0.011 | 0.047 |
| 657 | 0.007 | 0.050 | | 0.011 | 0.046 |
| 658 | 0.006 | 0.046 | | 0.010 | 0.044 |
| 659 | 0.006 | 0.042 | | 0.010 | 0.043 |
| 660 | 0.005 | 0.038 | | 0.009 | 0.041 |
| 661 | 0.005 | 0.034 | | 0.009 | 0.040 |
| 662 | 0.004 | 0.033 | | 0.008 | 0.038 |
| 663 | 0.004 | 0.031 | | 0.008 | 0.037 |
| 664 | 0.003 | 0.029 | | 0.007 | 0.035 |
| 665 | 0.003 | 0.027 | | 0.007 | 0.034 |
| 666 | 0.003 | 0.025 | | 0.006 | 0.033 |
| 667 | 0.003 | 0.023 | | 0.006 | 0.031 |
| 668 | 0.003 | 0.021 | | 0.005 | 0.030 |
| 669 | 0.003 | 0.019 | | 0.005 | 0.028 |
| 670 | 0.003 | 0.017 | | 0.004 | 0.027 |
| 671 | 0.003 | 0.015 | | 0.004 | 0.025 |
| 672 | 0.003 | 0.013 | | 0.003 | 0.024 |
| 673 | 0.003 | 0.011 | | 0.003 | 0.022 |
| 674 | 0.003 | 0.009 | | 0.003 | 0.021 |
| 675 | 0.003 | 0.008 | | 0.003 | 0.019 |

In some embodiments, and optical element may absorb at about 530 nm to about 540 nm, about 534 nm to about 537 nm, about 535 nm to about 536 nm, about 545 nm to about 565 nm, about 549 nm to about 562 nm, about 535 nm, about 536 nm, about 549 nm, about 557 nm, or about 562 nm; and may have a transmittance of less than about 90%, about 85%, or about 80% in one of those ranges.

In some embodiments, an optical element may absorb at about 540 nm to about 550 nm, about 545 nm to about 550 nm, or about 547 nm; and/or may emit at about 560 nm to about 580 nm, about 565 nm to about 575 nm, or about 569 nm.

In some embodiments, an optical element is configured to absorb and emit light, e.g. absorb light of a shorter wavelength and emit light of a longer wavelength, so that a first color having a first set of color coordinates is converted to a second color having a second set of color coordinates. In some embodiments, the distance between the first set of color coordinates and the second set of color coordinates may be at least about 0.005, about 0.01, about 0.02, about 0.03, about 0.04, or about 0.05 color coordinate units. A distance $\Delta$ between two sets of color coordinates, $(x_1, y_1)$ and $(x_2, y_2)$, may be obtained by the formula:

$$\Delta = \sqrt{[x_2 - x_1]^2 + [y_2 - y_1]^2}$$

For individuals with an impaired ability to discern colors, the distance between the first set of color coordinates and the second set of color coordinates in the direction normal to a color confusion line nearest to the first set of color coordinates (referred to hereafter as "normal distance") may be at least about 0.02, about 0.03, about 0.04, or about 0.05 color coordinate units. A "color coordination unit" refers to a distance on a CIE color triangle. CIE (1932). *Commission Internationale de l'Eclairage proceedings,* 1931. Cambridge University Press, Cambridge. This exemplary standard is known in the art as the 1931 CIE XYZ color space and was set by the International Commission on Illumination. For example, the CIE color (0.332, 345) is 0.332 color coordinate units in distance from the y-axis and 0.345 color coordination units in distance from the x axis. For the purposes of this disclosure, the two color coordinates in a CIE color triangle (x, y) will be referred to as "the x color coordinate" and "the y color coordinate."

For example, Table 5 shows how colors may be converted by an optical element for use with individuals with an impaired ability to discern colors. Some optical elements may convert color A to color A', and/or may convert color B to color B'. Normal distances may be obtained by subtracting the distance normal to a color confusion line of a first color coordinates from the distance normal to a color confusion line of a second color coordinate. A negative (–) distance value indicates that the point has a lower y value than the color confusion line, and a positive distance value indicates that the point has a higher y value than the color confusion line. The distance between the color coordinates of A and A' in the direction normal to the color confusion line closest to the color coordinates of A is about 0.0095. The distance between the color coordinates of B and B' in the direction normal to the color confusion line closest to the coordinates of B is about 0.0133.

TABLE 5

| Color | x | y | deuteranopia color confusion line | distance normal to color confusion line |
|---|---|---|---|---|
| A | 0.379 | 0.486 | 8 | –0.0020 |
| A' | 0.384 | 0.468 | 8 | 0.0075 |
| B | 0.478 | 0.414 | 9 | 0.0180 |
| B' | 0.523 | 0.39 | 9 | 0.0313 |

In some embodiments, the x color coordinate may be about 0.290 to about 0.295, about 0.325 to about 0.335, about 0.330 to about 0.335, about 0.370 to about 0.375, about 0.375 to about 0.385, about 0.380 to about 0.385, about 0.475 to about 0.485, about 0.475 to about 0.480, about 0.51 to about 0.52, about 0.520 to about 0.525, about 0.520 to about 0.523, about 0.56 to about 0.57, about 0.570 to about 0.575, about 0.293, about 0.332, about 0.37, about 0.371, about 0.379, about 0.476, about 0.478, about 0.482, about 0.514, about 0.566, or about 0.573; and/or the y color coordinate may be about 0.34 to about 0.35, about 0.385 to about 0.395, about 0.395 to about 0.400, about 0.41 to about 0.42, about 0.465 to about 0.470, about 0.465 to about 0.475, about 0.48 to about 0.49, about 0.495 to about 0.50, about 0.46 to about 0.47, about 0.344, about 0.345, about 0.39, about 0.398, about 0.463, about 0.468, about 0.47, about 0.486, or about 0.497.

In some embodiments, the first set of color coordinates may be about (0.375-0.380, 0.485-0.490), about (0.475-0.480, 0.410-0.415), about (0.330-0.335, 0.340-0.345), about (0.570-0.575, 0.340-0.345), about (0.510-0.515, 0.340-0.344), about (0.480-0.485, 0.388-0.392), about (0.475-0.480, 0.468-0.473), about (0.565-0.570, 0.395-0.400), about (0.290-0.295, 0.495-0.500), about (0.368-0.373, 0.485-0.490), or about (0.370-0.375, 0.460-0.465).

In some embodiments, the first set of color coordinates is A or B and/or the second set of color coordinates is A' or B'. In some embodiments, the first set of color coordinates is one of colors 1-9 in Table 6.

TABLE 6

| Color | x | y | deuteranopia color confusion line | distance normal to color confusion line |
|---|---|---|---|---|
| 1 | 0.332 | 0.345 | 6 | −0.0194 |
| 2 | 0.573 | 0.344 | 9 | −0.0153 |
| 3 | 0.514 | 0.344 | 8 | −0.0069 |
| 4 | 0.482 | 0.390 | 8 | 0.0041 |
| 5 | 0.476 | 0.470 | 9 | 0.0021 |
| 6 | 0.566 | 0.398 | 9 | 0.0171 |
| 7 | 0.293 | 0.497 | 7 | 0.0120 |
| 8 | 0.37 | 0.486 | 8 | −0.0042 |
| 9 | 0.371 | 0.463 | 8 | −0.0201 |

A color confusion line includes any line on a CIE color triangle along which a person with a color blindness condition has difficulty distinguishing colors. Some examples of color confusion lines for deuteranopia are provided in Table 7 and some examples of color confusion lines for protanopia are provided in Table 8. The color confusion lines have a formula y=mx+b, where m is the slope and b is the y-intercept. In some embodiments, the color confusion line nearest to the first set of color coordinates is deuteranopia color confusion line 1, deuteranopia color confusion line 2, deuteranopia color confusion line 3, deuteranopia color confusion line 4, deuteranopia color confusion line 5, deuteranopia color confusion line 6, deuteranopia color confusion line 7, deuteranopia color confusion line 8, or deuteranopia color confusion line 9, as shown in Table 7. In some embodiments, the color confusion line nearest to the first set of color coordinates is protanopia color confusion line 1, protanopia color confusion line 2, protanopia color confusion line 3, protanopia color confusion line 4, protanopia color confusion line 5, protanopia color confusion line 6, protanopia color confusion line 7, protanopia color confusion line 8, protanopia color confusion line 9, or protanopia color confusion line 10, as shown in Table 8.

shown in FIG. 1. First line 210 is calculated that incorporates or intersects first set of color coordinates 215 and is parallel to color confusion line 220. Second line 230 is calculated that incorporates or intersects second set of color coordinates 235 and is parallel to color confusion line 220.

First line 210 and second line 230 have the same slope as the color confusion line. Y-intercept $b_1$ can be determined from the first set of color coordinates 215, and y-intercept $b_2$ can be determined from the second set of color coordinates 235. For example, if the second set of color coordinates is $(x_2, y_2)$, the y-intercept $b_2$ would be:

$$b_2 = y_2 - mx_2,$$

where m is the slope of the color confusion line (and any lines parallel to the color confusion line).

The shortest distance D between first line 210 and second line 230 is equal to the distance between the two sets of color coordinates in a direction normal to the color confusion lines. This distance may be determined using the following formula:

$$D = \sqrt{\left[\frac{b_2 - b_1}{\frac{-1}{m} - m}\right]^2 + \left[\frac{b_2 - b_1}{-1 - m^2}\right]^2}$$

wherein D is the distance between the two parallel lines, or the distance in the direction normal to the color confusion line; $b_2$ is the y-intercept for the line incorporating second set of color coordinates; $b_1$ is the y-intercept for the line incorporating first set of color coordinates; and m is the slope of the color confusion line. Tables 2 and 3 show the values of D for some color confusion lines at various values of $b_2 - b_1$. The distance may also be estimated by plotting the lines and measuring the

TABLE 7

Slopes (m) and y-intercepts (b) of deuteranopia color confusion lines

| | | deutoronopia color confusion line | | | | | | | | |
|---|---|---|---|---|---|---|---|---|---|---|
| | | 1 | 2 | 3 | 4 | 5 | 6 | 7 | 8 | 9 |
| m | | −0.4 | −0.46 | −0.54 | −0.63 | −0.71 | −0.79 | −0.87 | −0.96 | −1.04 |
| b | | 0.112 | 0.207 | 0.312 | 0.418 | 0.527 | 0.632 | 0.736 | 0.847 | 0.962 |
| value of D when $b_2-b_1$ is: | 0.02 | 0.019 | 0.018 | 0.018 | 0.017 | 0.016 | 0.016 | 0.015 | 0.014 | 0.014 |
| | 0.03 | 0.028 | 0.027 | 0.026 | 0.025 | 0.024 | 0.024 | 0.023 | 0.022 | 0.021 |
| | 0.04 | 0.037 | 0.036 | 0.035 | 0.034 | 0.033 | 0.031 | 0.030 | 0.029 | 0.028 |
| | 0.05 | 0.046 | 0.045 | 0.044 | 0.042 | 0.041 | 0.039 | 0.038 | 0.036 | 0.035 |
| | 0.06 | 0.056 | 0.055 | 0.053 | 0.051 | 0.049 | 0.047 | 0.045 | 0.043 | 0.042 |

TABLE 8

Slopes (m) and y-intercepts (b) of protanopia color confusion lines

| | | protanopia color confusion line | | | | | | | | | |
|---|---|---|---|---|---|---|---|---|---|---|---|
| | | 1 | 2 | 3 | 4 | 5 | 6 | 7 | 8 | 9 | 10 |
| m | | 0.36 | 0.23 | 0.08 | −0.06 | −0.19 | −0.32 | −0.45 | −0.58 | −0.71 | −0.87 |
| b | | −0.04 | 0.06 | 0.18 | 0.28 | 0.38 | 0.48 | 0.58 | 0.68 | 0.78 | 0.9 |
| value of D when $b_2-b_1$ is: | 0.02 | 0.019 | 0.019 | 0.020 | 0.020 | 0.020 | 0.019 | 0.018 | 0.017 | 0.016 | 0.015 |
| | 0.03 | 0.028 | 0.029 | 0.030 | 0.030 | 0.029 | 0.029 | 0.027 | 0.026 | 0.024 | 0.023 |
| | 0.04 | 0.038 | 0.039 | 0.040 | 0.040 | 0.039 | 0.038 | 0.036 | 0.035 | 0.033 | 0.030 |
| | 0.05 | 0.047 | 0.049 | 0.050 | 0.050 | 0.049 | 0.048 | 0.046 | 0.043 | 0.041 | 0.038 |
| | 0.06 | 0.056 | 0.058 | 0.060 | 0.060 | 0.059 | 0.057 | 0.055 | 0.052 | 0.049 | 0.045 |

While there may be many methods that can be used to determine the distance between two sets of color coordinates in a direction normal to a color confusion line, one method is distance between the lines. In some embodiments, $b_2-b_1$ may be at least about 0.02, about 0.03, about 0.04, about 0.05, or about 0.06.

The optical element can also comprise a light absorbing dye, which can also be dispersed in the substantially transparent matrix material. In an embodiment, a light absorbing dye has an absorption band that substantially overlaps with the second visible color wavelength. The combination of a luminescent compound that emits light at the first visible light wavelength and a light absorbing dye that absorbs light at the second visible light wavelength can help improve distinction between the two colors. For example, a luminescent compound that emits in the green wavelength of visible light used in combination with a light absorbing dye that absorbs red wavelength visible light may improve the ability of a user to distinguish between red and green color hues.

A light-absorbing dye may absorb one color, such as red, and is transparent to all other wavelengths of light. A light-absorbing dye may or may not be fluorescent. In an embodiment, a purpose of the light-absorbing dye is to make objects of the same color as the dye's absorption band appear darker when viewed through the filter. Known light absorbing dyes can be used. In an embodiment, a light absorbing dye comprises a phthalocyanine dye, such as, for example, Epolight 6661 and/or Epolight 6084, both of which are products of Epolin, Inc (Newark, N.J., USA). More than one light absorbing dye can be used. However, the substantial transparency of the optical element should be maintained.

An optical element can be manufactured in accordance with known film-forming or lens-forming techniques, as guided by the teachings provided herein. The luminescent compound and/or light absorbing dye can be combined with the substantially transparent matrix material in an appropriate weight ratio. The ingredients can be dissolved in an appropriate solvent, such as toluene, optionally with the use of sonication. The solution can then be spin-coated into a film or onto any substantially transparent substrate. Heating the resulting film to evaporate the solvent provides a corrective optical element, which can be placed between a colorblind person's eyes and an object that they are viewing to be effective.

To enhance the effectiveness of the filter, particularly in low-light settings, some luminescent compounds may have an absorption band(s) that is (are) as narrow as possible. Some luminescent compounds may have a narrow Stokes shift, for example, of less than about 150 nm, or less than about 120 nm. A Stokes shift is the difference (in wavelength or frequency units) between positions of the band maxima of the absorption and emission spectra of the same electronic transition. If, for example, a compound has an absorption peak wavelength of about 485 nm and an emission peak wavelength of about 550 nm, the compound has a Stokes Shift of about 65 nm.

In an embodiment, a luminescent compound absorbs from within the UV/blue absorption spectrum and emits within the green emission spectrum, enhancing the perceived emitted green light. In an embodiment, a luminescent compound absorbs from within the green absorption spectrum and emits within the red emission spectrum, enhancing the perceived emitted red light. In an embodiment, a luminescent compound absorbs from within the UV or blue absorption spectrum and emits within the red emission spectrum, enhancing the perceived emitted red light. In some embodiments, the luminescent compound can be a light-absorbing dye. In some embodiments, the light-absorbing dye may absorb color approaching UV or blue light wavelengths, in the range of about 200 to about 450 nm, to increase color contrast and improve color discernment while minimizing fatigue and visual stress associated with prolonged exposure to such short, high energy wavelengths. In an embodiment, this can have the additional effect of protecting the user from undesirable UV radiation. Some undesirable UV wavelengths are classified as mid-range UVB, ranging from about 290 to about 320 nm, and long range UVA, ranging from about 320 to about 400 nm. In some embodiments, UV absorbing materials for use with lenses may be benzophenones and benzotriazoles and their derivatives, described in U.S. Pat. No. 8,106,108 and U.S. Pat. No. 5,621,052 and incorporated by reference herein. In some embodiments, an optical element may be infiltrated or layered with UV absorbing material.

In some embodiments, the luminescent compound has a Stokes shift that is less than about 120 nm, less than about 110 nm, less than about 100 nm, less than about 90 nm, less than about 80 nm, less than 50 nm, less than 30 nm, less than 20 nm, less than 10 nm, about 50 nm to about 120 nm, about 50 nm to about 110 nm, about 50 nm to about 100 nm, about 50 nm to about 90 nm, about 60 nm to about 80 nm, or about 70 nm.

In an embodiment, the luminescent compound has a narrow absorption band. The full width at half maximum (FWHM) is the width of an absorption or emission band in nanometers at the absorption or emission intensity that is half of the maximum absorption or intensity value for the band. In an embodiment, the luminescent compound has an absorption band with a FWHM value that is less than or equal to about 100 nm, less than or equal to about 90 nm, or less than or equal to about 85 nm, less than or equal to about 75 nm when dispersed in said substantially transparent matrix. The absorption peak of the luminescent compound can vary. In an embodiment, the absorption band peak of the luminescent compound is in the range of about 445 nm to about 525 nm, about 445 nm to about 505 nm, about 475 nm to about 490 nm, or about 483 nm.

In some embodiments a luminescent compound may have a high quantum yield, along with a maximum emission wavelength at the first visible color wavelength. For example, where the first visible color wavelength is green, a luminescent compound with a maximum emission in the green wavelength may be used. In some embodiments, the luminescent compound has a peak emission at a wavelength in the range of about 450 nm to about 600 nm, about 500 nm to about 580 nm, or about 520 nm to about 560 nm. Upon excitation by visual light, the luminescent compound enhances the emissive intensity within the first color wavelength. In some embodiments, the luminescent compound has a quantum yield that is greater than about 75%, about 80%, about 85%, or about 90%.

In some embodiments, the optical element further comprises a light emitting element. The light emitting element can be in optical communication with the luminescent compound to provide an excitation source for the luminescent compound. In an embodiment, the light emitting element comprises a light emitting thin film having a maximum emission peak within the absorption band range of the luminescent compound. The absorption band range includes, but is not limited to about 10 nm to about 20 nm of the absorption peak wavelength and or along the shoulder of the emissive peak spectrum. In an embodiment, the light emitting element comprises an inorganic or organic light emitting diode (LED). Examples of light emitting diodes include inorganic blue emitting LEDs, e.g., made by Nichia (Japan), organic light emitting diodes described in U.S. Patent Application Publication Nos. 2010/0326526 and 2011/0140093, and organic light emitting diodes described in U.S. patent application Ser. No. 13/166,246, the contents of each are hereby incorporated by reference in their entirety. In general, any thin film flexible light emitting element, such as edge-type LED with flexible waveguided thin flexible polymer film, can be used. In some embodiments, the optical element further comprises an optical waveguide in optical communication with the luminescent element and the light emitting element.

The optical element described herein is not limited in its form. Preferably, the optical element can be designed such that it can be placed in a known manner between a user's eye and any object or image to be perceived. In an embodiment, the optical element comprises a film. The film can have varying thickness. In an embodiment, the film is attached to a piece of eyewear. For example, the optical element can comprise a lens. The luminescent compound can be dispersed within the lens material, or it can be dispersed in a film that is attached to the lens material. In an embodiment, the lens comprises a contact lens or an eyeglass lens. A substantially transparent matrix may be composed of any suitable material.

Some optical elements may comprise a transparent matrix of polymer and a rhodamine or a rhodamine derivative as a luminescent compound, such as rhodamine 6G, wherein the polymer comprises polyvinyl alcohol or a derivative thereof comprising $C_{1-6}$ ester or $C_{1-6}$ acetal pendant groups. In some embodiments, a polyvinyl alcohol derivative may comprise repeat unit a, repeat unit b, repeat unit c, or a combination thereof.

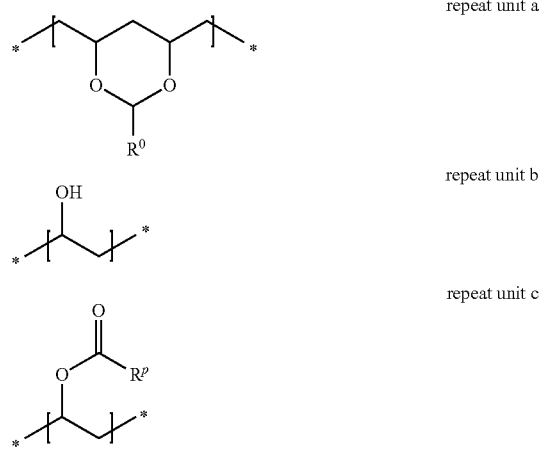

repeat unit a repeat unit b repeat unit c

With respect to repeat unit a, $R^o$ may be H or $C_{1-5}$ alkyl, such as $CH_3$, $C_2H_5$, $C_3H_7$, $C_4H_9$, $C_5H_{11}$, $C_3$-cycloalkyl, $C_4$-cycloalkyl, $C_5$-cycloalkyl, etc. In some embodiments, $R^o$ is n-propyl.

With respect to repeat unit c, $R^p$ may be H or $C_{1-5}$ alkyl, such as $CH_3$, $C_2H_5$, $C_3H_7$, $C_4H_9$, $C_5H_{11}$, $C_3$-cycloalkyl, $C_4$-cycloalkyl, $C_5$-cycloalkyl, etc. In some embodiments, $R^p$ is methyl.

In some embodiments, repeat unit a may be about 70% to about 90% or about 80% of the weight of the polymer.

In some embodiments, repeat unit b may be about 5% to about 30% or about 17% to about 20% of the weight of the polymer.

In some embodiments, repeat unit c may be about 0.01% to about 3% or about 5% of the weight of the polymer.

Some compositions may include a poly(vinyl butyral-co-vinyl alcohol-co-vinyl acetate) (PVBAA), CAS No. 27360-07-2, a polymer which includes repeat unit a, repeat unit b, and repeat unit c. In some embodiments the PVBAA has an average molecular weight in a range of about 50,000 g/mol to about 1,000,000 g/mol, about 100,000 g/mol to about 50,000 g/mol, or about 170,000 g/mol to about 250,000 g/mol. Once commercially available PVBAA is available from Sigma-Aldrich (Milwaukee, Wis. #418420), which has an average molecular weight of 170,000-250,000 g/mol, and includes 0-2.5 wt. % acetate, 17.5-20 wt % hydroxyl, and 80 wt % vinyl butyral.

Some compositions may be about 1% (w/w) to about 20%, about 2% (w/w) to about 10% (w/w), about 4% (w/w) to about 6% (w/w), or about 5% (w/w) rhodamine 6G, and about 80% (w/w) to about 99% (w/w), about 90% (w/w) to about 99% (w/), about 90% (w/w) to about 95% (w/w), about 94% (w/w) to about 96% (w/w), or about 95% (w/w) PVBAA. Some compositions may be about 5% (w/w) rhodamine 6G and about 95% (w/w) PVBAA.

In some embodiments, when the optical element comprises a film, such as a thin film, the thin film can be laminated onto other conventional optical equipment, including, but not limited to eyeglasses, contact lenses, goggles, mirrors, LED screens (cellular telephone screens, IPOD's, PDA's, etc.), computer screens and/or windshields. In an embodiment, the substantially transparent matrix material comprises a polycarbonate.

In an embodiment, the optical element comprises a substantially transparent matrix material, which can be any material useful in making a film or lens. A "substantially transparent" material is any material that a user can see through. For example, a "substantially transparent" material is capable of transmitting light such that objects or images on the other side of the material can be seen. A "substantially transparent" material can optionally have some degree of shading, and need not be completely transparent. The transparency can be calculated by first measuring the total transmittance with a multi-channel photodetector across the whole visible wavelength range, for example, from about 380 nm to about 780 nm. The transparency percentage can be reported from the arithmetic average of each transmittance percentage value recorded at 1 nm wavelength increments from about 380 nm to about 780 nm. In such an instance, there would be 400 data points used to calculate the average. In an embodiment, the optical element has a transparency that is at least about 70%, about 80%, or about 90%.

The substantially transparent matrix material can comprise a composition that includes glass or various types of polymers in various combinations in combination with a luminescent compound. It may be desirable for the material to be non-harmful and robust. In an embodiment, the substantially transparent matrix material comprises a material, including, but not limited to, glass; a thiourethane; PC; allyl diglycol carbonate (such as CR-39); a polyacrylate, such as polyacrylic acid, polyalkacrylic acid (including methacrylic acid), esters of a polyacrylic acid or a polyacrylic acid such as methyl, ethyl, propyl, isopropyl, n-butyl, sec-butyl, isobutyl, t-butyl, pentyl isomers, hexyl isomers, cyclobutyl, cyclopentyl, or cyclohexyl esters, etc., 2-hydroxyethylmethacrylate, and including polyacrylate hydrogels; polyvinylpyrrolidinone; one or more terpolymers of hexafluoroacetone-tetrafluoroethylene-ethylene (HFA/TFE/E terpolymers), PMMA, PVB, ethylene vinyl acetate, ethylene tetrafluoroethylene, a polyimide, a polystyrene, a polyurethane, organosiloxane, a poly(vinyl butyral-co-vinyl alcohol-co-vinyl acetate, and combinations thereof.

Some optical elements may comprise a substantially transparent component that is coated with a substrate layer. The substrate layer may be coated with a layer comprising a substantially transparent layer and a luminescent compound dispersed in the transparent layer. A Substrate layer may comprise any suitable polymeric material such as: poly(ethylene teraphthalate) (PET), cellulose triacetate TAC, a thiourethane; a polycarbonate (PC); allyl diglycol carbonate (such as CR-39); a polyacrylate, such as polyacrylic acid, polyalkacrylic acid (including methacrylic acid), esters of a polyacrylic acid or a polyacrylic acid such as methyl, ethyl, propyl, isopropyl, n-butyl, sec-butyl, isobutyl, t-butyl, pentyl isomers, hexyl isomers, cyclobutyl, cyclopentyl, or cyclohexyl esters, etc., 2-hydroxyethylmethacrylate, and including polyacrylate hydrogels; polyvinylpyrrolidinone; one or more terpolymers of hexafluoroacetone-tetrafluoroethylene-ethylene (HFA/TFE/E terpolymers), polymethyl methacrylate (PMMA), a polyvinyl butyral (PVB), ethylene vinyl acetate, ethylene tetrafluoroethylene, a polyimide, a polystyrene, a polyurethane, organosiloxane, a poly(vinyl butyral-co-vinyl alcohol-co-vinyl acetate, and combinations thereof.

For devices in the form of eyewear such as glasses or sunglasses, a lens or optical element may be composed of any optically suitable plastic, or they may be composed primarily of glass, or other vitreous material. Included among the suitable optical plastics are thermoplastic synthetic resins, including poly(diethylene glycol bis(allyl carbonate)); polyurethane comprising a diethylene glycol polyol; thiourethane resins from isocyanate and polythiol; acrylates such as polymers of $C_{1-6}$ alkyl esters of methacrylic acid (including methyl methacrylate, ethyl methacrylate, propyl methacrylate, butyl methacrylate, etc.), $C_{1-6}$ alkyl esters of acrylic acid (including methyl acrylate, ethyl acrylate, propyl acrylate, butyl acrylate, etc.), and related acrylic resins; polystyrenes, including polystyrene homopolymers, as well as copolymers of styrene and acrylonitrite, polybutadiene-modified polystyrene, etc.; polycarbonates; vinyl resins such as polyethylene, polyvinyl chloride, polyvinyl acetate, polyvinyl alcohol, polyvinyl butyral, etc.; ionomers and monochlorotrifluoroethylene resins; cellulose derivatives, including cellulose acetate, cellulose nitrate, ethyl cellulose, cellulose acetate butyrate, etc; epoxies; polyester resins; etc.

For devices in the form of an ocular lens, such as a soft contact lens, a hard contact lens, or an intraocular lens (referred to collectively herein as "ocular lens"), matrix materials of a lens or an optical element may include an ocular polymer.

For a softer ocular lens, such as a soft contact lens, a soft monomer may be incorporated into an ocular polymer. For harder lenses, such as hard contact lenses, a hard monomer may be incorporated into an ocular polymer. Many ocular lenses may incorporate, or may be a reaction product of a mixture comprising, a combination of soft and hard monomers. In some embodiments, an ocular lens may comprise an ocular polymer that is a product of a reaction of a mixture comprising a soft and/or a hard monomer, and may optionally further comprise a cross-linking agent, other polymerizable monomers, an initiator, and/or other materials.

Soft monomers may include hydrogel forming monomers, or monomers that form hydrogel polymers. Hydrogel polymers include polymeric systems that can absorb and retain water in an equilibrium state. Hydrogel polymers may incorporate hydrogel forming monomers including hydrophilic acrylates, such as hydroxyalkyl acrylates, hydroxyl alkyl methacrylates, acrylic acid, methacrylic acid, etc.; vinyl lactams, including optionally substituted N-vinylpyrrolidones, such as unsubstituted 1-vinyl-2-pyrrolidinone; acrylamides, such as methacrylamide and N,N-dimethylacrylamide; etc. Some hydrogel polymers may be a reaction product of polymerization reaction comprising an optional cross-linking agent and: 2-hydroxyethyl methacrylate (HEMA), HEMA and methacrylic acid; HEMA and 1-vinyl-2-pyrrolidinone; HEMA and 1-vinyl-2-pyrrolidinone and methacrylic acid; HEMA and 1-vinyl-2-pyrrolidinone and methyl methacrylate; HEMA and N-(1,1-dimethyl-3-oxobutyl)acrylamide; or 1-vinyl-2-pyrrolidinone and methyl methacrylate and allyl methacrylate.

Hard monomers include acrylate monomers that lack hydrophilic functional groups other than the $CO_2$ group of the ester, such as alkyl acrylate monomers or alkyl methacrylate monomers. Other hard monomers may include cellulose derivatives, such as cellulose acetate butyrate, and styrenes.

Hard alkyl acrylate monomers may include alkyl esters of acrylic acid, such as methyl acrylate, ethyl acrylate, propyl acrylate, butyl acrylate, pentyl acrylate, hexyl acrylate, heptyl acrylate, isobutyl acrylate, n-pentyl acrylate, tert-pentyl acrylate, hexyl acrylate, 2-methylbutyl acrylate, heptyl acrylate, octyl acrylate, 2-ethylhexyl acrylate, nonyl acrylate, decyl acrylate, dodecyl acrylate, stearyl acrylate, cyclopentyl acrylate, cyclohexyl acrylate, etc. Alkyl methacrylate monomers may include alkyl esters of methacrylic acid, such as methyl methacrylate, ethyl methacrylate, propyl methacrylate, butyl methacrylate, pentyl methacrylate, hexyl methacrylate, heptyl methacrylate, isobutyl methacrylate, n-pentyl methacrylate, tert-pentyl methacrylate, hexyl methacrylate, 2-methylbutyl methacrylate, heptyl methacrylate, octyl methacrylate, 2-ethylhexyl methacrylate, nonyl methacrylate, decyl methacrylate, dodecyl methacrylate, stearyl methacrylate, cyclopentyl methacrylate, cyclohexyl methacrylate, isopropyl methacrylate, s-butyl methacrylate, t-butyl methacrylate, 3,3,5-trimethylcyclohexyl methacrylate t-butyl acrylate, etc. In some alkyl acrylates or alkyl methacrylates, the alkyl group of the alkyl ester may contain 1, 2, 3, or 4 carbon atoms. Some ocular lens polymers are products of a polymerization reaction comprising methyl acrylate, ethyl acrylate, propyl acrylate, butyl acrylate, methyl methacrylate, ethyl methacrylate, propyl methacrylate, or butyl methacrylate.

For some ocular lenses, repeating units derived from an alkyl acrylate and/or an alkyl methacrylate are at least about 10%, about 20%, about 30%, and may be up to about 90%, about 95%, about 99%, or may approach about 100% of the weight of an ocular polymer.

Other hard acrylate monomers may include phenyl methacrylate, tetrahydrofurfuryl acrylate, tetrahydrofurfuryl methacrylate, allyl methacrylate, etc.

Examples of a cross-linking agent may include: ethyleneglycol diacrylate, butanediol diacrylate, hexanediol diacrylate, hexanediol dimethacrylate, diethyleneglycol diacrylate, triethyleneglycol diacrylate, propyleneglycol diacrylate, dipropyleneglycol diacrylate, divinylbenzene, allyl acrylate, vinyl acrylate, trimethylolpropane triacrylate, acryloyloxyethyl acrylate, diallyl fumarate, diallyl phthalate, diallyl adipate, divinyl adipate, α-methylene-N-vinyl pyrrolidone, 4-vinylbenzyl acrylate, 3-vinylbenzyl acrylate, 2,2-bis(acryloyloxyphenyl)hexafluoropropane, 2,2-bis(acryloyloxyphenyl)propane, 1,2-bis(2-(acryloyloxyhexafluoroisopropyl)benzene, 1,3-bis(2-(acryloyloxyhexafluoroisopropyl)benzene, 1,4-bis(2-(acryloyloxyhexafluoroisopropyl)benzene, 1,2-bis(2-(acryloyloxyisopropyl)benzene, 1,3-bis(2-(acryloyloxyisopropyl)benzene, 1,4-bis(2-(acryloyloxyisopropyl)benzene, ethyleneglycol dimethacrylate, butanediol dimethacrylate, diethyleneglycol dimethacrylate, triethyleneglycol dimethacrylate, propyleneglycol dimethacrylate, dipropyleneglycol dimethacrylate, divinylbenzene, allyl methacrylate, vinyl methacrylate, trimethylolpropane trimethacrylate, methacryloyloxyethyl methacrylate, 4-vinylbenzyl methacrylate, 3-vinylbenzyl methacrylate, 2,2-bis(methacryloyloxyphenyl)hexafluoropropane, 2,2-bis(methacryloyloxyphenyl)propane, 1,2-bis(2-(methacryloyloxyhexafluoroisopropyl)benzene, 1,3-bis(2-

(methacryloyloxyhexafluoroisopropyl)benzene, 1,4-bis(2-(methacryloyloxyhexafluoroisopropyl)benzene, 1,2-bis(2-(methacryloyloxyisopropyl)benzene, 1,3-bis(2-(methacryloyloxyisopropyl)benzene, 1,4-bis(2-(methacryloyloxyisopropyl)benzene, N,N'-bis-acryloylcystamine, N,N'-bis-methacryloylcystamine, methylene bis-acrylamide, or methylene bis-methacryloylcystamine. Some acrylic polymers are a product of a polymerization reaction of a mixture that includes ethyleneglycol diacrylate, butanediol diacrylate, 4-vinylbenzyl methacrylate, ethyleneglycol dimethacrylate, butanediol dimethacrylate, and/or 4-vinylbenzyl methacrylate as a crosslinker. For some acrylic polymers, the cross-linking agent is about 0.001% to 15% by weight or about 0.1% to 10% of the weight of a polymerization reaction mixture. In some embodiments, excessive use of a cross-linking agent may cause an ocular lens to be fragile.

One or more additional polymerizable monomers may optionally be added to a polymerization reaction mixture. In some embodiments, polymerizable monomers that are not acrylate monomers may be less than about 90% by weight, about 80% by weight, about 50% by weight, about 30% by weight, about 20% by weight, about 10% by weight, or about 5% by weight of the polymerization reaction mixture.

A specific example of a hydrogel-forming monomer mixture is polymacon, composed primarily of 2-hydroxyethylmethacrylate with a small amount of diethyleneglycol dimethacrylate as a crosslinking monomer.

Examples of additional polymerizable monomers may include a silicon-containing methacrylate monomer, a derivative of a silicon-containing styrene, a derivative of a fluorine-containing styrene, a fluorine-containing acrylate monomer, a silicon-containing macromonomer, etc. These types of polymerizable monomers may improve oxygen transmission and/or contamination resistance in an ocular polymer. A styrene may be added to improve the mechanical strength and hardness of an ophthalmic lens such as an ocular lens.

Silicon-containing acrylate monomers may include, pentamethyldisiloxanylmethyl acrylate, pentamethyldisiloxanylpropyl acrylate, methylbis(trimethylsiloxy)silylpropyl acrylate, tris(trimethylsiloxy)silylpropyl acrylate, mono[methyl-bis(trimethylsiloxy)siloxy]bis(trimethylsiloxy)silylpropyl acrylate, tris[methyl-bis(trimethylsiloxy)siloxy]silylpropyl acrylate, methyl-bis(trimethylsiloxy)silylpropylglycerol acrylate, tris(trimethylsiloxy)silylpropylglycerol acrylate, mono[methyl-bis(trimethylsiloxy)siloxy]bis(trimethylsiloxy)silylpropylglycerol acrylate, trimethylsilylethyltetramethyldisiloxanylpropylglycerol acrylate, trimethylsilylmethyl acrylate, trimethylsilylpropyl acrylate, trimethylsilylpropylglycerol acrylate, pentamethyldisiloxanyl propylglycerol acrylate, methylbis(trimethylsiloxy)silylethyltetramethyldisiloxanylmethyl acrylate, tetramethyltriisopropylcyclotetrasiloxanylpropyl acrylate, tetramethyltriisopropylcyclotetrasiloxybis(trimethylsiloxy)silylpropyl acrylate pentamethyldisiloxanylmethyl methacrylate, pentamethyldisiloxanylpropyl methacrylate, methylbis(trimethylsiloxy)silylpropyl methacrylate, tris(trimethylsiloxy)silylpropyl methacrylate, mono[methyl-bis(trimethylsiloxy)siloxy]bis(trimethylsiloxy)silylpropyl methacrylate, tris[methyl-bis(trimethylsiloxy)siloxy]silylpropyl methacrylate, methyl-bis(trimethylsiloxy)silylpropylglycerol methacrylate, tris(trimethylsiloxy)silylpropylglycerol methacrylate, mono[methyl-bis(trimethylsiloxy)siloxy]bis(trimethylsiloxy)silylpropylglycerol methacrylate, trimethylsilylethyltetramethyldisiloxanylpropylglycerol methacrylate, trimethylsilylmethyl methacrylate, trimethylsilylpropyl methacrylate, trimethylsilylpropylglycerol methacrylate, pentamethyldisiloxanyl propylglycerol methacrylate, methylbis(trimethylsiloxy)silylethyltetramethyldisiloxanylmethyl methacrylate, tetramethyltriisopropylcyclotetrasiloxanylpropyl methacrylate, tetramethyltriisopropylcyclotetrasiloxybis(trimethylsiloxy)silylpropyl methacrylate, etc.

Examples of silicon-containing derivatives of a styrene may include trimethylsilylstyrene, tris(trimethylsiloxy)silylstyrene, etc.

A silicon-containing macromonomer includes a macromonomer containing silicon (Si), such as a polysiloxane macro, having polymerzible groups at both ends of a polysiloxane macromer, bonded to a vinyl-containing monomer by an urethane bond.

Some polymerization reaction mixtures may include a silicone-containing monomer which may react in the polymerization mixture to form a silicone hydrogel copolymer. Examples of silicone-containing monomers include: monomers including a single activated double bond, such as methacryloxypropyl tris(trimethylsiloxy)silane, pentamethyldisiloxanyl methylmethacrylate, tris(trimethylsiloxy) methacryloxy propylsilane, methyldi(trimethylsiloxy) methacryloxymethyl silane, 3-[tris(trimethylsiloxy)silyl] propyl vinyl carbamate, and 3-[tris(trimethylsiloxy)silyl] propyl vinyl carbonate; and multifunctional ethylenically "end-capped" siloxane-containing monomers, especially difunctional monomers having two activated double bonds.

Examples of fluorine-containing derivatives of a styrene may include o-fluorostyrene, m-fluorostyrene, p-fluorostyrene, trifluorostyrene, perfluorostyrene, p-trifluoromethylstyrene, o-trifluoromethylstyrene, and m-trifluoromethylstyrene, etc.

Examples of fluorine-containing acrylate monomers include, 2,2,2-trifluoroethyl acrylate, 2,2,3,3-tetrafluoropropyl acrylate, 2,2,3,3,3-pentafluoropropyl acrylate, 2,2,2-trifluoro-1-trifluoromethylethyl acrylate, 2,2,3,3-tetrafluoro-tert-pentyl acrylate, 2,2,3,4,4,4-hexafluorobutyl acrylate, 2,2,3,3,4,4-hexafluorobutyl acrylate, 2,2,3,4,4,4-hexafluoro-tert-hexyl acrylate, 2,2,3,3,4,4-heptafluorobutyl acrylate, 2,2,3,3,4,4,5,5-octafluoropentyl acrylate, 3,3,4,4,5,5,6,6-octafluorohexyl acrylate, 2,3,4,5,5,5-hexafluoro-2,4-bis(trifluoromethyl)pentyl acrylate, 2,2,3,3,4,4,5,5-nonafluoropentyl acrylate, 2,2,3,3,4,4,5,5,6,6,7,7-dodecafluoroheptyl acrylate, 3,3,4,4,5,5,6,6,7,7,8,8-dodecafluorooctyl acrylate, 3,3,4,4,5,5,6,6,7,7,8,8-tridecafluorooctyl acrylate, 2,2,3,3,4,4,5,5,6,6,7,7,7-tridecafluoroheptyl acrylate, 3,3,4,4,5,5,6,6,7,7,8,8,9,9,10,10-hexadecafluorodecyl acrylate, 3,3,4,4,5,5,6,6,7,7,8,8,9,9,10,10,10-heptadecafluorodecyl acrylate, 3,3,4,4,5,5,6,6,7,7,8,8,9,9,10,10,11,11-octadecafluoroundecyl acrylate, 3,3,4,4,5,5,6,6,7,7,8,8,9,9,10,10,11,11-nonadecafluoroundecyl acrylate, 3,3,4,4,5,5,6,6,7,7,8,8,9,9,10,10,11,11,12,12-eicosafluorododecyl acrylate, 2-hydroxy-4,4,5,5,6,7,7,7-octafluoro-6-trifluoromethylheptyl acrylate, 2-hydroxy-4,4,5,5,6,6,7,7,8,9,9,9-dodecafluoro-8-trifluoromethylnonyl acrylate, and 2-hydroxy-4,4,5,5,6,6,7,7,8,8,9,9,10,11,11,11-hexadecafluoro-10-trifluoro-methylundecyl acrylate, 2,2,2-trifluoroethyl methacrylate, 2,2,3,3-tetrafluoropropyl methacrylate, 2,2,3,3,3-pentafluoropropyl methacrylate, 2,2,2-trifluoro-1-trifluoromethylethyl meth acrylate, 2,2,3,3-tetrafluoro-tert-pentyl methacrylate, 2,2,3,4,4,4-hexafluorobutyl methacrylate, 2,2,3,3,4,4-hexafluorobutyl methacrylate, 2,2,3,4,4,4-hexafluoro-tert-hexyl methacrylate, 2,2,3,3,4,4-heptafluorobutyl methacrylate, 2,2,3,3,4,4,5,5-octafluoropentyl methacrylate, 3,3,4,4,5,5,6,6-octafluorohexyl methacrylate, 2,3,4,5,5,5-hexafluoro-2,4-bis(trifluoromethyl)pentyl methacrylate, 2,2,3,3,4,4,5,5- nonafluoropentyl methacrylate, 2,2,3,3,4,4,5,5,6,6,7,7-dodecafluoroheptyl methacrylate, 3,3,4,4,5,5,6,6,7,7,8,8-dodecafluorooctyl methacrylate, 3,3,4,4,5,5,6,6,7,7,8,8,8-tridecafluorooctyl methacrylate, 2,2,3,3,4,4,5,5,6,6,7,7,7-tridecafluoroheptyl methacrylate, 3,3,4,4,5,5,6,6,7,7,8,8,9,9,10,10-hexadecafluorodecyl methacrylate, 3,3,4,4,5,5,6,6,7,7,8,8,9,9,10,10,10-heptadecafluorodecyl methacrylate, 3,3,4,4,5,5,6,6,7,7,8,8,9,9,10,10,11,11-octadecafluoroundecyl methacrylate, 3,3,4,4,5,5,6,6,7,7,8,8,9,9,10,10,11,11,11-nonadecafluoroundecyl methacrylate, 3,3,4,4,5,5,6,6,7,7,8,8,9,9,10,10,11,11,12,12-eicosafluorododecyl methacrylate, 2-hydroxy-4,4,5,5,6,7,7,7-octafluoro-6-trifluoromethylheptyl methacrylate, 2-hydroxy-4,4,5,5,6,6,7,7,8,9,9,9-dodecafluoro-8-trifluoromethylnonyl methacrylate, and 2-hydroxy-4,4,5,5,6,6,7,7,8,8,9,9,10,11,11,11-hexadecafluoro-10-trifluoro-methylundecyl methacrylate, etc.

Examples of a styrene include unsubstituted styrene, o-methylstyrene, m-methylstyrene, p-methylstyrene, p-ethylstyrene, o-hydroxystyrene, m-hydroxystyrene, p-hydroxystyrene, trimethylstyrene, tert-butylstyrene, perbromostyrene, dimethylaminostyrene, α-methylstyrene, etc.

Polymerization of a reaction mixture may be accomplished by a heat polymerization. For example, a polymerization reaction mixture may be heated to an elevated temperature, such as about 50° C. to about 300° C., about 100° C. to about 200° C., or about 100° C. to about 150° C. when a polymerization initiator is present in a polymerization reaction mixture. Heat polymerization may reduce discoloration or fading after the polymerization as compared to other polymerization methods. Alternatively, a polymerization reaction may be photopolymerized, such as by exposure to an electromagnetic radiation such as microwave, an ultraviolet radiation, a radiant ray (γ-ray), etc.

A polymerization initiator may be selected based on the method of polymerization to be employed. For example, if the heat polymerization is employed, a radical polymerization initiator may be used. If a polymerization is achieved by the exposure to the electromagnetic radiation, a photopolymerization initiator or a photosensitizer may be used. Polymerization may also be initiated by a base or an acid catalyst, or by an electrophilic agent or a nucleophilic agent.

Any suitable radical polymerization initiator may be used. Examples of radical polymerization initiators may include azobisisobutyronitrile, azobis-2,4-dimethylvaleronitrile, benzoyl peroxide, dibenzoyl peroxide, benzoin methyl ether, tert-butyl hydroperoxide, cumene hydroperoxide, etc.

Any suitable photopolymerization initiator may be used in a photopolymerization reaction of a polymerization reaction mixture. Examples of photopolymerization initiators include: benzoin based photopolymerization initiators such as methylorthobenzoylbenzoate, methylbenzoylformate, benzoinmethylether, benzomethylether, benzoinisopropylether, benzoinisobutylether, benzoin-n-butylether, etc.; phenone photopolymerization initiators such as 2-hydroxy-2-methyl-1-phenylpropane-1-one, p-isopropyl-α-hydroxyisobutylphenone, p-tert-butyltrichloroacetophenone, 2,2-dimethoxy-2-phenylacetophenone, α,α-dichloro-4-phenoxyacetophenone, N,N-tetraethyl-4,4-diaminobenzophenone, etc.; 1-hydroxycyclohexylphenylketone; 1-phenyl-1,2-propanedione-2-(o-ethoxycarbonyl)oxime; thioxanthone photopolymerization initiator such as 2-chlorothioxanthone, 2-methylthioxanthone etc.; dibenzosuberone; 2-ethylanthraquinone; benzophenoneacrylate; benzophenone; benzyl; etc.

Any suitable amount of polymerization initiator may be used, such as at least about 0.005 parts by weight or at least about 0.01 parts by weight per 100 parts by weight of a polymer reaction mixture. In some embodiments, the amount of polymerization initiator may be less than about 2 parts by weight, or 1 part by weight per 100 parts by weight of a polymerization reaction mixture.

Any of a number of methods may be used to form an ocular lens. For example, a cutting method may be used. In a cutting method, a polymer may be formed into a desired configuration by a mechanical processing method such as cutting, grinding, etc. An ocular lens may also be formed using a molding method. In a molding method, a polymerization reaction mixture may be placed into a mold cavity, and a desired shape may be obtained by reaction of the polymerization reaction mixture in the mold cavity. Other forming methods may also be used. Additionally, molding and cutting methods may be combined.

A luminescent compound may be incorporated into an ocular polymer when casting a lens, or a finished lens can treated with a luminescent compound, such as by soaking in or coating with solution containing a luminescent compound.

Optionally, a mixture of monomers to be polymerized into a hydrogel copolymer may include a silicone-containing monomer in order to form a silicone hydrogel copolymer. Examples of silicone-containing monomers include: monomers including a single activated double bond, such as methacryloxypropyl tris(trimethylsiloxy)silane, pentamethyldisiloxanyl methylmethacrylate, tris(trimethylsiloxy) methacryloxy propylsilane, methyldi(trimethylsiloxy) methacryloxymethyl silane, 3-[tris(trimethylsiloxy)silyl] propyl vinyl carbamate, and 3-[tris(trimethylsiloxy)silyl] propyl vinyl carbonate; and multifunctional ethylenically "end-capped" siloxane-containing monomers, especially difunctional monomers having two activated double bonds.

In some embodiments, an optical element of a device may comprise a coating, such as a scratch resistant coating, wherein a substantially transparent matrix comprises a scratch resistant material, and a luminescent material may be dispersed in the scratch resistant material. Examples of a scratch resistant material such as cellulose acetate butyrate, cellulose nitrate, cellulose triacetate, a hard acrylate (such as a hard acrylate described above), a polyalkylene such as polyethylene or polypropylene, poly(acrylonitrile), poly(vinyl acetate), poly(vinyl chloride), an optionally substituted polystyrene, polybutadiene, nylon, a vinyl chloride-vinyl acetate copolymer, a polycarbonate, a styrene-butadiene copolymer resin, a polyurethane, such as a lightly crosslinked thermoplastic polyurethane, a polyurea urethane, a polysiloxane, a polysilane, a fluoropolymer such as a polymer or copolymer of fluoroethylene, difluoroethylene, trifluoroethylene, tetrafluoroethylene (e.g. poly(tetrafluoroethylene)), an epoxy functional alkoxy silane, an silicon oxynitride PECVD film, a metal oxide, etc.

Any suitable polycarbonate may be used, such as a homo polycarbonate, a co-polycarbonate, a branched polycarbonate, or a mixture thereof. Some polycarbonates may be prepared by reaction of a carbonic acid derivative, such as phosgene, and a dihydroxy compound. Useful dihydroxy compounds include bisphenol compounds which may be represented by Formula S:

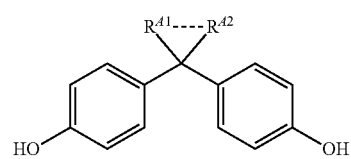

Formula S $R^{A1}$ may be H, or $C_{1-12}$ alkyl, including: linear or branched alkyl having a formula $C_aH_{a+1}$ or $C_aH_a$, or cycloalkyl having a formula $C_aH_{a-1}$ or $C_aH_{a-2}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc.

$R^{A2}$ may be H, or $C_{1-12}$ alkyl, including: linear or branched alkyl having a formula $C_aH_{a+1}$ or $C_aH_a$, or cycloalkyl having a formula $C_aH_{a-1}$ or $C_aH_{a-2}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc.

In some embodiments $R^{A1}$ and $R^{A2}$ are hydrogen, methyl, propyl, or phenyl, or

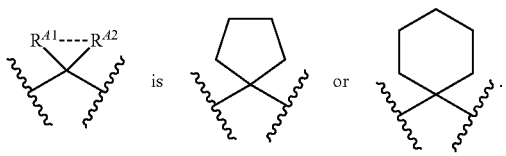

In some embodiments $R^{A1}$ and $R^{A2}$ are methyl. A polycarbonate may have any suitable molecular weight. In some embodiments a polycarbonate may have a molecular weight of about 10,000 g/mol to about 200,000 g/mol or about 20,000 g/mol to about 80,000 g/mol.

Generally, a polyurethane includes a polymer that may be formed by reaction of a polyisocyanate and a polyol. A polyurea urethane includes a polymer that may be formed by reaction of a polyisocyanate, a polyol, and a polyamine.

Polyisocyanates include organic isocyanates having 2 or more isocyanate functional groups. Some polyisocyanates may have, on average, about 2 to about 3 isocyanate functional groups per molecule. A polyisocyanate may be an aliphatic polyisocyanate, a cycloaliphatic polyisocyanate wherein one or more of the isocyanato groups are attached directly to the cycloaliphatic ring, a cycloaliphatic polyisocyanate wherein one or more of the isocyanato groups are not attached directly to the cycloaliphatic ring, an aromatic polyisocyanate wherein one or more of the isocyanate groups are attached directly to the aromatic ring, and aromatic polyisocyanates wherein one or more of the isocyanato groups are not attached directly to the aromatic ring, or a mixture thereof. Non-limiting examples of suitable polyisocyanates include tetramethylene-1,4-diisocyanate, hexamethylene-1,6-diisocyanate, 2,2,4-trimethylhexane-1,6-diisocyanate, cyclobutane-1,3-diisocyanate, cyclohexane-1,3-diisocyanate, cyclohexane-1,4-diisocyanate, methyl cyclohexyl diisocyanate, e.g., 2,4- and 2,6-methyl cyclohexyl diisocyanate, isophorone diisocyanate, the isomers and mixtures of isomers of 4,4'-methylene-bis(cyclohexyl isocyanate), e.g., the trans-trans, cis-cis and cis-trans isomers, hexahydrotoluene-2,4-diisocyanate, hexahydrotoluene-2,6-diisocyanate, hexahydrophenylene-1,3-diisocyanate, hexahydrophenylene-1,4-diisocyanate, hexahydrophenylene-1,4-diisocyanate, phenyl cyclohexylmethane diisocyanate, etc.

A polyamine may be any compound comprising two or more primary (e.g. $-NH_2$) and/or secondary amino functional groups, such as 2 primary amino functional groups, 2 secondary amino functional groups, or 1 primary amino functional group and 1 secondary amino functional group. Some examples of suitable polyamines include aliphatic polyamines such as aliphatic diamines having from 2 to 10 carbon atoms, e.g. 1,2-ethane diamine, 1,3-propane diamine, 1,4-butane diamine, 1,5-pentane diamine, 1,6-hexane diamine, 1,8-octane diamine, and 1,10-decane diamine, etc.; cycloaliphatic polyamines; aromatic polyamines, such as 1,2-benzene diamine, 1,3-benzene diamine, 1,4-benzene diamine, 1,5-naphthalene diamine, 1,8-naphthalene diamine, 2,4-toluene diamine, 2,5-toluene diamine, 3,3'-dimethyl-4,4'-biphenyldiamine, 4,4'-methylene bis(aniline), 4,4'-methylene bis(2-chloroaniline); dialkyl toluene diamines in which the alkyl groups each contain from 1 to 3 carbon atoms, such as 3,5-dimethyl-2,4-toluene diamine, 3,5-dimethyl-2,6-toluene diamine, 3,5-diethyl-2,4-toluene diamine, 3,5-diethyl-2,6-toluene diamine, 3,5-diisopropyl-2,4-toluene diamine, 3,5-diisopropyl-2,6-toluene diamine, etc.; 4,4'-methylene-bis(dialkylaniline) in which the alkyl groups each contain from 1 to 3 carbon atoms, such as 4,4'-methylene bis(2,6-dimethylaniline), 4,4'-methylene bis(2,6-diethylaniline), 4,4'-methylene bis(2-ethyl-6-methylaniline), 4,4'-methylene bis(2,6-diisopropylaniline), 4,4'-methylene bis(2-isopropyl-6-methylaniline) and 4,4'-methylene bis(2,6-diethyl-3-chloroaniline), etc. Dialkyl toluene diamines may be sold as isomeric mixtures, e.g., an isomeric mixture of 3,5-diethyl-2,4-toluene diamine and 3,5-diethyl-2,6-toluene diamine. Polyamines may also contain more than two amino groups, such as diethylenetriamine, triethylenetetramine, and tetraethylenepentamine.

A polyurethane or a polyurea urethane may be a polyether-based polyurethane or polyurea urethane, a polycarbonate-based polyurethane or polyurea urethane, or a polyester-based polyurethane or polyurea urethane, referring to the type of polyol used to form the polyurethane or polyurea urethane.

Examples of polyether polyols include, but are not limited to, polyoxyalkylene polyols, and polyalkoxylated polyols. Polyoxyalkylene polyols include polyols that may be prepared by reacting an alkylene oxide, or a mixture of alkylene oxides, using with a polyhydric initiator or a mixture of polyhydric initiators, such as ethylene glycol, propylene glycol, glycerol, sorbitol and the like. Examples of alkylene oxides include ethylene oxide, propylene oxide, butylene oxide, amylene oxide, aralkylene oxides, e.g., styrene oxide, mixtures of ethylene oxide and propylene oxide, etc. Polyoxyalkylene polyols prepared with mixtures of alkylene oxide can be prepared using random or step-wise oxyalkylation. Examples of such polyoxyalkylene polyols include polyoxyethylene, e.g., polyethylene glycol, polyoxypropylene, e.g., polypropylene glycol. Polyalkoxylated polyols include polyols that may be prepared by reacting a diol such as a $C_{1-8}$ alkylene diol, a dihydroxybenzene, etc., with an alkylene oxide such as ethylene oxide, propylene oxide, butylene oxide, etc.

A polyether polyol may have any suitable molecular weight. For example, some polyether polyols may have a weight average molecular weight of about 500 g/mol to about 3000 g/mol, about 650 g/mol to about 2000 g/mol, about 650 g/mol to about 1400 g/mol, about 850 g/mol to about 1000 g/mol, or about 1200 g/mol.

Polycarbonate polyols include polyols that may be prepared by reaction of an organic glycol, e.g., a diol, such a glycol, and a dialkyl carbonate. Some polycarbonate polyols may be represented by a formula $H-(O-C(O)-O-(CH_2)_m)_n-OH$, wherein m is 2, 3, 4, 5, 6, 7, 8, 9, or 10, and n is 4 to 24, 4 to 10, or 5 to 7. In some embodiments, a dialkyl carbonate is a polyhexamethylene carbonate, where m is 6. A polycarbonate polyol may have any suitable molecular weight, such as a number average molecular weight of about 500 g/mol to 3500 g/mol or about 650 g/mol to about 1000 g/mol.

A glycol includes low molecular weight polyols, e.g., polyols having a molecular weight of less than 500 g/mol, such as low molecular weight diols and triols. Some glycols contain 2 to 16, 2 to 6, or 10 carbon atoms. Non-limiting examples of glycols include: ethylene glycol, propylene glycol, diethylene glycol, triethylene glycol, tetraethylene glycol, dipropylene glycol, tripropylene glycol, 1,2-, 1,3- and 1,4-butanediol, 2,2,4-trimethyl-1,3-pentanediol, 2-methyl-1,3-pentanediol, 1,3-, 2,4- and 1,5-pentanediol, 2,5- and 1,6-hexanediol, 2,4-heptanediol, 2-ethyl-1,3-hexanediol, 2,2-dimethyl-1,3-propanediol, 1,8-octanediol, 1,9-nonanediol, 1,10-decanediol, 1,4-cyclohexanediol, 1,4-cyclohexanedimethanol, 1,2-bis (hydroxyethyl)-cyclohexane, glycerin, tetramethylolmethane, e.g., pentaerythritol, trimethylolethane, and trimethylolpropane. Other isomers of these glycols may also be used. The amount of glycol used in relation to a polyether polyol and/or polycarbonate polyol component may vary from 3 to 20 weight percent.

Polyester polyols include polyols that may be prepared by esterification of saturated dicarboxylic acids or anhydrides thereof (or combinations of acids and anhydrides) with polyhydric alcohols; polylactones, e.g., polycaprolactone and polyvalerolactone, which may be prepared by polymerizing a lactone, such as epsilon caprolactone or delta-valerolactone, in the presence of minor amounts of difunctional active hydrogen compounds, such as water or a low molecular glycol, e.g., 1,4-butane diol.

Saturated dicarboxylic acids include those containing from 4 to 10 carbon atoms or 6 to 9 carbon atoms, such as succinic acid, glutaric acid, adipic acid, pimelic acid, suberic acid, azelaic acid, sebacic acid, etc.

Polyhydric alcohols include aliphatic alcohols containing at least two hydroxy groups, e.g., straight chain glycols containing from 2 to 10 or 4 to 8 carbon atoms. Non-limiting examples include the glycols described above. In some embodiments, a polyhydric alcohol is 1,4-butane diol.

A polyester polyol may have any suitable molecular weight, such as a number average molecular weight of about 1000 g/mol to about 3000 g/mol or about 1000 g/mol to about 2000 g/mol. Non-limiting examples of polyester polyols include poly(butane diol-1,4-adipate), poly(butane diol-1,4-succinate), poly(butane diol-1,4-glutarate), poly(butane diol-1,4-pimelate), poly(butane diol-1,4-suberate), poly(butane diol-1,4-azelate), poly(butane diol-1,4-sebacate) and poly (epsilon caprolactone).

A scratch resistant coating may include from 0 to 20 weight percent or about 1 to about 90 weight percent based on the total weight of the composition, of a metal oxide such as silicon dioxide, aluminum oxide, antimony oxide, tin oxide, titanium oxide, zirconium oxide, etc., or a mixture thereof.

A scratch resistant coating have any suitable thickness, such as a thickness of about 1 mil to about 20 mils (about 0.025 mm to about 0.5 mm) or about 5 mil to about 10 mils (about 0.125 mm to about 0.25 mm). A scratch resistant coating may be directly applied to another material, or may be applied using an adhesive layer, such as a substantially transparent layer having a thickness less than 25 microns, about 0.1 micron to about 10 microns, about 0.1 microns to about 5 microns, or about 1 micron.

The resistance of a coating to scratching may be measured by the rotary steel wool test, which involves subjecting the coating to five revolutions of a pad of 0000 grade steel wool at a defined pressure, usually 12 or 24 psi. The scratching abrasion resistance is rated by measuring the increase in haze from the abrasion. Test methods such as ASTM D-1044 have been developed for optically measuring the resistance of transparent plastic materials to abrasion. Other standard tests for abrasion resistance are the Taber abrasion test described in ASTM D-1004-56.

In many applications, toughness and resistance to impact may be important for a scratch resistant coating. The toughness or impact abrasion resistance of a coating is commonly measured by the "falling sand" test (ASTM D968-51). A coating which has good scratch abrasion resistance may not necessarily have good impact abrasion resistance. With the falling sand test, sand is poured onto a coating from a predetermined height, while the thickness of the coating is observed. The results are expressed in terms of the number of liters of sand required to abrade away one tenth of a mil of the coating thickness.

An optical element may be integrated into an electronic device that comprises an electronic display, an optical element, and a touch screen component. An example of such a device 10 is depicted in FIG. 2. In this type of device, touch screen component 30 may be disposed over electronic display 20. Optical element 15 is also included. Optical element 15 may be disposed over touch screen component 30, as shown in FIG. 2, or optical element 15 may be disposed between electronic display 20 and touch screen component 30, as shown in FIG. 3, or in another position that allows light from electronic display 20 to pass through optical element 15. Touch screen element 30 comprises first conductive layer 40, second conductive layer 50, and spacer 60 disposed between first conductive layer 40 and second conductive layer 50. As shown in FIG. 2A, when there is no contact between a user and device 10, there is no electrical contact between first conductive layer 40 and second conductive layer 50. As shown in FIG. 2B, contact 80 by a user can cause first conductive layer 40 to contact second conductive layer 50, which may create electrical contact between first conductive layer 40 and second conductive layer 50. This may allow current to flow between first conductive layer 40 and second conductive layer 50. Thus, the touch screen component may act as an on/off switch that is sensitive to a user's touch. Light 70 emitted from display 20 passes through touch screen component 30 and passes through optical element 15. Optical element 30 may modify a color of light 70 from display 20.

As depicted in FIG. 4, a touch screen component, e.g. touch screen component 30, may further comprise a first support layer, such as first support layer 90. First support layer 90 may be positioned so that first conductive layer 40 is disposed between spacer 60 and first support layer 90. Additionally a touch screen component may further comprise a second support layer, e.g. second support layer 100. Second support layer 100 may be positioned so that second conductive layer 50 is disposed between spacer 60 and second support layer 100. As depicted in FIG. 5, a touch screen component may also comprise a first dielectric layer, such as first dielectric layer 110, which may be disposed between first conductive layer 40 and first support layer 90. Touch screen component 30 may also comprise a second dielectric layer, such as second dielectric layer 120, which may be disposed between second conductive layer 50 and second support layer 100.

A touch screen element, such as touch screen element 30, should be sufficiently transparent for a display, such as display 20, to be viewed through the touch screen element.

A conductive layer, such as first conductive layer 40 or second conductive layer 50, may be composed of any conductive material. A first conductive layer and a second conductive layer may be composed of the same material, or may be composed of different material. Examples of conductive materials that may be used include, but are not limited to, metals such as gold, silver, platinum, palladium, copper, aluminum, nickel, chromium, titanium, iron, cobalt, tin etc., and alloys of these; metal oxides, such as indium oxide, tin oxide, titanium oxide, cadmium oxide, and mixtures of these. Other metal compounds, such as copper iodine, may also be used. In some embodiments, a conductive layer comprises indium oxide containing tin oxide, or tin oxide containing antimony. A conductive layer may have any thickness that allows the film to be sufficiently conductive and sufficiently transparent, such as about 10 nm to about 300 nm.

A spacer, e.g. spacer 60, may be a vacuum, or may be composed of any nonconductive material, such as air, nitrogen, argon, or another inert gas. A spacer may be of any suitable thickness, such as in about 10 µm to about 500 µm, about 100 µm to about 200 µm, or about 150 µm.

A support layer may be any layer that facilitates the desired function of a conductive layer. A first support layer, e.g. first support layer 90 and a second support later, e.g. second support layer 100, may be the same or different, and make may be composed of the same or different materials. Examples of suitable support materials include but are not limited to polyester-based resins, acetate-based resins, polyethersulfone-based resins, polycarbonate-based resins, polyamide-based resins, polyimide-based resins, polyolefin-based resins, acrylate-based resins, polyvinyl chloride-based resins, polystyrene-based resins, polyvinyl alcohol-based resins, poly phenylene sulfide-based resins, polyvinylidene chloride-based resins, etc. In some embodiments a support layer comprises a polyester-based resin, a polycarbonate-based resin, or a polyolefin-based resin. A support later may have any suitable thickness, such as about 75 µm to about 400 µm, about 100 µm to about 200 µm, about 2 µm to about 300 µm, or about 10 µm to about 130 µm.

A dielectric layer may be composed of any dielectric material. A first dielectric layer, e.g. first dielectric layer 110, and a second dielectric layer, e.g. second dielectric layer 120, may be the same or different, and may be composed of the same or different materials. Non-limiting examples include NaF, $Na_3AlF_6$, LiF, $MgF_2$, $CaF_2$, $BaF_2$, $SiO_2$, $LaF_3$, $CeF_3$, $Al_2O_3$, etc. A dielectric layer may have any suitable thickness, such as about 10 nm to about 300 nm, about 10 nm to about 200 nm, about 10 nm to about 120 nm, or about 15 nm to about 60 nm.

The optical elements described herein are useful in methods for correcting visual insensitivity in a mammal. In an embodiment, the method comprises identifying an individual having a visual insensitivity between a first visible color wavelength and a second visible color wavelength. In an embodiment, the method comprises selecting an optical element as described herein that corrects the visual insensitivity. In an embodiment, the method comprises providing or arranging to provide the optical element to the individual. In an embodiment, the visual insensitivity comprises deuteranomaly.

In one embodiment, identifying an individual having a visual insensitivity between a first visible color wavelength and a second visible color wavelength includes genotype determination. For example, identifying an individual having a visual insensitivity can include using a sampling kit having at least a medical subject sampling swab used in conjunction with amino acid sequencing. Comparison to standardized sequence listings (Neitz, Jay, et al, The genetics of normal and defective color vision, Vision Res. 51 (2011):633-651; Neitz, Maureen, et al, Molecular Genetics of Color Vision and Color Vision Defects, Arch Ophthalmol 118:691-700 (2000)) can provide the geneotypic information regarding the conformity or non-conformity of the subject's amino acid sequence with normal or dysfunctional sequences. Any suitable sequencing procedure and determination is appropriate to make such determination, see for example U.S. Pat. No. 5,837,461, which is incorporated by reference in its entirety. The diagnosis of cone-photoreceptor-based vision disorders by these methods can involve the use of standard molecular biology methods, including the polymerase chain reaction (PCR), to examine the identities of all or a subset of at least 18 dimorphic nucleotide positions among the red and green photopigment genes. The pattern of nucleotide differences predicts the presence or absence of vision disorder. Different patterns of nucleotide identities correspond to different disorders and different degrees of severity within one class of disorder.

In one exemplary method, the test determines the amino acids specified at positions 65, 111, and 116 in exon 2; 153, 171, 174, 178, and 180 in exon 3; 230, 233, and 236 in exon 4; and 274, 275, 277, 279, 285, 298, or 309 in exon 5 of the red and green cone photopigments and to look for "poison" combinations of amino acids at these positions in the diagnosis of vision disorders. One might not have to examine all 18 dimorphic positions to make a diagnosis. For example, because the dimorphic positions in exon 5 are tightly linked, one typically only has to examine one of the codon positions within exon 5 to make an initial identification of the gene as encoding either a red or green cone photopigment. The dimorphic positions encoded in exons 2, 3, and 4 are preferably all examined. However, some disorders do not require that all positions be reviewed.

There are currently a variety of molecular biological methods available that allow examination of the DNA sequences of the red and green photopigment genes. For example, gene fragments may be amplified using the polymerase chain reaction (PCR). The red and green pigment genes can be separately and selectively amplified as described previously (J. Neitz, M. Neitz and Grishok, Vision Research 35: 2395-2407, 1995).

Amplified gene fragments may be subjected to one or more of the following procedures that provide information about the DNA sequence: 1) Direct DNA sequence of the PCR products as described previously (J. Neitz, M. Neitz and Grishok, supra, 1995); and/or 2) Restriction digestion analysis (described previously in J. Neitz, M. Neitz and Grishok, supra, 1995). Some of the amino acid substitutions indicated above are accompanied by a restriction site polymorphism. For example, the amino acid at position 180 is either a serine or an alanine. If alanine is encoded, the DNA fragment contains a BsoFl restriction site that is absent if serine is the amino acid encoded. Thus, PCR-amplified DNA fragments can be digested with appropriate restriction enzyme and the digestion products will be electrophoretically separated. The sizes of the fragments may be determined. Based on the sizes of the fragments observed, information about the DNA sequence and therefore about the amino acid sequence will be deduced. 3) Single strand conformation polymorphism or other similar procedures. The amplified DNA fragment is fluorescently or radioactively end labeled, denatured into single strands, and the strands are separated electrophoretically. Based on the mobility of the strands in the electric field, information about the DNA sequence can be deduced.

Once one has determined the amino acid specified at the above-described codon positions, one can then compare this amino acid data to the previously determined amino acid combinations suggestive of various color vision deficiencies. See U.S. Pat. No. 5,837,461. The "eyedox" brand geneotypic test kit and sequencing services provided by Genevolve Vision Diagnostics, Inc. (Albuquerque, N. Mex., USA), is another suitable manner of securing such information.

In some embodiments, identifying an individual having a visual insensitivity between a first visible color wavelength and a second visible color wavelength includes phenotypically determining an individual. In some embodiments, these phenotypic determinations can be achieved by exhibiting color photographs or plates and asking the subject to indicate what he or she sees depicted in the plate. In an embodiment, the method for correcting a visual insensitivity in a mammal comprises providing a standardized examination. In an embodiment, the method for correcting a visual insensitivity in a mammal comprises correlating the score of the examination with vision disorders. Those skilled in the art will recognize that these include isochromic test plates and their use, e.g., Ishihara 14/24/38 plate editions (Kanehara Trading, Tokyo JP, 2009), Hardy Rand and Ritter Pseudoisocromic Plate test, 4th Ed.; Dvorine 2d Ed, American Optical Company, 1965; and/or Richmond HRR pseudo isochromic plates, (1991 ed). Another suitable example includes the pencil and paper test described in A New Mass Screening Test for Color-Vision Deficiencies in Children, Neity, Maureen, et al, Color Research and Application, Supp. Vol. 26, S239-S249 (2000). Other instrumentation is available to make such vision deficiency determinations, e.g., Farnswarth 100 Hue Test, (Richmond Products, Inc., Albuquerque, N. Mex., USA), Heidelberg Multi-color (HMC) Anomaloscopes (Oculus, Inc., Lynwood, Wash., USA). The determination of the presence of vision deficiencies and/or the severity of such deficiencies can be attained by the above instrumentations or methods and or combinations thereof.

In some embodiments, the deficiencies are determined and described in differences in spectral separation between at least two photopigments. In some embodiments, the at least two photopigments are the L photopigment, the M photopigment, and or combinations, hybrids or variants of the L or M photopigments. In some embodiments, the spectral separation is described as the differences in the spectral excitation at least two photopigments are the L photopigment, the M photopigment, and or combinations, hybrids or variants of the L or M photopigments.

In an embodiment, the method comprises providing an optical element as described herein that corrects the visual insensitivity. In some embodiments, providing an optical element further comprises incorporating a sufficient amount of a fluorescent compound into the optical element to increase the visual sensitivity between a first visible color wavelength and a second visible color wavelength.

In some embodiments, providing an optical element further comprises incorporating a sufficient amount of a second fluorescent material into the optical element to increase the visual sensitivity between a first visible color wavelength and a second visible color wavelength.

One general synthetic procedure for synthesizing luminescent dyes in accordance with the general formula (I) is set forth below:

Scheme 1: general synthetic procedure for making compounds of general formula (I)

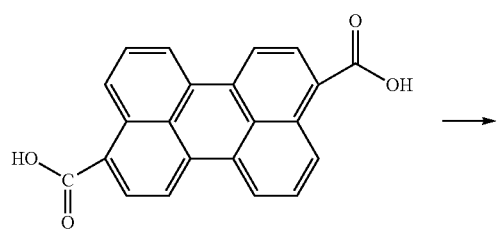

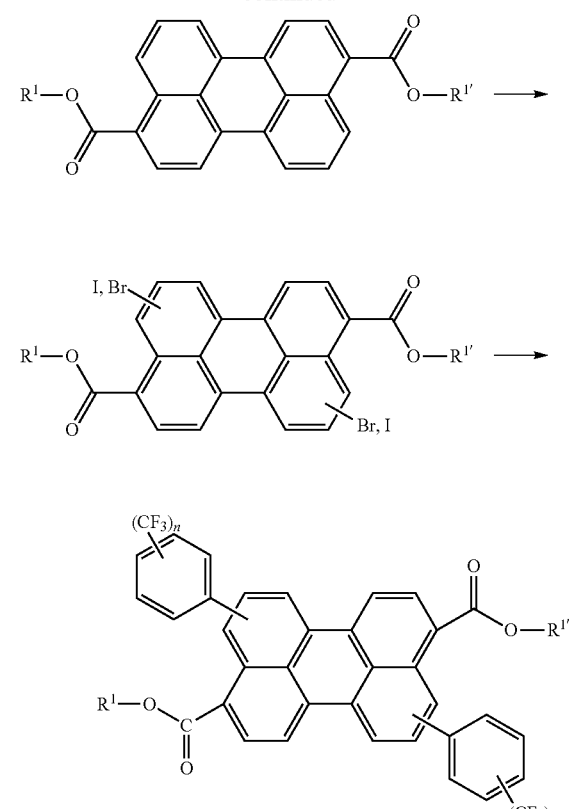

In the first step of Scheme 1, perylenedicarboxylic acid is converted into the corresponding diester by using typical esterification methods, known to those having ordinary skill in the art guided by the present disclosure. In the second step, perylenedicarboxylic acid di-ester is converted into either the dibromo or diiodo derivative by using a bromination/iodination reagent, under conditions known to those skilled in the art guided by the present disclosure. Some examples of these types of reagents include N-bromosuccinimide (NBS) and N-iodosuccinimide (NIS). The third step of Scheme 1 is to couple the corresponding perylenedicarboxylic acid di-ester iodo/bromo with a —$CF_3$ group containing boronic acid derivative in the presence of a catalyst. If more than one —$CF_3$ group is to be coupled to the perylene core, then additional bromine or iodine atoms are added during the second step, described above. Those having ordinary skill in the art will recognize that many catalysts can be used, but typical examples include palladium complex derivatives and copper derivatives.

The following is a listing of embodiments that are specifically contemplated herein.

Embodiment 1

An optical element for improving ability to distinguish color comprising: a luminescent compound dispersed in a matrix material, wherein the optical element is sufficiently transparent to allow a person to see through the optical element.

Embodiment 2

The optical element of embodiment 1, wherein the optical element is configured to correct a visual insensitivity between a first visible color wavelength and a second visible color wavelength;

wherein the matrix material is substantially transparent; and wherein the luminescent compound dispersed within the substantially transparent matrix material, wherein the luminescent compound has an emissive wavelength that substantially overlaps with the first visible color wavelength.

Embodiment 3

The optical element of embodiment 2, wherein the luminescent compound is present in an amount that provides a transmittance that is greater than 90% at the first visible wavelength.

Embodiment 4

The optical element of embodiment 2 or 3, wherein the luminescent compound is present in the substantially transparent matrix material in an amount in the range of about 1% to about 15%, by weight, based upon the weight of the composition.

Embodiment 5

The optical element of any of embodiments 2-4, further comprising a light absorbing dye, wherein the light absorbing dye has an absorption band that substantially overlaps with the second visible color wavelength.

Embodiment 6

The optical element of any of the preceding embodiments, wherein the luminescent compound comprises a perylene derivative dye.

Embodiment 7

The optical element according to embodiment 6, wherein the perylene derivative dye is represented by a formula:

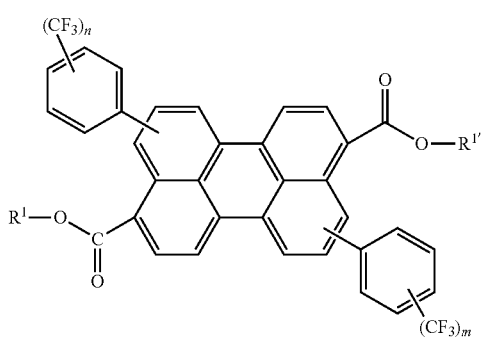

wherein $R^1$ and $R^{1'}$ are independently hydrogen, $C_1$-$C_{10}$ alkyl, $C_3$-$C_{10}$ cycloalkyl, $C_2$-$C_{10}$ alkoxyalkyl, $C_6$-$C_{18}$ aryl, or $C_6$-$C_{20}$ arylalkyl; m is 1, 2, 3, 4, or 5; and n is 1, 2, 3, 4, or 5.

Embodiment 8

The optical element according to embodiment 7, wherein the perylene derivative dye is:

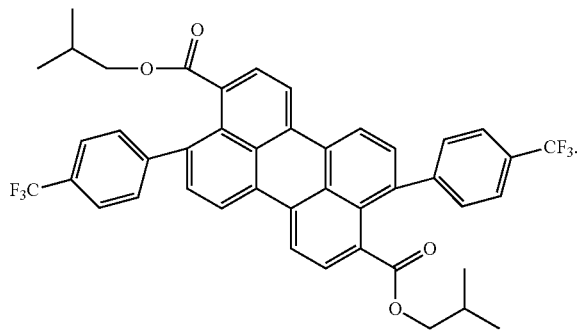 [SMILES: CC(C)COC(=O)c1ccc2c3ccc(-c4ccc(C(F)(F)F)cc4)c4c(C(=O)OCC(C)C)ccc(c5ccc(-c6ccc(C(F)(F)F)cc6)c1c25)c43]

Embodiment 9

The optical element of any of the preceding embodiments, further comprising a second luminescent compound, wherein the second luminescent compound increases the emission of the first visible color wavelength, increases the emission of the second visible color wavelength, further separates the peak emissive wavelength of the first color wavelength from the second color wavelength, or both increases and further separates the peak emissive wavelengths.

Embodiment 10

The optical element according to embodiment 9, wherein said second luminescent compound is N-phenyl-N-(4'-(1-phenyl-1H-benzo[d]imidazol-2-yl)-[1,1'-biphenyl]-4-yl) naphthalen-1-amine or 4,4'-bis[N-(naphthyl)-N-phenyl-amino]biphenyl.

Embodiment 11

A composition comprising a polymer and a rhodamine or a rhodamine derivative, wherein the polymer comprises polyvinyl alcohol or a derivative thereof comprising $C_{1-6}$ ester or $C_{1-6}$ acetal pendant groups.

Embodiment 12

The composition of embodiment 11, wherein the rhodamine is:

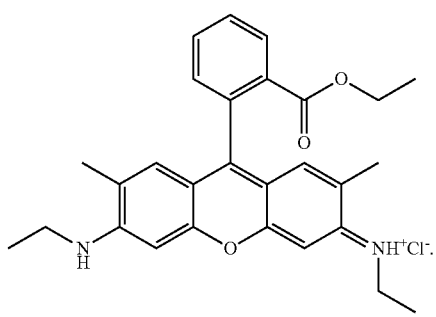

Embodiment 13

The composition of embodiment 11 or 12, wherein the polymer is a combination of repeat unit a, repeat unit b, and repeat unit c:

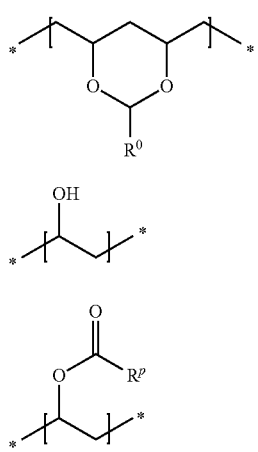

repeat unit a repeat unit b repeat unit c wherein $R^o$ and $R^p$ are independently H or $C_{1-5}$ alkyl.

Embodiment 14

The composition of embodiment 13, wherein $R^o$ is $CH_2CH_2CH_3$.

Embodiment 15

The composition of embodiment 13 or 14, wherein $R^p$ is $CH_3$.

Embodiment 16

The composition of any of embodiments 13-15, wherein repeat unit a is about 80% of the weight of the polymer, repeat unit b is about 17% to about 20% of the weight of the polymer, and repeat unit c is about 0.01% to about 3% of the weight of the polymer.

Embodiment 17

The composition of any of embodiments 11-16, wherein the rhodamine or the rhodamine derivative is about 2% (w/w) to about 10% (w/w) of the composition.

Embodiment 18

The composition of embodiment 17, comprising:
rhodamine 6G in an amount of about 4% (w/w) to about 6% (w/w); and
poly(vinyl butyral-co-vinyl alcohol-co-vinyl acetate) having an average molecular weight in a range of about 170,0000 g/mol to about 250,000 g/mol, and in an amount of about 90% (w/w) to about 96% (w/w).

Embodiment 19

An optical element comprising a composition according to any of embodiments 11-18, wherein the composition is solid.

Embodiment 20

An optical element of any of embodiments 1-10, wherein the luminescent compound is:

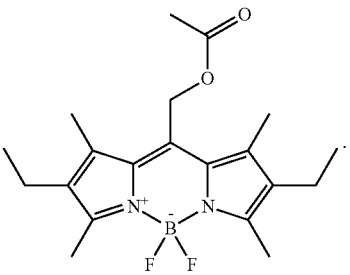

Embodiment 21

The optical element of any of embodiments 1-10 and 19-20, wherein the luminescent compound absorbs light at an absorption wavelength and emits light at an emission wavelength, wherein a human cone photopigment is substantially more sensitive to the emission wavelength than to the absorption wavelength; and wherein the optical element is configured so that a person can better distinguish the colors by viewing an image or an object comprising the colors through the optical element.

Embodiment 22

The optical element of any of embodiments 1-10 and 19-21, wherein the optical element is configured to absorb and emit visible light so that when an object or an image is viewed through the optical element, a first color having a first set of color coordinates is converted to a second color having a second set of color coordinates to aid in distinguishing colors; and the distance between the first set of color coordinates and the second set of color coordinates is at least about 0.02 color coordinate units.

Embodiment 23

A method for preparing an optical element comprising:
selecting a luminescent compound for use in the optical element;
wherein the optical element is configured to convert a color having a first set of color coordinates to a color having a second set of color coordinates by absorption and emission of visible light;
wherein the luminescent compound is selected so that the distance between the first set of color coordinates and the second set of color coordinates is at least about 0.02 color coordinate units.

Embodiment 24

The optical element of embodiment 22 or method of embodiment 23, wherein the distance between the first set of color coordinates and the second set of color coordinates is at least about 0.04 color coordinate units.

Embodiment 25

The optical element of embodiment 22 or method of embodiment 23, wherein the distance between the first set of color coordinates and the second set of color coordinates in the direction normal to a color confusion line nearest to the first set of color coordinates is at least about 0.02 color coordinate units.

Embodiment 26

The optical element or method of embodiment 25, wherein the distance between the first set of color coordinates and the second set of color coordinates in the direction normal to a color confusion line nearest to the first set of color coordinates is at least about 0.04 color coordinate units.

Embodiment 27

The optical element or method of embodiment 25 or 26, wherein the color confusion line is a deuteronopia color confusion line.

Embodiment 28

The optical element or method of embodiment 27, wherein the color confusion line is deuteronopia color confusion line 7.

Embodiment 29

The optical element or method of embodiment 27, wherein the color confusion line is deuteronopia color confusion line 8.

Embodiment 30

The optical element or method of embodiment 27, wherein the color confusion line is deuteronopia color confusion line 9.

Embodiment 31

The optical element or method of any of embodiments 22-30, wherein the first set of color coordinates is about (0.375-0.380, 0.485-0.490), about (0.475-0.480, 0.410-0.415), about (0.368-0.373, 0.485-0.490), or about (0.370-0.375, 0.460-0.465).

Embodiment 32

The optical element or method of any of embodiments 22-30, wherein the first set of color coordinates is about (0.330-0.335, 0.340-0.345).

Embodiment 33

The optical element or method of any of embodiments 22-30, wherein the first set of color coordinates is about (0.570-0.575, 0.340-0.345), about (0.475-0.480, 0.468-0.473), or about (0.565-0.570, 0.395-0.400).

Embodiment 34

The optical element or method of any of embodiments 22-30, wherein the first set of color coordinates is about (0.510-0.515, 0.340-0.344), or about (0.480-0.485, 0.388-0.392).

Embodiment 35

The optical element or method of any of embodiments 22-30, wherein the first set of color coordinates is about (0.290-0.295, 0.495-0.500).

Embodiment 36

A device for improving the ability to distinguish colors prepared by a method according to any of embodiments 23-35.

Embodiment 37

The optical element of any of embodiments 1-10, 19-22, and 24-35, wherein the optical element absorbs light in a wavelength range near peak sensitivity for an M human cone photopigment and emits light of a longer wavelength in a wavelength range near peak sensitivity for an L human cone photopigment.

Embodiment 38

The optical element of any of embodiments 1-10, 19-22, 24-35, and 37, wherein the optical element is a coating.

Embodiment 39

The optical element of embodiment 38, wherein the coating is scratch resistant.

Embodiment 40

The optical element of embodiment 38 or 39, wherein the coating comprises a polycarbonate, a hard acrylate, a polyurethane, or a polyurea urethane.

Embodiment 41

The optical element of any of embodiments 1-10, 19-22, 24-35, and 37-40, wherein the optical element is configured to modify a color of an object or image viewed through the optical element by a user, wherein modifying the color allows the user to better distinguish colors.

Embodiment 42

A device comprising:
an electronic display; and
the optical element of any of embodiments 1-10, 19-22, 24-35, and 37-41;
wherein the device is configured so that at least a portion of the light emitted from the display passes through the optical element, and the optical element modifies a color of the light emitted from the display that passes through the optical element.

Embodiment 43

The electronic device of embodiment 1, further comprising a touch screen component coupled to the optical element and the electronic display; wherein the touch screen component comprises:
a first conductive layer, a second conductive layer, and a spacer between the first conductive layer and the second conductive layer, wherein the first conductive layer and the second conductive layer are substantially transparent;

wherein the device is configured so that contact by a user to the touch screen can cause the first conductive layer to contact the second conductive layer to thereby allow current to flow between the first conductive layer and the second conductive layer; and wherein the device is configured so that at least a portion of the light emitted from the display passes through the touch screen component and passes through the optical element.

Embodiment 44

The device of embodiment 43, wherein the touch screen component further comprises a first support layer, wherein the first conductive layer is disposed between the spacer and the first support layer.

Embodiment 45

The device of embodiment 43 or 44, wherein the touch screen component further comprises a second support layer, wherein the second conductive layer is disposed between the spacer and the second support layer.

Embodiment 46

The device of embodiment 44 or 45, wherein the touch screen component further comprises a first dielectric layer, wherein the first dielectric layer is disposed between the first conductive layer and the first support layer.

Embodiment 47

The device of embodiment 45 or 46, wherein the touch screen component further comprises a second dielectric layer, wherein the second dielectric layer is disposed between the second conductive layer and the second support layer.

Embodiment 48

A device comprising the optical element of any of embodiments 1-10, 19-22, 24-35, and 37-41, wherein the device is an ocular lens.

Embodiment 49

The device of embodiment 48, wherein the ocular lens is an intraocular lens.

Embodiment 50

The device of embodiment 48, wherein the ocular lens is a hard contact lens.

Embodiment 51

The device of embodiment 48, wherein the ocular lens is a soft contact lens.

Embodiment 52

The device of any of embodiments 48-51, wherein the optical element comprises a hydrogel polymer.

Embodiment 53

The device of embodiment 52, wherein the hydrogel polymer incorporates a hydrophilic acrylate monomer.

Embodiment 54

The device of embodiment 53, wherein the hydrogel polymer further incorporates an alkyl acrylate monomer or an alkyl methacrylate monomer.

Embodiment 55

A device comprising the optical element of any of embodiments 1-10, 19-22, 24-35, and 37-41, wherein the device is an item of eyewear.

Embodiment 56

The device of embodiment 55, wherein the eyewear is eyeglasses or sunglasses.

Embodiment 57

A device comprising the optical element of any of embodiments 1-10, 19-22, 24-35, and 37-41, wherein the device is a window.

Embodiment 58

A device comprising the optical element of any of embodiments 1-10, 19-22, 24-35, and 37-41, wherein the luminescent compound has an absorption band range and the optical element further comprises a light emitting element, wherein the light emitting element is in optical communication with the luminescent compound to provide an excitation source for the luminescent compound.

Embodiment 59

The device of embodiment 58, wherein the light emitting element comprises a light emitting thin film having a maximum emission peak within the absorption band range of the luminescent compound.

Embodiment 60

The device of embodiment 58 or 59, further comprising an optical waveguide in optical communication with the luminescent element and the light emitting element.

Embodiment 61

The device of any of embodiments 36 and 42-60, wherein the optical element has a transparency that is greater than or equal to 70%.

Embodiment 62

The device of any of embodiments 36 and 42-61, wherein the matrix material comprises glass, a thiourethane, a polycarbonate (such as CR-39), a polyacrylate, one or more terpolymers of hexafluoroacetone-tetrafluoroethylene-ethylene (HFA/TFE/E terpolymers), polymethyl methacrylate (PMMA), hydrogel, organosiloxane, or a combination.

Embodiment 63

The device of any of embodiments 36 and 42-62, wherein the optical element absorbs light at a wavelength that is less than maximally detected by a normal human cone middle-wavelength sensitive (M) photopigment and emits light at a wavelength that is detected to a substantially greater extent by the normal human cone M photopigment.

Embodiment 64

The device of any of embodiments 36 and 42-63, wherein the optical element absorbs light at a wavelength that is less than maximally detected by a variant human cone middle-wavelength sensitive (MV) photopigment and emits light at a wavelength that is detected to a substantially greater extent by the same human cone MV photopigment.

Embodiment 65

The device of any of embodiments 36 and 42-64, wherein the optical element absorbs light at a wavelength that is less than maximally detected by a normal human cone long-wavelength sensitive (L) photopigment and emits light at a wavelength that is detected to a substantially greater extent by the normal human cone L photopigment.

Embodiment 66

The device of any of embodiments 36 and 42-65, wherein the optical element absorbs light at a wavelength that is less than maximally detected by a variant human cone long-wavelength sensitive (LV) photopigment and emits light at a wavelength that is detected to a substantially greater extent by the same human cone LV photopigment.

Embodiment 67

The device of any of embodiments 36 and 42-66, wherein the optical element has a peak wavelength of visible absorption of about 520 nm to about 540 nm and a peak wavelength of visible emission of about 550 nm to about 570 nm.

Embodiment 68

The device of any of embodiments 36 and 42-66, wherein the optical element has a peak wavelength of visible absorption of about 540 nm to about 550 nm.

Embodiment 69

The device of any of embodiments 36 and 42-66, wherein the optical element has a peak wavelength of visible absorption of about 450 nm to about 600 nm and a peak wavelength of visible emission of about 560 to about 720 nm.

Embodiment 70

The device of any of embodiments 36 and 42-66, wherein the optical element has a median wavelength of visible absorption of about 380 nm to about 450 nm.

Embodiment 71

The device of any of embodiments 36 and 42-66, wherein the optical element has a median wavelength of visible absorption of about 420 nm to about 480 nm.

Embodiment 72

The device of any of embodiments 36 and 42-66, wherein the optical element has a median wavelength of visible emission of about 500 nm to about 600 nm.

Embodiment 73

The device of any of embodiments 36 and 42-66, wherein the optical element has an average wavelength of visible absorption of about 380 nm to about 450 nm.

Embodiment 74

The device of any of embodiments 36 and 42-66, wherein the optical element has an average wavelength of visible absorption of about 420 nm to about 480 nm.

Embodiment 75

The device of any of embodiments 36 and 42-66, wherein the optical element has an average wavelength of visible emission of about 500 nm to about 600 nm.

Embodiment 76

The device of any of embodiments 36 and 42-66, wherein the optical element has a peak wavelength of visible absorption of about 380 nm to about 450 nm.

Embodiment 77

The device of any of embodiments 36 and 42-66, wherein the optical element has a peak wavelength of visible absorption of about 420 nm to about 480 nm.

Embodiment 78

The device of any of embodiments 36 and 42-66, wherein the optical element has a peak wavelength of visible emission of about 500 nm to about 600 nm.

Embodiment 79

The device of any of embodiments 36 and 42-66, wherein the optical element has a median wavelength of visible absorption of about 510 nm to about 550 nm.

Embodiment 80

The device of embodiment 79, wherein the optical element has a median wavelength of visible emission of about 540 nm to about 580 nm.

Embodiment 81

The device of any of embodiments 36 and 42-66, wherein the optical element has an average wavelength of visible absorption of about 510 nm to about 550 nm.

Embodiment 82

The device of embodiment 81, wherein the optical element has an average wavelength of visible emission of about 540 nm to about 580 nm.

Embodiment 83

The device of any of embodiments 36 and 42-66, wherein the optical element has a peak wavelength of visible absorption of about 510 nm to about 550 nm.

Embodiment 84

The device of embodiment 83, wherein the optical element has a peak wavelength of visible emission of about 540 nm to about 580 nm.

Embodiment 85

The device of embodiment 84, wherein the optical element has a peak wavelength of visible absorption of about 530 nm to about 550 nm and a peak wavelength of visible emission of about 560 nm to about 580 nm.

Embodiment 86

The device of any of embodiments 36 and 42-66, wherein the optical element has a peak wavelength of visible absorption of about 545 nm to about 550 nm.

Embodiment 87

The device of any of embodiments 36, 42-66, and 86, wherein the optical element has a peak wavelength of visible emission of about 560 nm to about 580 nm.

Embodiment 88

The device of embodiment 87, wherein the optical element has a peak wavelength of visible emission of about 565 nm to about 575 nm.

Embodiment 89

The device of any of embodiments 36 and 42-88, wherein the optical element has a Stokes shift in the range of about 51 nm to about 120 nm when dispersed in the matrix material.

Embodiment 90

The device of any of embodiments 36 and 42-89 wherein the optical element has an absorption band with a full width half maximum value of less than or equal to 85 nm when dispersed in the matrix material.

Embodiment 91

A method of improving ability to distinguish colors comprising positioning an optical element of any of embodiments 1-10, 19-22, 24-35, and 37-41 or a device of any of embodiments 36 and 42-90 so that an image or an object may be viewed by an individual through the optical element.

Embodiment 92

The method of embodiment 91, wherein the individual has normal color vision.

Embodiment 93

The method of embodiment 91, wherein the individual has an impaired ability to distinguish colors.

Embodiment 94

A method for correcting visual insensitivity, comprising:
providing or arranging to provide an optical element of any of embodiments 1-10, 19-22, 24-35, and 37-41 or a device of any of embodiments 36 and 42-90 to an individual that has been identified as having a visual insensitivity between a first visible color wavelength and a second visible color wavelength;
wherein the optical element has been selected to correct the visual insensitivity between the first visible color wavelength and the second visible color wavelength.

Embodiment 95

A method for correcting visual insensitivity, comprising:
selecting an optical element of any of embodiments 1-10, 19-22, 24-35, and 37-41 or a device of any of embodiments 36 and 42-90 to correct a visual insensitivity in a individual who has been identified as having the visual insensitivity;
wherein the visual insensitivity comprises insensitivity in distinguishing between a first visible color wavelength and a second visible color wavelength; and

Embodiment 96

The method according to embodiment 95, further comprising providing or arranging to provide the optical element or device to the individual.

Embodiment 97

The method according to any of embodiments 91-96, wherein the individual has deuteranomaly.

Embodiment 98

The method according to any of embodiments 94-97, wherein the individual has been as having the visual insensitivity by:
examining an amino acid sequence of the individual's red or green photopigments;
correlating the amino acid sequence with amino acid combinations associated with vision disorder, wherein the amino acid sequence is the sequence at positions selected from the group consisting of codon positions 65, 111, 116, 153, 171, 174, 178, 180, 230, 233, 236, 274, 275, 277, 279, 285, 298, and 309 of the gene encoding the red or green photopigment and wherein the correlation comprises comparison of the amino acid sequence with amino acid sequences shown to be diagnostic of vision disorders.

Embodiment 99

The method according to any of embodiments 94-98, wherein the individual has been as having the visual insensitivity by:
providing a standardized examination; and
correlating the score of the examination with vision disorders.

EXAMPLES

It has been discovered that embodiments of optical elements described herein improve the ability of colorblind individuals to distinguish a first color from a second color having a different wavelength. These benefits are further shown by the following examples, which are intended to be illustrative of the embodiments of the disclosure, but are not intended to limit the scope or underlying principles in any way.

Example 1

Luminescent Dye

The luminescent dye, diisobutyl 4,10-bis(4-(trifluoromethyl)phenyl)perylene-3,9-dicarboxylate (Green-1), was synthesized in the following process:

a) Step-1—Synthesis of intermediate, diisobutyl 4,10-dibromoperylene-3,9-dicarboxylate

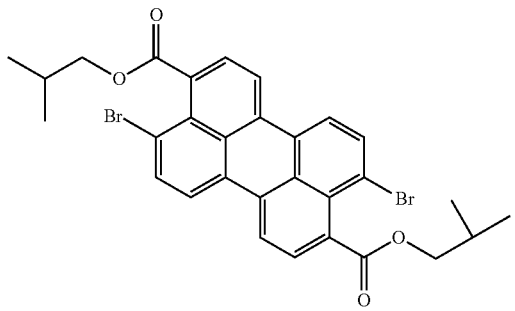 [SMILES: CC(C)COC(=O)c1ccc2c3ccc(Br)c4c(C(=O)OCC(C)C)ccc(c5ccc(Br)c1c52)c43]

To synthesize diisobutyl 4,10-dibromoperylene-3,9-dicarboxylate, N-bromosuccinimide (7.85 g, 44 mol) was added to a solution of perylenedicarboxylic acid diisobutyl ester, which can be purchased from Aldrich Chemical Co. Perylenedicarboxylic diisobutyl ester was also synthesized from the corresponding di-acid derivative by esterification with isobutyl alcohol in DMF (50 mL) under heat at 65° C. for 3 hours (until the initial suspension changes to a clear solution). After cooling, methanol (500 mL) was added to the stirred reaction mixture. Soon heavy precipitate was formed, which was separated by filtration, washed with small portion of cold methanol, and dried in a vacuum oven to give diisobutyl 4,10-dibromoperylene-3,9-dicarboxylate as a yellow solid, pure by $^1$H NMR (9.6 g, 78%).

b) Step-2—Synthesis of diisobutyl 4,10-bis(4-(trifluoromethyl)phenyl)perylene-3,9-dicarboxylate (Green-1)

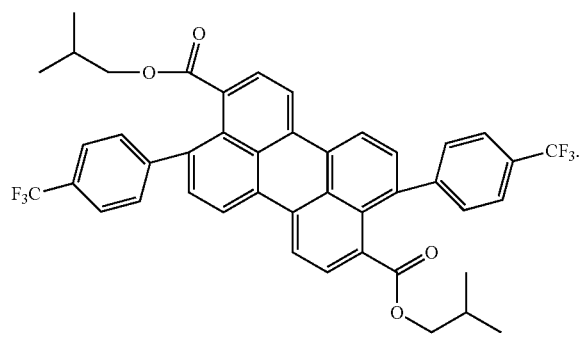 [SMILES: CC(C)COC(=O)c1ccc2c3ccc(-c4ccc(C(F)(F)F)cc4)c4c(C(=O)OCC(C)C)ccc(c5ccc(-c6ccc(C(F)(F)F)cc6)c1c25)c43]

To synthesize diisobutyl 4,10-bis(4-(trifluoromethyl)phenyl)perylene-3,9-dicarboxylate, tetrakis(triphenylphosphine)palladium(0) (500 mg, 0.43 mmol) was added to a solution of diisobutyl 4,10-dibromoperylene-3,9-dicarboxylate (3.05 g, 5 mmol), 4-trifluoromethylphenylboronic acid (2.09 g, 11.0 mmol) in a mixture of toluene (50 mL), an aqueous solution of 2M $Na_2CO_3$ (20 mL), and ethanol (30 mL) under argon atmosphere. The reaction mixture was heated at 90° C. for 1 hour (until clear separation of organic layer, water, and solid was observed). The organic layer was separated and filtered through CELITE® (Celite Corp., CA) to remove the palladium catalyst, then the solvent was partially removed under vacuum. The product was precipitated from methanol, filtrated off, washed with cold methanol, and dried in a vacuum oven to give pure diisobutyl 4,10-bis(4-(trifluoromethyl)phenyl)perylene-3,9-dicarboxylate (by $^1$H NMR) as a yellow solid (3.30 g, 89%). Alternative purification was performed by column chromatography (silica gel and a mixture of hexane-ethyl acetate 4:1 as mobile phase).

Example 2

Polymerizable Dye a) 8-Hydroxymethyl-2,6-diethyl-1,3,5,7-tetramethyl pyrromethene fluoroborate (PMOH)

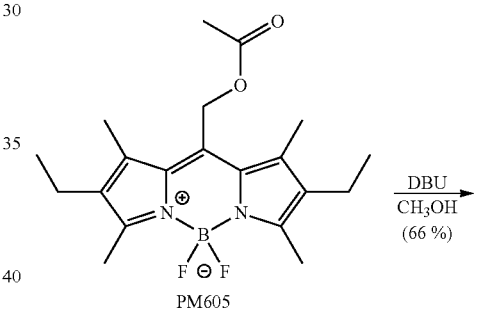

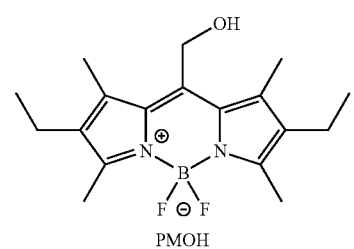

Compound PMOH (Amat-Guerri, F.; Liras, M.; Carrascoso, M. L.; Sastre, R., Photochem. Photobiol. 2003, 77, 577-584) was prepared as follows: to a stirring solution of 8-Acetoxymethyl-2,6-diethyl-1,3,5,7-tetramethyl pyrromethene fluoroborate (PM605) (1.19 g, 3.17 mmol) in anhydrous $CH_3OH$ (500 mL) was added 1,8-diazabicyclo [5.4.0]undec-7-ene (3.32 mL, 22.2 mmol) dropwise via syringe. Stirring was continued at RT until TLC ($SiO_2$, 4:1 hexanes-acetone) indicated consumption of the starting material (20 min), after which the reaction was concentrated in vacuo. Purification of the crude product by flash chromatography ($SiO_2$, 100% dichloromethane) provided PMOH (0.70 g, 66%) as a bright red solid.

b) 8-Methacryloxymethyl-2,6-diethyl-1,3,5,7-tetramethyl pyrromethene fluoroborate (P1MA)

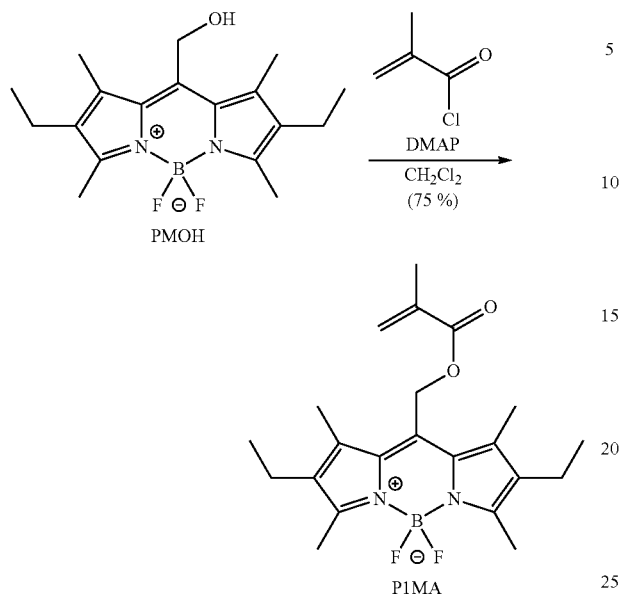

Following a procedure reported in the literature (Amat-Guerri, F.; Liras, M.; Carrascoso, M. L.; Sastre, R., Photochem. Photobiol. 2003, 77, 577-584), PMOH (0.10 g, 0.30 mmol), 4-(dimethylamino)pyridine (37 mg, 0.30 mmol), methacryloyl chloride (31 mg, 0.30 mmol) and dichloromethane (30 mL) afforded PIMA (90 mg, 75%) as metallic green, crystalline solid after flash chromatography (SiO$_2$, 9:1-hexanes:ethyl acetate).

Example 3

Polymerizable Dye

The polymerizable BODIPY dye (P1 MA) as synthesized in Example 2. (0.014 g) was added to a mixture of 0.849 g UniDic 17-806 [solids content 80%, Dainippon Ink and Chemicals, Tokyo, Japan], 0.02 g photopolymerization initiator (IRGACURE 907, Ciba Specialty Chemicals K. K.), 0.00068 g coating additive-gamma-methacrgamma-methacryloxypropyltrimethoxysilane (PC4100, Power Chemica), 0.452 g cyclopentanone, and 0.678 g of methoxy-2-propanol. The mixture was sonicated for about 30 minutes until a uniform solution was obtained. The solution was then spin-coated onto a glass slide at 2000 rpm held for about 10 seconds. The coated glass slide was then placed on a hot plate at about 100° C. for about 10 minutes to evaporate the solvents. Then the coating was irradiated with a 450 W UV lamp for about 45 seconds to cure the film.

Example 4

Optical Element, UV Absorbing Dye

An optical element was prepared as follows. To a mixture of poly(vinyl acetate-co-vinyl alcohol-co-vinyl butyral) (0.1 g) in n-butanol (1.52 g) and 1-methylpyrrolidinone (0.38 g), was added rhodamine B (0.01 g) and pyrromethene 567 [Exciton Inc., Dayton, Ohio] (0.008 g). The resulting mixture was sonicated for about 45 minutes to obtain a homogeneous solution, solution 1. To a separate vial containing a mixture of poly(vinyl acetate-co-vinyl alcohol-co-vinyl butyral) (0.1 g) in n-butanol (1.52 g) and 1-methylpyrrolidinone (0.38 g), was added pyrromethene 597 [Exciton Inc] (0.008 g) and 663-50, N-phenyl-N-(4'-(1-phenyl-1H-benzo[d]imidazol-2-yl)-[1,1'-biphenyl]-4-yl)naphthalen-1-amine (008 g).

a) N-phenyl-N-(4'-(1-phenyl-1H-benzo[d]imidazol-2-yl)-[1,1'-biphenyl]-4-yl)naphthalen-1-amine (663-50)

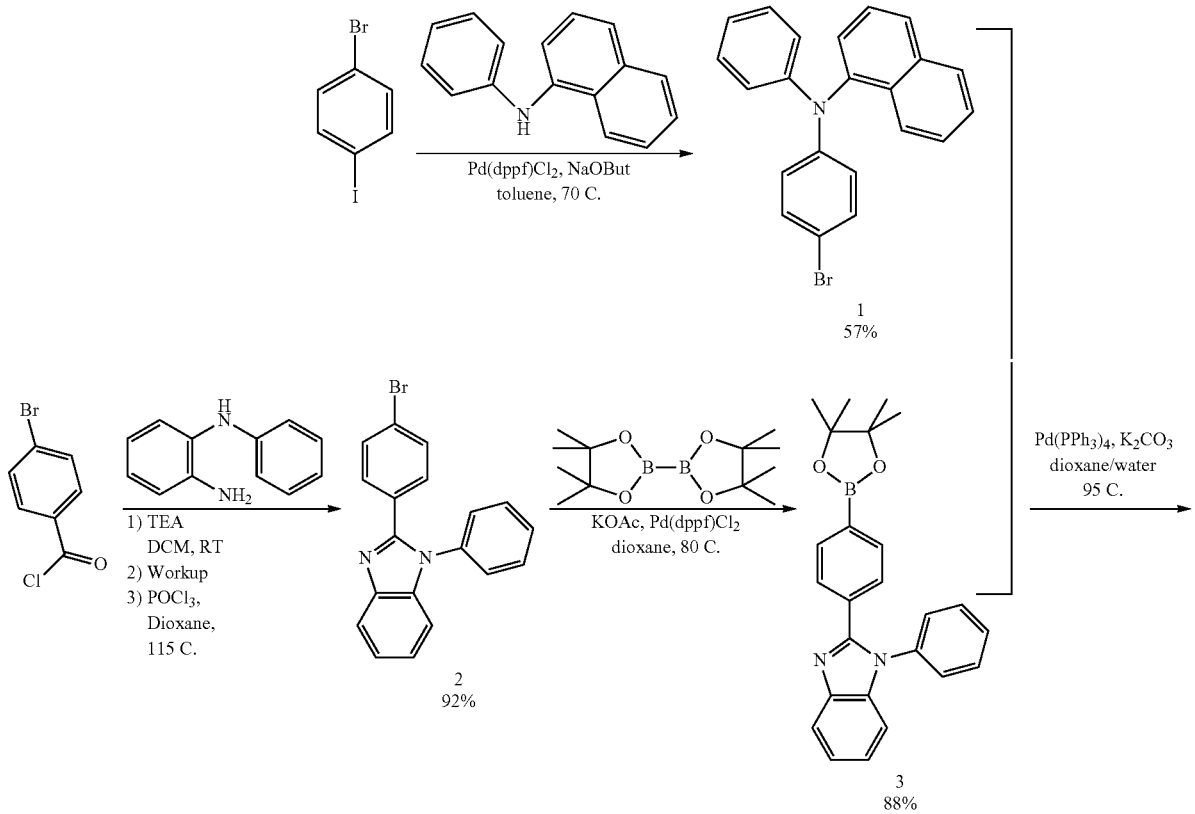

-continued

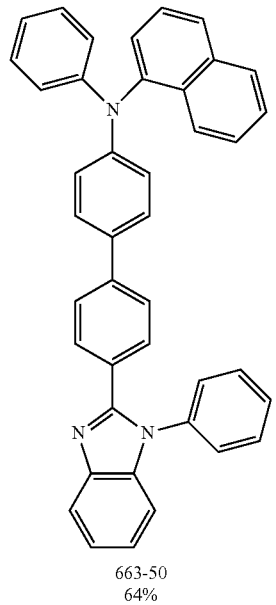

663-50
64%

The process for synthesizing N-phenyl-N-(4'-(1-phenyl-1H-benzo[d]imidazol-2-yl)-[1,1'-biphenyl]-4-yl)naphthalen-1-amine (663-50) was derived from Korean patent, number 1020070141920 for Chiel Industries. Compound 663-50 was synthesized in the following manner. N-phenylnaphthalen-1-amine (3.0 g, 13.68 mmol), 1-bromo-4-iodobenzene (9.68 g, 34.20 mmol), sodium tert-butoxide (3.29 g, 34.20 mmol), and Pd(dppf)Cl$_2$ (0.60 g, 0.82 mmol) were dissolved in 80 mL of anhydrous toluene. The reaction mixture was degassed with argon for 1 hour and then heated to 80° C. under argon for 40 hours. The reaction mixture was filtered and the solid was washed with ethyl acetate. An extraction was performed in ethyl acetate and the organic layer was washed with water and brine. The extract was dried over sodium sulfate, filtered, and concentrated. The resulting residue was purified by a silica gel column with 1:9 dichloromethane:hexanes as the eluent and the polarity was increased to 1:4 dichloromethane:hexanes. The material was then concentrated to yield compound 1 as a light yellow solid (57.2%).

Compound 2 was synthesized in the following manner. N1-phenylbenzene-1,2-diamine (8.56 g, 46.48 mmol) was dissolved in 230 mL of anhydrous dichloromethane and the resulting mixture was stirred in an ice bath. To the mixture added 4-bromobenzoyl chloride (10.00 g, 45.57 mmol) followed by slowly adding triethylamine (12.7 mL, 95.65 mmol) dropwise. The reaction mixture was removed from the ice bath upon the addition of the triethylamine. The reaction mixture was stirred at room temperature overnight under argon. The reaction mixture was extracted with dichloromethane and the organic layer was washed with sodium bicarbonate, water, and brine. The extract was dried over magnesium sulfate, filtered, and concentrated. To this crude mixture added 201 mL of anhydrous 1,4-dioxane and the mixture was then heated to 75° C. in order to dissolve material. After dissolving the solid, the reaction was allowed to cool and then phosphorus oxychloride (12.8 mL, 137.35 mmol) was added dropwise via a syringe. The reaction mixture was heated to 115° C. for 2 hours under argon. The reaction was cooled to room temperature and was quenched by adding 200 mL of sodium bicarbonate. After quenching the reaction, the reaction mixture was poured into 1 L of stirring cold sodium bicarbonate and allowed to stir overnight. The mixture was extracted with dichloromethane and the organic layer was washed with sodium bicarbonate, water, and brine. The extract was dried over magnesium sulfate, filtered, and concentrated. The resulting residue was purified by two precipitations in dichloromethane/hexanes to yield compound 3 as brown color solid (96%).

Compound 3 was synthesized in the following manner. Compound 2 (14.61 g, 41.82 mmol), bis(pinacolato)diboron (11.68 g, 46.00 mmol), Pd(dppf)Cl$_2$ (1.53 g, 2.09 mmol), and (12.3 g, 125.47 mmol) were dissolved in 200 mL of anhydrous 1,4-dioxane. The reaction mixture was degassed with argon for 1.5 hours and then heated to 80° C. under argon overnight. The reaction mixture was filtered and an extraction was performed in ethyl acetate and the organic layer was washed with sodium bicarbonate, water, and brine. The extract was dried over magnesium sulfate, filtered, and concentrated. The resulting residue was purified by a silica gel column with 1:4 ethyl acetate:hexanes (utilizing ~6 L of this solvent) as the eluent and then a gradient from 25% ethyl acetate to 40% ethyl acetate was slowly increased by 5% utilizing 2 L of each new increasing polarity. The material was then concentrated to yield compound 4 as a peach color solid (86.0%).

663-50 was synthesized in the following manner. Compound 3 (2.19 g, 5.52 mmol), compound 1 (2.15 g, 5.74 mmol), Pd(PPh$_3$)$_4$ (0.32 g, 0.28 mmol), and potassium carbonate (2.29 g, 16.56 mmol) were dissolved in a 1:5 ratio of water (10 mL) and 1,4-dioxane (50 mL). The reaction mixture was degassed with argon for 45 minutes and then heated to 95° C. under argon overnight. The reaction mixture was extracted with dichloromethane and the organic layer was washed with sodium bicarbonate, water, and brine. The extract was dried over sodium sulfate, filtered and concentrated. The resulting residue was purified by a silica gel column with dichloromethane as the eluent. The material was then concentrated and crystallized from dichloromethane:hexanes to yield 663-50 (64%).

The mixture of poly(vinyl acetate-co-vinyl alcohol-co-vinyl butyral) in n-butanol and 1-methylpyrrolidinone, pyrromethene 597 [Exciton Inc], and 663-50 was then sonicated for about 45 minutes to obtain a homogeneous solution, solution 2.

b) UV Absorbing Dye

A glass slide was spin coated at 2000 RPM for about 10 seconds with solution 1 on one side, and then heated to about 110° C. on a hot plate to evaporate the solvents, resulting in a coated glass slide. Then, the same glass slide was turned over and the opposite, uncoated side was then coated with solution 2 by spin coating at 2000 RPM for about 10 seconds. After heating to about 110° C. on a hot plate, a glass slide which was coated on both sides with different solutions was obtained. This optical element has a transmittance spectrum shown in FIG. 14. Similar to FIG. 14, some optical elements may have a transmissive plateau from about 630 nm to about 800 nm, Such a transmissive plateau may have a transmittance of greater than about 90%, about 95%, or about 99%.

Example 5

Optical Element, Blue Absorbing Dye

Figure 15:
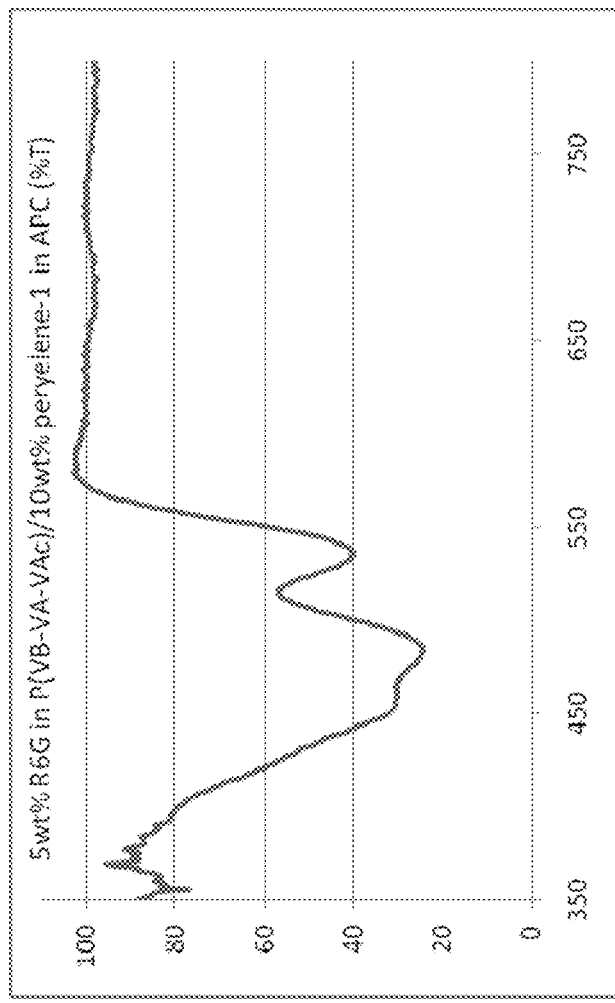
FIG. 15 shows the light transmittance spectra for an embodiment of a polymerizable dye described herein.

A solution of poly(vinyl acetate-co-vinyl alcohol-co-vinyl butyral) (0.1 g) and Rhodamine 6G (0.005 g) in n-butanol (1.9 g) was prepared by sonicating for about 45 minutes. The homogeneous solution was spin-coated onto a glass slide at 2000 RPM for about 10 seconds. The coating was dried by placing the slide on a hot plate at about 110° C. for about 20 minutes. After the film was dried, a solution of amorphous polycarbonate (200 mg), diisobutyl 4,10-bis(4-(trifluoromethyl)phenyl)perylene-3,9-dicarboxylate (20 mg), and toluene (1.8 g), which had been made homogeneous by sonication for about 1-hour, was spin-coated directly on top of the previous layer of rhodamine 6G in PVB. Then, the glass slide was placed on a hot plate again at about 110° C. for about 30 minutes to dry the coating. The resulting two-layered element had a transmittance spectrum shown in FIG. 15. Similar to FIG. 15, some optical elements may have a transmissive plateau from about 550 nm to about 750 nm. Such a transmissive plateau may have a transmittance of greater than: about 90%, about 95%, or about 99%.

Example 6

Optical Element (Device A)

The luminescent dye, diisobutyl 4,10-bis(4-(trifluoromethyl)phenyl)perylene-3,9-dicarboxylate, made in accordance with Example 1, was used without addition extraction or purification, and was intermixed with amorphous polycarbonate (APC) (Acros Organics, Geel, Belgium [Fisher Scientific USA, Pittsburgh, Pa., USA]) in an amount resulting in a luminescent dye:amorphous polycarbonate weight ratio of about 10:90. The mixture was then dissolved in a toluene solvent resulting in a composition that is 90%, by weight, of solvent with the use of sonication. The resulting solution was then spin-coated at about 2000 rpm, for about 5 seconds onto a clean glass slide (Corning plain Micro Slides, #2947) that was pre-cut to a 5 cm by 5 cm area. The resulting film was heated to about 120° C. for about 20 to about 30 minutes under air to evaporate the solvent. Film thicknesses can range from about 1 to about 3 micrometers when using these spin-coating conditions and solution compositions. The weight percentage of the luminescent compound was about 10%, by weight, based upon the weight of the composition.

Figure 6:
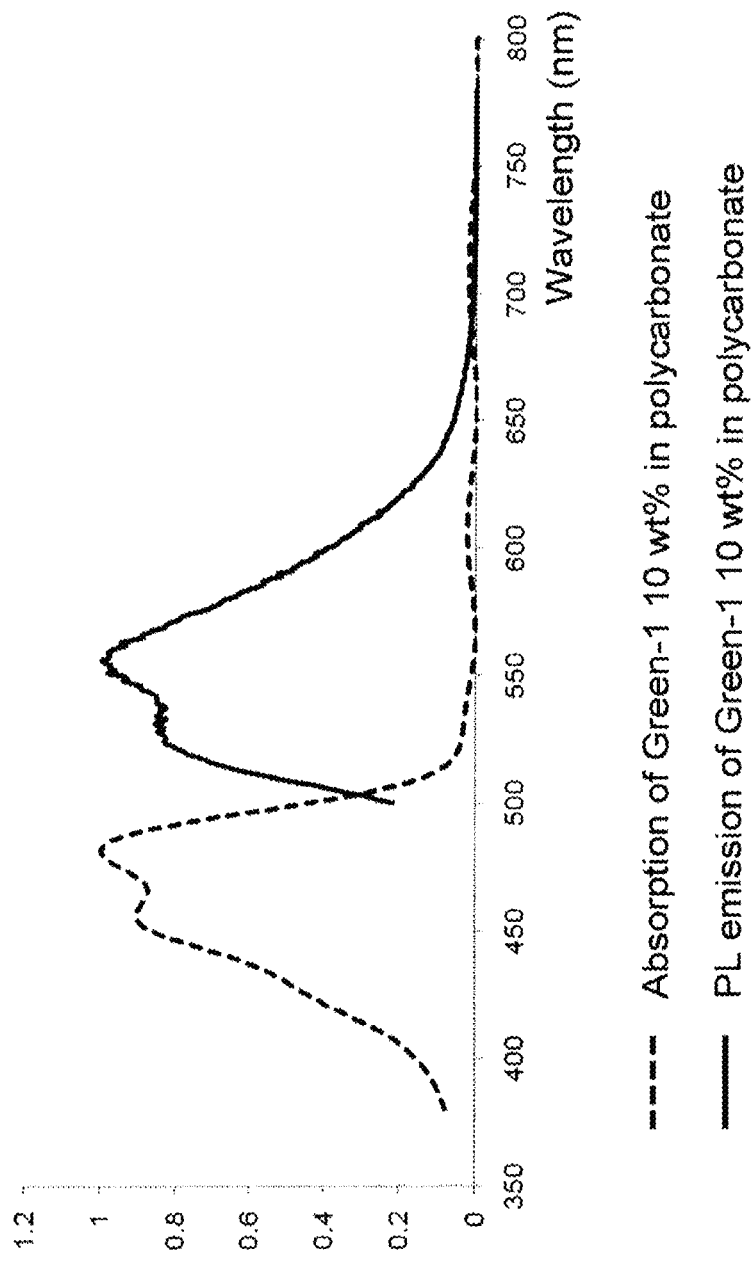
FIG. 6 shows the absorbance and emission spectra for an embodiment of an optical element described herein.

Spectral data for the optical elements of Example 2 (Device A [with polycarbonate]) was obtained. The normalized absorbance and photoluminescence of Example 2 is shown in FIG. 6. The absorbance was measured on a Varian Cary 50 scan UVN is Spectrophotometer (Agilent Technologies [Varian, Inc.], Santa Clara, Calif., USA). The photoluminescent emission data was obtained using a Jobin Yvon Horiba Fluoromax-3 fluorimeter (Horiba Jobin Yvon, Inc., Edison, N.J., USA). The excitation wavelength used to obtain this PL spectrum was 480 nm. As shown in FIG. 6, the film comprising diisobutyl 4,10-bis(4-(trifluoromethyl)phenyl)perylene-3,9-dicarboxylate and polycarbonate absorbed light in the blue region and emitted light in the green region. The absorbance ranged from about 250 nm to about 300 nm and from about 370 nm to about 520 nm. The wavelength emission ranged from about 460 nm to about 640 nm.

Figure 7:
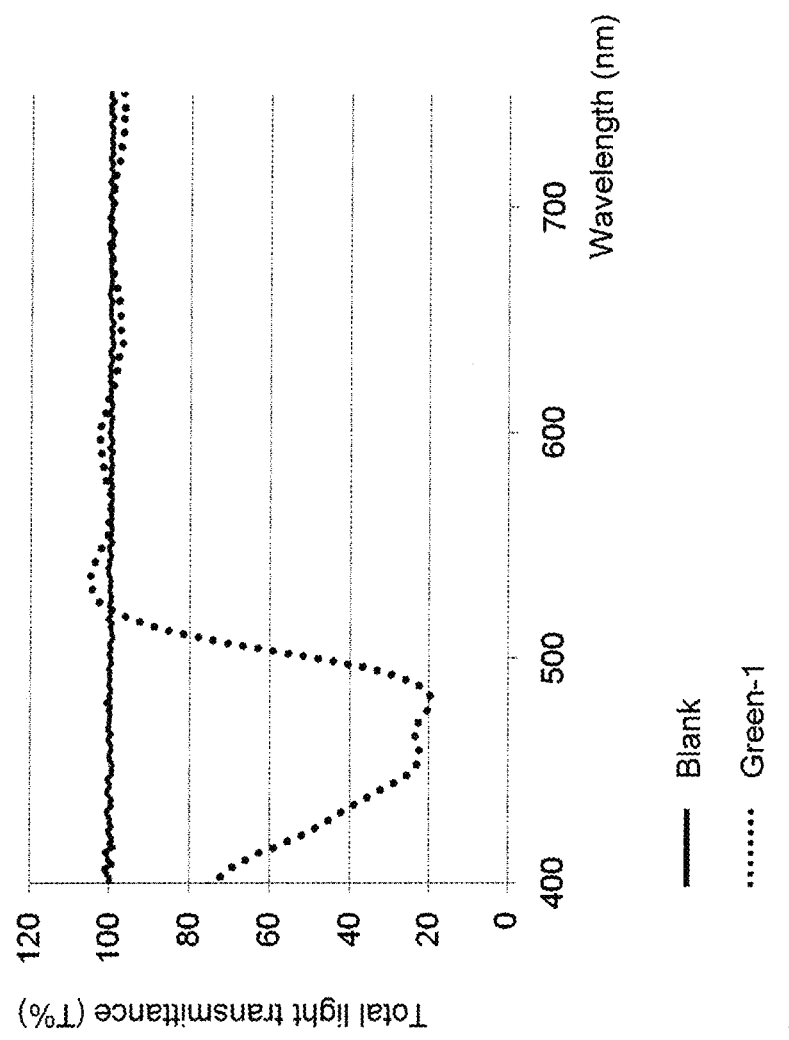
FIG. 7 shows the light transmittance spectra for an embodiment of an optical element described herein.

The transmittance of the material described in Example 1 was also measured. The compound described in Example 1 (Green-1) was spin-coated in a manner described in Example 2, except that no polycarbonate was added to the fluorescent dye Green-1. The Green-1/toluene solution was spin-coated on a glass substrate. The total light transmittance of the resulting optical element was measured on a Photal MCPD-7000 (Otsuka Electronics, Osaka, JP) using the Photal MC-2530 UV/Vis Light Source $I_2$ lamp as the illumination source. A blank glass substrate was used as a reference for 100% transmittance and is shown in FIG. 7 as "Blank." As shown in FIG. 7, the transmission of green light is actually greater than 100% in the Green-1 coated glass substrate optical element. Practically no visible light absorbance is observed from about 520 nm and higher. Some of the photons which are absorbed in the range of about 430 nm to about 500 nm are re-emitted as in the visible light range of about 530 nm to about 600 nm, causing greater than 100% transmittance at some wavelengths in that range. The peak transmittance is about 105.5% at about 534 nm.

Evaluation of Photoluminescent Quantum Yield (PLQY) of the Emitting Device Mounted Luminescent Thin Film The luminescence efficiency of the emitting thin film was evaluated by measuring the photoluminescence emitted from the emitting thin film layer under irradiation of excitation light of predetermined intensity. The measurement was performed with Otsuka Electronics (Osaka, Japan) MCPD 7000 multi channel photo detector system together with required optical components such as optical fibers (Otuka Electronics), 12-inch diameter integrating spheres (Gamma Scientific [San Diego, Calif., USA], GS0IS12-TLS), calibration light source (Gamma Scientific, GS-1512-OP1) configured for total flux measurement, and excitation blue LED light source (Cree [Durham, N.C., USA] blue-LED chip, dominant wavelength 455 nm, C455EZ1000-S2001).

Blue LED with peak wavelength of 452 nm was placed at the central position of the integrating sphere and was operated with a drive current of 25 mA. First the radiation power from the bare blue LED chip as excitation light was acquired. Next, a 15 mm×15 mm luminescent thin film of Example 2 coated glass substrate was mounted on the LED chip. Then the radiation power of the combination of the luminescent thin film and the blue LED was acquired.

The PLQY of the thin film can be expressed by the following formula:

$$\text{Wavelength Conversion Efficiency} = \frac{\phi_e(Emi)}{\phi_e(Exc)} = \frac{\int P_{emi}(\lambda) \cdot d\lambda}{\int P_{exc}(\lambda) \cdot d\lambda}$$

where at any wavelength λ, $P_{exc}(\lambda)$ is the radiation power of the excitation spectrum that is incident on the thin film layer and $P_{emi}(\lambda)$ is the radiation power in the combined spectrum of emission from the thin film layer and the excitation light. Therefore, the data of chromaticity can be given from MCPD data directly.

Optical Measurement

The efficiency measurement was performed with Otsuka Electronics MCPD 7000 multi channel photo detector system together with required optical components such as optical fibers (Otuka Electronics), 12-inch diameter integrating spheres (Gamma Scientific, GS0IS12-TLS), calibration light source (Gamma Scientific, GS-IS12-OP1) configured for total flux measurement, and excitation light source (Cree blue-LED chip, dominant wavelength 455 [452] nm, C455EZ1000-S2001).

A blue LED with peak wavelength of 452 nm was then placed at the central position of the integrating sphere and was operated with a drive current of 25 mA. First the radiation power from the bare blue LED chip as excitation light was acquired. The light emitting face distance of LED chip was 1 mm. A 15 mm×15 mm thin film covered glass substrate was then mounted a distance of about 100 µm from LED chip. The radiation powder of the combination of the thin film and the blue LED was then acquired. A PLQY value of 0.56 was acquired.

Comparative Example 1

A pair of commercially available color enhancing glasses, Solaz (Style 3), available from Solarchromic, Inc. (Colorado Springs, Colo., USA), were obtained and used as Comparative Example 1 for comparative studies.

Figure 8:
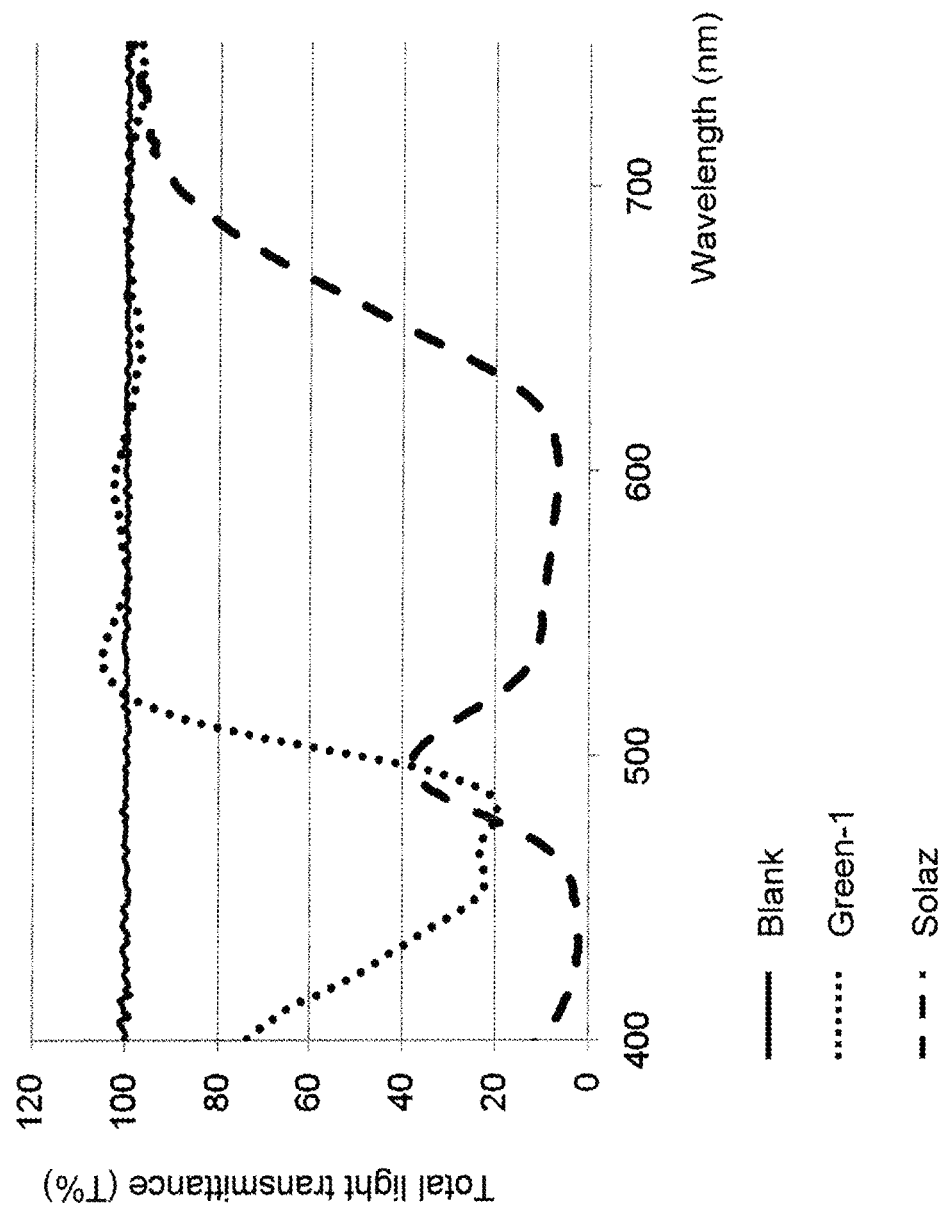
FIG. 8 shows the light transmittance spectra for an embodiment of an optical element described herein compared to a commercially available material.

The visible light transmittance of the glass substrate blank ("Blank"), the Green-1 coated glass substrate ("Green-1" [Green-1 spin coated on glass substrate/no polycarbonate]) are shown in FIG. 8. The visible light transmittance of Comparative Example 1 was also measured and the results are also shown in FIG. 8. As seen in FIG. 8, Comparative Example 1 absorbs a large amount of visible wavelength light. The transmittance is below about 20% for most of the visible light spectrum. Since this device absorbs so much light, it is not effective in low and medium light situations.

Results

The optical element made in Example 6 (Device A) was tested for correcting visual insensitivity between a first visible color wavelength and a second visible color wavelength. The optical element, in the form of a film, was affixed to a pair of clear safety glasses. An official Ishihara color blindness test book (38 plates) (*Ishihara's Tests for Colour Deficiency*, Shinobu Ishihara, Kanehara Trading Inc., Tokyo, Japan, [2009]) for the determination of color blindness symptoms (also available from http://www.allegromedical.com/diagnostic-products-c521/official-ishihara-color-blindness-test-p192016.html), was placed before a 26 year-old male who has been previously diagnosed with deuteranomaly.

The visual testing was performed in an ambient lighted room. The subject viewed the Ishihara color blindness test book (38 plates) with the naked eye, with Example 6, and with Comparative Example 1. The subject acknowledged that he was unable to discern several of the hidden shapes within the Ishihara color blindness test book (38 plates) when viewed with the naked eye, i.e. without an optical element.

The optical element from Example 6 and the glasses from Comparative Example 1 were alternatively inserted separately into the vision path of the subject. After viewing 38 test images through each separate example, the subject was asked subjectively how easily he could discern the hidden shapes in the visual test examples and was asked to trace what portion of the hidden image he could discern. The subject reported that, with the optical element from Example 6, he was able to discern a greater portion of the hidden image or the entire image of the hidden shape for 17 more plates with Example 6 inserted into the vision path of the subject as compared with Comparative 1. Furthermore, the subject reported that the glasses from Comparative Example 1, in some cases, rendered the hidden shape completely indistinguishable from the background. Thus, the optical element from Example 6 provided improved color discernment over both the naked eye and commercially available glasses.

Thus, in some embodiments, an optical element may have an absorption and/or emission profile similar to that depicted in FIG. 6. For example, an optical element may absorb light having a wavelength of about 425 nm to about 500 nm, about 440 nm to about 500 nm, about 450 nm, or about 530 nm. In some embodiments, an optical element may emit light having a wavelength of about 510 nm to about 585 nm, about 515 nm to about 575 mm, about 530 nm, or about 560 nm. Similarly, in some embodiments and optical element may have a transmittance spectrum to that of the FIG. 7. For example, an optical element may have a transmittance peak at a wavelength of about 500 nm to about 700 nm, about 510 nm to about 550 nm, about 550 nm to about 620 nm, or about 640 nm to about 720 nm. In some embodiments the transmittance at a peak may be greater than: about 90%, about 95%, or about 100%.

Example 7

Optical Element

Example 7 (Device B) was constructed in a similar manner as Example 6, except that the amount of luminescent dye, diisobutyl 4,10-bis(4-(trifluoromethyl)phenyl)perylene-3,9-dicarboxylate in the film was reduced to about 5% by weight of the composition. A light absorbing dye, Epolight 6661 (Epolin, Inc., Newark, N.J., USA), was added to the film in an amount resulting in 5% by weight of the composition.

Figure 9:
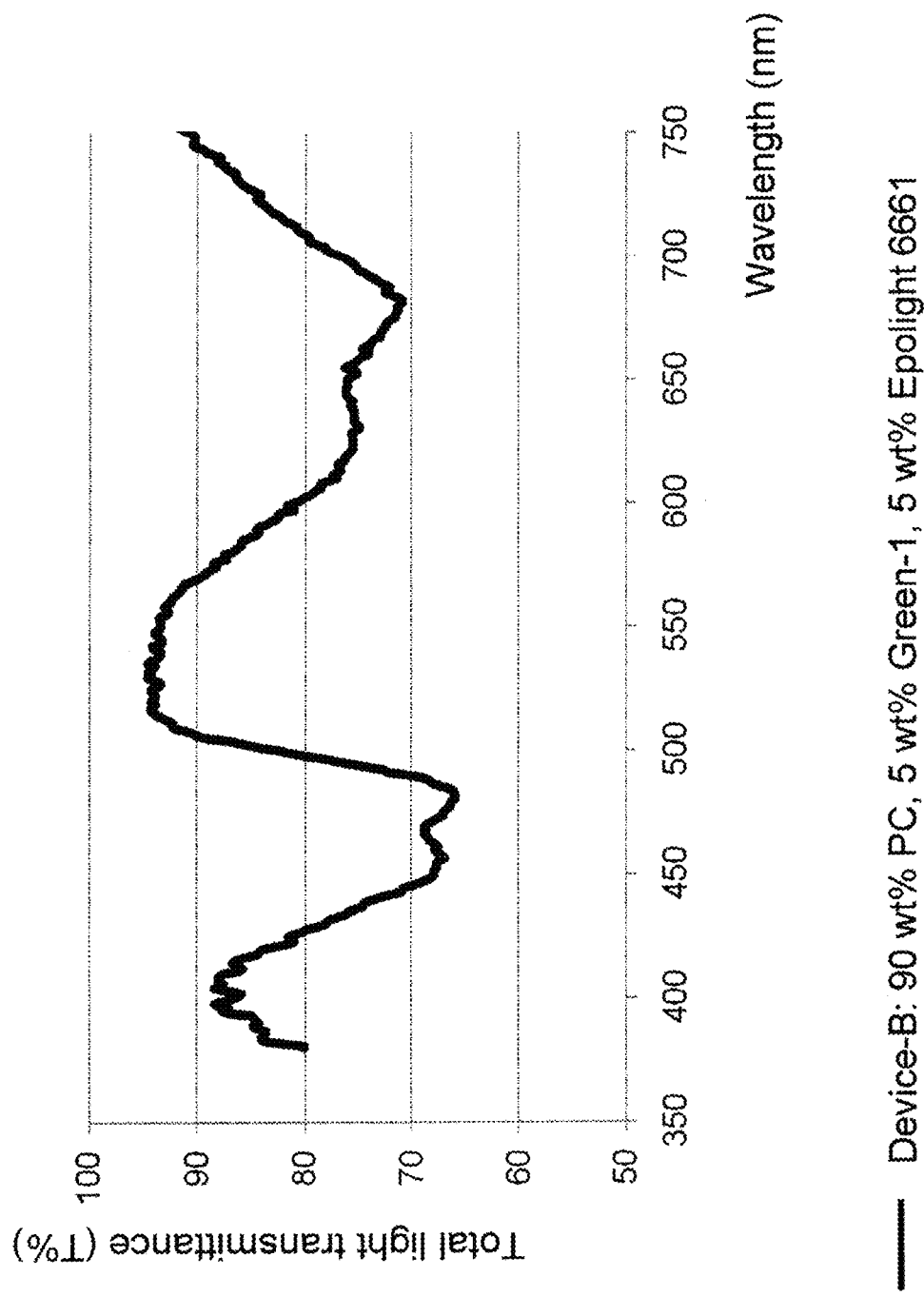
FIG. 9 shows the light transmittance spectra for another embodiment of an optical element described herein.

The transmittance of Example 7 was also measured, using the same method as described in Example 6. The results are shown in FIG. 9. As shown in FIG. 9, the optical element of Example 7 shows high transmittance in the green wavelength range and attenuated transmittance in the red wavelength range. This enhances color discrimination by persons having visual insensitivity between red and green color hues.

The visual test for the determination of color blindness symptoms as set forth above was repeated with the same individual using Example 7. After viewing 38 test images through each separate example, the subject was asked subjectively how easily he could discern the hidden shapes in the visual test examples. The subject reported that with the optical element from Example 7 he was able to discern a portion of the hidden image or the entire image of the hidden shape for 18 more plates with Example 7 as compared with Comparative 1. Those 18 plate included the same 17 plates perceived with Example 2, but in a majority of plates, the subject stated he was better able (easier to discern, discerned more of the hidden image). Thus, both Example 6 and Example 3 enhanced color perception in generally the same plates compared to both the naked eye and Comparative Example 1.

Thus, in some embodiments an optical element may have a transmittance spectrum similar to that depicted in FIG. 9. For example, an optical element may have a transmittance peak at a wavelength of about 350 nm to about 400 nm, about 375 nm to about 425 nm, about 500 nm to about 600 nm, or about 500 nm to about 550 nm. In some embodiments, transmittance at a peak may be greater than about 80%, about 85%, about 90%, or about 92%.

Example 8

Optical Element

Additional devices were constructed in a similar manner as Example 2, except that the amount of luminescent dye, diisobutyl 4,10-bis(4-(trifluoromethyl)phenyl)perylene-3,9-dicarboxylate, in the films was about 9 wt % by total weight (in Device C) and about 3 wt % by total weight (in Device D).

Another set of devices were constructed in a similar manner as Example 2. The amount of luminescent dye, diisobutyl 4,10-bis(4-(trifluoromethyl)phenyl)perylene-3,9-dicarboxylate (Green-1), in the films was about 10 wt % by total weight (in Device E), about 2.5 wt % by total weight (in Device F), and about 1 wt % by total weight (in Device G). Furthermore, a second luminescent compound, N-phenyl-N-(4'-(1-phenyl-1H-benzo[d]imidazol-2-yl)-[1,1'-biphenyl]-4-yl)naphthalen-1-amine, was added to the optical elements of Devices E, F, and G. In Device E, Blue-1 was added in an amount of about 2.5 wt % by total weight. In Device F, Blue-1 was added in an amount of about 10 wt % by total weight. In Device G, Blue-1 was added in an amount of about 10 wt % by total weight.

The transmittance of the devices in Example 4 were also measured, using the same method as described in Example 2. The results are shown in Table 9.

TABLE 4

Transmittance of Devices C-G

| Device | Green-1 amount | Blue-1 amount | Peak transmissive wavelength | MCPD emissive intensity |
|---|---|---|---|---|
| C | 9 wt % | 0 wt % | 534 nm | 105.45% |
| D | 3 wt % | 0 wt % | 536 nm | 100.83% |
| E | 10 wt % | 2.5 wt % | 557 nm | 102.05% |
| F | 2.5 wt % | 10 wt % | 545 nm | 102.46% |
| G | 1 wt % | 10 wt % | 536 nm | 101.74% |

As shown in Table 9, the optical elements of Example 4 show a high transmittance in the green visible light wavelength without a concurrent decrease in the measured intensity of the emitted light. This allows for tuning of the peak transmissive wavelength, and enhances color discrimination by persons having visual insensitivity between red and green color hues.

Thus, in some embodiments, an optical element may have a peak transmissive wavelength around that of any of devices C-G in Table 4. For example, an optical element may have a peak transmissive wavelength of about 530 nm to about 540 nm, about 535 nm to about 540 nm, about 540 nm to about 550 nm, about 545 nm to about 550 nm, or about 555 nm to about 560 nm. In some embodiments, a peak may have a transmittance of at least: about 100%, about 102%, or about 105%.

Example 9

PVBAA (160 mg) was dissolved in 3.04 g of anhydrous reagent alcohol by sonicating for 2 hours. Then, 8 mg of Rhodamine 6G was added to the solution and sonication was applied for 10 minutes. Note that the final composition of this solution was approximately 4.75 wt % polymer, 0.25 wt % rhodamine 6G, and 95% solvent. Then the solution was spin coated onto a cleaned glass slide which was cut to 5 cm×5 cm. After spin coating, the film was dried on a hot plate set to 100° C. for 10 minutes. Note that after evaporating the solvent, the final composition of the dry film is 5 wt % rhodamine 6G in 95 wt % polymer.

PVBAA (160 mg, Sigma-Aldrich, Milwaukee, Wis., USA #418420), was dissolved in 3.04 g of anhydrous n-butanol by sonicating for about 2 hours. Then, 8 mg of Rhodamine 6G (Sigma-Aldrich) was added to the solution and sonication was applied for about 10 minutes with a resultant solution of approximately 4.75 wt % polymer, 0.25 wt % rhodamine 6G, and 95% solvent. The resulting solution was spin coated (at about 2000 rpm for about 10 seconds after ramp up from 0-2000 rpm of about 0.1 seconds) onto a cleaned glass slide which had been cut to about 5 cm×5 cm. After spin coating, the film was dried on a hot plate, in air, at about 10° C. for about 10 minutes resulting in a dried film of about 5 wt % rhodamine 6G in 95 wt % polymer. The film had the transmittance spectrum depicted in FIG. 10, and the absorption and emission spectra depicted in FIG. 11.

Figure 10:
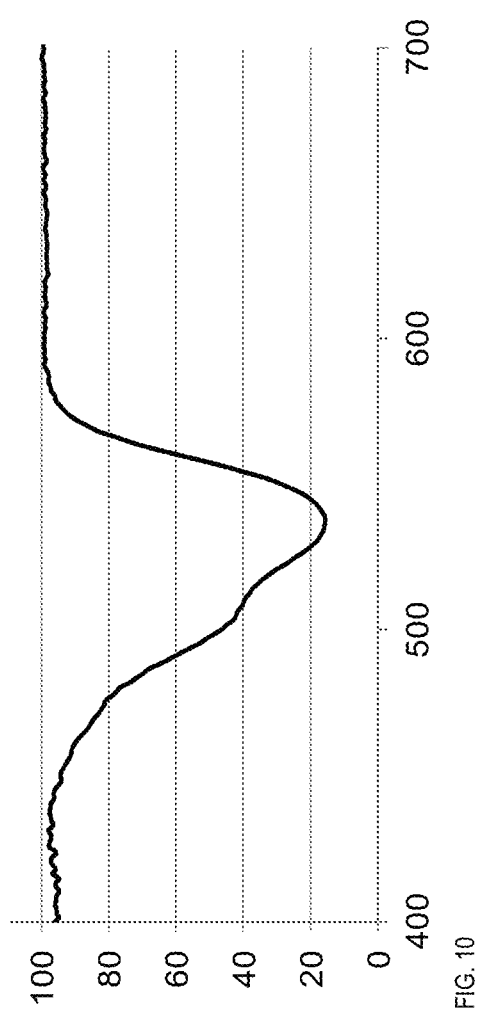
FIG. 10 shows the light transmittance spectra for an embodiment of an optical element described herein.
Figure 11:
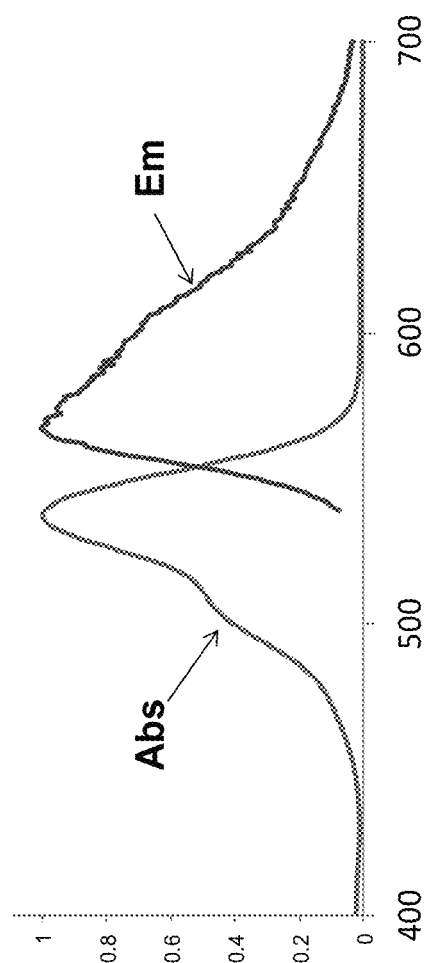
FIG. 11 shows the absorbance and emission spectra for an embodiment of an optical element described herein.

Thus, in some embodiments, an optical element may have a transmittance profile similar to that depicted in FIG. 10, and/or an absorption and/or emission spectrum similar to that depicted in FIG. 11. For example, similar to FIG. 10, some optical elements may have a transmissive plateau in the range of about 600 nm to about 700 m. In that range, the transmittance may be greater than about 90%, about 95%, or about 99%. Similar to FIG. 11, in some embodiments an optical element may absorb light having a wavelength of about 500 nm to about 560 nm, about 520 nm to about 550 nm, or about 523 nm. In some embodiments, an optical element may emit light at a wavelength of about 550 nm to about 615 nm, about 560 nm to about 610, or about 568 nm An optical element was prepared as described in Example 2 using the rhodamine 6G film. The optical element, in the form of a film, was affixed to a pair of clear safety glasses. The visual test for the determination of color blindness symptoms as set forth above was repeated with the same individual using Example 3. The individual was able to discern all of the hidden image or shape for all 38 plates.

Example 10

Optical Element (Device I)

The luminescent dye, Rhodamine 6G, was used without addition extraction or purification, and was intermixed with a coating solution comprising a silica-filled methylpolysiloxane polymer [PermaNew 6000, 28% solids] (California Hardcoating Co., Chula Vista, Calif., USA) in an amount resulting in a luminescent dye:total solution weight ratio of about 0.25: 99.75. The resulting solution was then spin-coated at about 2000 rpm, for about 10 seconds onto a clean pre-cut plastic lens made of allyl diglycol carbonate (CR-39 plastic, SP Optical Labs, Vista, Calif.). The resulting coated lens was then heated to about 120° C. for about four (4) hours under air to cure the coating material. The weight percentage of the luminescent compound in the cured coating was about 1 wt % based upon the weight of the composition.

Additional devices were constructed in a similar manner as Device I, except that the amount of luminescent dye, Rhodamine 6G was about 0.5 wt % by total weight (in Device J), about 0.75 wt % by total weight (in Device K), and about 1.0 wt % by total weight (in Device L).

Example 11

Pyrromethene 605 (PM605) [Exciton, Inc] (0.082 g), UNIDIC 17-806 [ionizing radiation curable paint (UniDic 17-806, solids content 80%, Dainippon Ink and Chemicals, (10 g); photopolymerization initiator (IRGACURE 907, Ciba Specialty Chemicals K. K.) (0.24 g), coating additive-gamma-methacryloxypropyltrimethoxysilane (PC4100, Power Chemica) (0.008 g) were dissolved in cyclopentanone (5.32 g) and 1-methoxy-2-propanol (7.98 g) by sonicating for about 2 hours The resulting solution was hand cast onto a PET substrate. After casting, the film was dried in an air circulating oven, in air, at about 90° C. for about 60 seconds to evaporate the solvents. The film was then irradiated with a 500 W Xe/HgXe lamp until a dose of at least 250J/cm$^2$ of UV radiation was applied to the film, resulting in a cured film of about 1 wt % pyrromethene 605 in 99 wt % polymer. The film had the transmittance spectrum depicted in FIG. 12, and the absorption and emission spectra depicted in FIG. 13.

Figure 12:
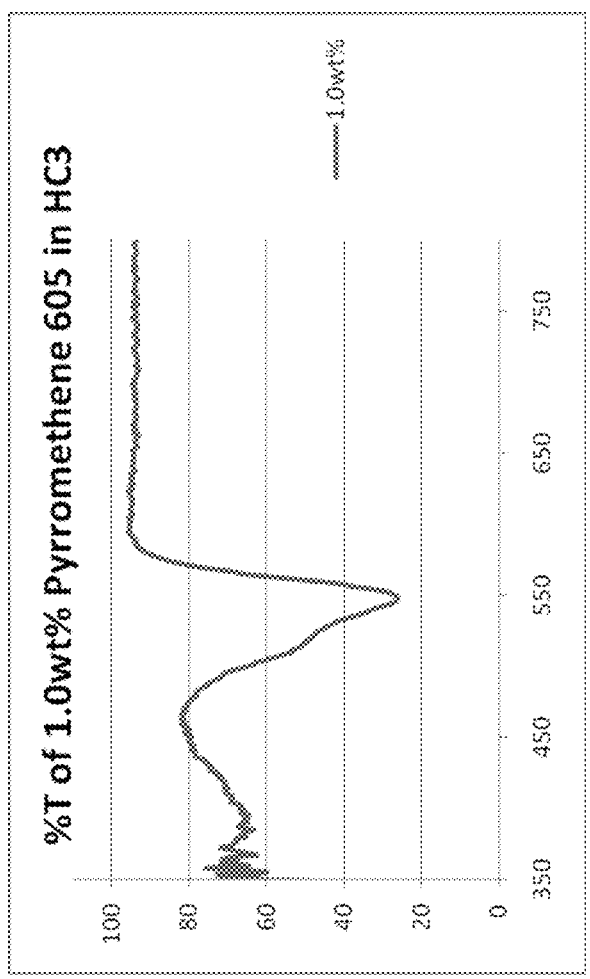
FIG. 12 shows the light transmittance spectra for an embodiment of an optical element described herein.
Figure 13:
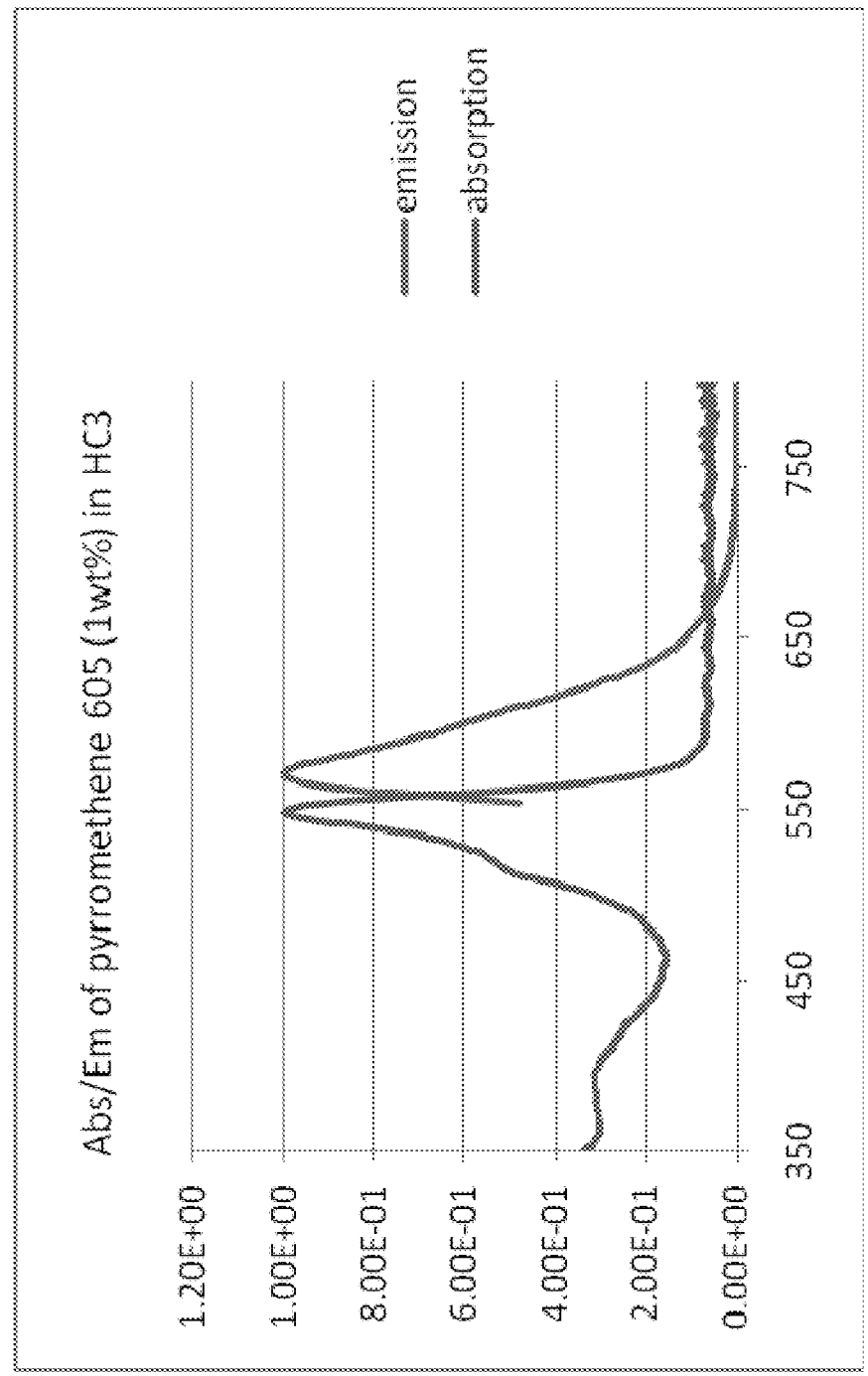
FIG. 13 shows the absorbance and emission spectra for an embodiment of an optical element described herein.

Thus, in some embodiments, an optical element may have a transmittance profile similar to that depicted in FIG. 12, and/or an absorption and/or emission spectrum similar to that depicted in FIG. 13. For example, similar to FIG. 12, some optical elements may have a transmissive plateau in the range of about 600 nm to about 800 nm. In that range, the transmittance may be greater than about 80% or about 90%. Similar to FIG. 13, in some optical elements may absorb light at a wavelength of about 500 nm to about 560 nm, about 540 nm to about 550 nm, or about 550 nm. In some embodiments an optical element may emit light at a wavelength of about 550 nm to about 650 nm, about 560 nm to about 600 nm, or about 570 nm.

An optical element was prepared as described in Example 6 using the rhodamine 6G film. The optical element, in the form of a film, was affixed to a pair of clear safety glasses (Device M). The visual test for the determination of color blindness symptoms as set forth above was repeated with the same individual using Example 7. The individual was able to discern all of the hidden image or shape for all 38 plates.

Figure 14:
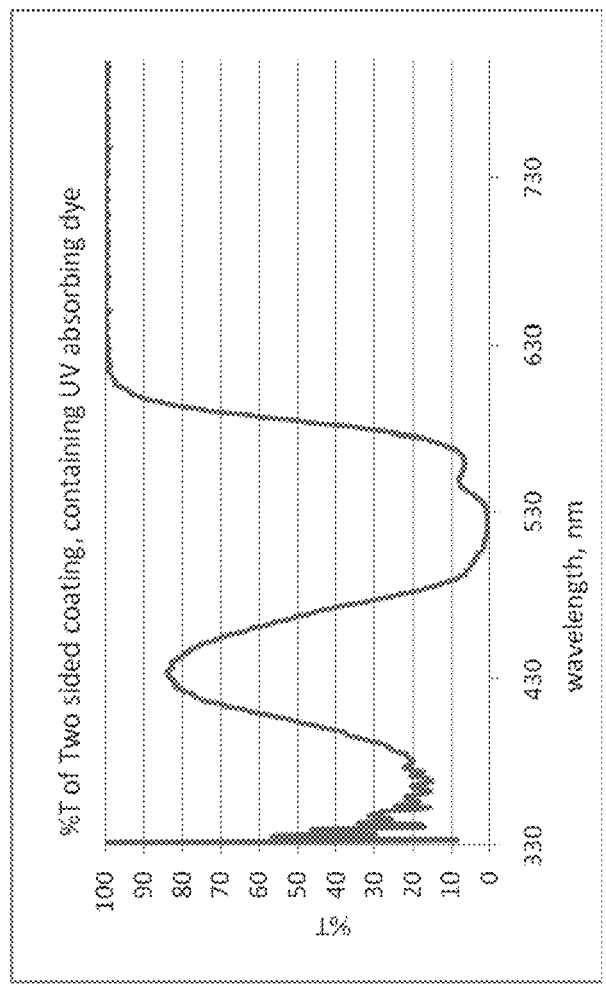
FIG. 14 shows the light transmittance spectra for an embodiment of a polymerizable dye described herein.

Similar to FIG. 14, some optical elements may have a transmissive plateau from about 630 nm to about 800 nm. Such a transmissive plateau may have a transmittance of greater than about 90%, about 95%, or about 99%.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. An ocular lens comprising: an optical element comprising a luminescent compound in a substantially transparent matrix; wherein the device is configured so that the optical element modifies a color of an object or image viewed through the optical element by a user to thereby allow the user to better distinguish colors;
   wherein the luminescent compound absorbs light at an absorption wavelength and emits light at an emission wavelength, wherein a human cone photopigment is substantially more sensitive to the emission wavelength than to the absorption wavelength;
   wherein the luminescent compound has an average wavelength of visible absorption of about 380 nm to about 450 nm.

2. An ocular lens comprising: an optical element comprising a luminescent compound in a substantially transparent matrix; wherein the device is configured so that the optical element modifies a color of an object or image viewed through the optical element by a user to thereby allow the user to better distinguish colors;

wherein the luminescent compound absorbs light at an absorption wavelength and emits light at an emission wavelength, wherein a human cone photopigment is substantially more sensitive to the emission wavelength than to the absorption wavelength;

wherein the luminescent compound has an average wavelength of visible absorption of about 420 nm to about 480 nm.

3. An ocular lens comprising: an optical element comprising a luminescent compound in a substantially transparent matrix; wherein the device is configured so that the optical element modifies a color of an object or image viewed through the optical element by a user to thereby allow the user to better distinguish colors;

wherein the luminescent compound absorbs light at an absorption wavelength and emits light at an emission wavelength, wherein a human cone photopigment is substantially more sensitive to the emission wavelength than to the absorption wavelength;

wherein the luminescent compound has an average wavelength of visible emission of about 500 nm to about 600 nm.

4. The ocular lens of claim 1, wherein the ocular lens is an intraocular lens.

5. The ocular lens of claim 1, wherein the ocular lens is a hard contact lens.

6. The ocular lens of claim 1, wherein the ocular lens is a soft contact lens.

7. The ocular lens of claim 1, wherein the optical element comprises a hydrogel polymer.

8. The ocular lens of claim 7, wherein the hydrogel polymer incorporates a hydrophilic acrylate monomer.

9. The ocular lens of claim 8, wherein the hydrogel polymer further incorporates an alkyl acrylate monomer or an alkyl methacrylate monomer.

10. The ocular lens of claim 2, wherein the ocular lens is an intraocular lens.

11. The ocular lens of claim 2, wherein the ocular lens is a hard contact lens.

12. The ocular lens of claim 2, wherein the ocular lens is a soft contact lens.

13. The ocular lens of claim 2, wherein the optical element comprises a hydrogel polymer.

14. The ocular lens of claim 13, wherein the hydrogel polymer incorporates a hydrophilic acrylate monomer.

15. The ocular lens of claim 14, wherein the hydrogel polymer further incorporates an alkyl acrylate monomer or an alkyl methacrylate monomer.

16. The ocular lens of claim 3, wherein the ocular lens is an intraocular lens.

17. The ocular lens of claim 3, wherein the ocular lens is a hard contact lens.

18. The ocular lens of claim 3, wherein the ocular lens is a soft contact lens.

19. The ocular lens of claim 3, wherein the optical element comprises a hydrogel polymer.

20. The ocular lens of claim 19, wherein the hydrogel polymer incorporates a hydrophilic acrylate monomer.

21. The ocular lens of claim 20, wherein the hydrogel polymer further incorporates an alkyl acrylate monomer or an alkyl methacrylate monomer.

* * * * *